United States Patent
Saum et al.

(10) Patent No.: US 12,371,719 B2
(45) Date of Patent: Jul. 29, 2025

(54) FERMENTATIVE PRODUCTION OF N-BUTYLACRYLATE USING ALCOHOL ACYL TRANSFERASE ENZYMES

(71) Applicant: BASF SE, Ludwigshafen am Rhein (DE)

(72) Inventors: Stephan Saum, Lampertheim (DE); Woncheol Kim, Tarrytown, NY (US); Oskar Zelder, Ludwigshafen (DE); Jennifer Jaitzig, Ludwigshafen (DE); Zheyuan Guo, San Diego, CA (US)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 18/419,647

(22) Filed: Jan. 23, 2024

(65) Prior Publication Data

US 2024/0158820 A1 May 16, 2024

Related U.S. Application Data

(62) Division of application No. 16/089,642, filed as application No. PCT/EP2017/056872 on Mar. 22, 2017, now Pat. No. 11,913,054.

(30) Foreign Application Priority Data

Mar. 30, 2016 (EP) .................... 16162887

(51) Int. Cl.
C12P 7/62 (2022.01)
C12N 9/10 (2006.01)

(52) U.S. Cl.
CPC .............. *C12P 7/62* (2013.01); *C12N 9/1029* (2013.01); *C12Y 203/01084* (2013.01)

(58) Field of Classification Search
CPC .. C12Y 203/01084; C12P 7/62; C12N 9/1029
See application file for complete search history.

(56) References Cited

U.S. PATENT DOCUMENTS

| | | | |
|---|---|---|---|
| 5,565,350 A | 10/1996 | Kmiec | |
| 11,913,054 B2 * | 2/2024 | Saum | C12Y 203/01084 |
| 2009/0130729 A1 | 5/2009 | Symes et al. | |
| 2009/0155869 A1 | 6/2009 | Buelter et al. | |
| 2015/0184207 A1 | 7/2015 | Sato et al. | |
| 2019/0112622 A1 | 4/2019 | Saum et al. | |

FOREIGN PATENT DOCUMENTS

| | | | |
|---|---|---|---|
| EP | 2848694 A1 | 3/2015 | |
| WO | 0015815 A1 | 3/2000 | |
| WO | 0032789 A1 | 6/2000 | |
| WO | 2007039415 A1 | 4/2007 | |
| WO | 2008143704 A2 | 11/2008 | |
| WO | 2010105194 A2 | 9/2010 | |
| WO | 2014062556 A2 | 4/2014 | |

OTHER PUBLICATIONS

Kandasamy et al., "Engineering *Escherichia coli* with acrylate pathway genes for propionic acid synthesis and its impact on mixed-acid fermentation", Appl Microbiol Biotechnol (2013) 97: 1191-1200.
Teufel et al., "3-Hydroxypropionyl-Coenzyme A Dehydratase and Acryloyl-Coenzyme A Reductase, Enzymes of the Autotrophic 3-Hydroxypropionate/4-Hydroxybutyrate Cycle in the Sulfolobales", Journal of Bacteriology, Jul. 2009, p. 4572-4581.
El-Sharkawy et al., "Functional characterization of a melon alcohol acyl-transferase gene family involved in the biosynthesis of ester volatiles", Plant Molecular Biology, Oct. 2005.
Schadeweg and Boles, "Increasing n-butanol production with *Saccharomyces cerevisiae* by optimizing acetyl-CoA synthesis, NADH levels and trans-2-enoyl-CoA reductase expression". Biotechnol Biofuels (2016) 9:257.
Yahyaoui et al., "Molecular and biochemical characteristics of a gene encoding an alcohol acyl-transferase involved in the generation of aroma volatile esters during melon ripening", Eur J Biochem (2002) 269, 2359-2366.
Steen et al., "Metabolic engineering of *Saccharomyces cerevisiae* for the production of n-butanol", Microbial Cell Factories 2008, 7:36.
Nevoigt, "Progress in Metabolic Engineering of *Saccharomyces cerevisiae*", Microbiol Mol Biol Rev, Sep. 2008 72 (3), p. 379-412.
Oeser et al., "Metabolic engineering of yeast for increased efficiency and yield in industrial fuel ethanol production", Yeast 32(1), S88.
Lowry et al., "Protein measurement with the folin phenol reagent", J Biol Chem (1951) 193: 265-275.
Bradford, "A Rapid and Sensitive Method for the Quantitation of Microgram Quantities of Protein Utilizing the Principle of Protein-Dye Binding", Analyt Biochem (1976) 72: 248-254.
Wang and De Luca, "The biosynthesis and regulation of biosynthesis of Concord grape fruit esters, including 'foxy' methylanthranilate", The Plant Journal (2005) 44, 606-619.
Stewart et al., "The Pun1 gene for pungency in pepper encodes a putative acyltransferase", The Plant Journal (2005) 42, 675-688.
Cregg et al., "Pichia pastoris as a Host System for Transformations", Molecular and Cellular Biology (Dec. 1985) 5 (12), p. 3376-3385.
Prabhu et al., "Effect of ethanolic and ethylacetate extract of Merremia emarginata (Burm.F) in Rheumatoid Arthritis", IRJP 2012, 3(9).
Altschul et al., "Gapped BLAST and PSI-BLAST: a new generation of protein database search programs", Nucleic Acids Research, 1997, vol. 25, No. 17, 3389-3402.
Smith and Waterman, "Comparison of Biosequences", Adv Appl Math 2 (1981), 482-489.
Pearson and Lipman, "Improved tools for biological sequence comparison", Proc Natl Acad Sci USA, Apr. 1988, vol. 85, pp. 2444-2448.

(Continued)

*Primary Examiner* — Tekchand Saidha
(74) *Attorney, Agent, or Firm* — Armstrong Teasdale LLP

(57) ABSTRACT

Provided herein is a recombinant nucleic acid molecule, a recombinant microorganism, and a method for fermentative production of n-butylacrylate and other esters from alcohols and acyl-CoA units using alcohol acyl transferase enzymes.

9 Claims, 4 Drawing Sheets
Specification includes a Sequence Listing.

(56) References Cited

OTHER PUBLICATIONS

International Search Report and Written Opinion for International Application No. PCT/EP2017/056872, dated May 12, 2017, 10 pages.
Chu et al., "Direct fermentation route for the production of acrylic acid", Metabolic Engineering, vol. 32, Nov. 2015, pp. 23-29.
Krivoruchko et al., "Improving biobutanol production in engineered *Saccharomyces cerevisiae* by manipulation of acetyl-CoA metabolism", Journal of Industrial Microbiology & Biotechnology, vol. 40, Issue 9, Sep. 2013, pp. 1051-1056.
Tang et al., "Metabolic engineering for enhanced fatty acids synthesis in *Saccharomyces cerevisiae*", Metabolic Engineering, vol. 16, Mar. 2013, pp. 95-102.
Zhou et al., "Erlotinib versus chemotherapy as first-line treatment for patients with advanced EGFR mutation-positive non-small-cell lung cancer (Optimal, CTONG-0802): a multicentre, open-label, randomised, phase 3 study", The Lancet Oncology, vol. 12, Issue 8, Jul. 22, 2011, pp. 735-742.
UniProt Accession No. P93094_CUCME, published May 1, 1997 (1997).
UniProt Accession No. B1A9J8_CUCME, published May 8, 2008 (2008).
UniProt Accession No. Q8GTM5_FRAVE, published Mar. 1, 2003 (2003).
UniProt Accession No. Q6R311_MALDO, published Jul. 5, 2004 (2004).
UniProt Accession No. BEBT_CLABR, published Mar. 1, 2003 (2003).
UniProt Accession No. BEATH_CLABR, published Aug. 1, 1998 (1998).

\* cited by examiner (a)   (b)

FERMENTATIVE PRODUCTION OF N-BUTYLACRYLATE USING ALCOHOL ACYL TRANSFERASE ENZYMES

CROSS-REFERENCE TO RELATED APPLICATIONS

This application is a divisional application of U.S. application Ser. No. 16/089,642, filed Sep. 28, 2018, which is a U.S. National Phase Application of International Patent Application No. PCT/EP17/56872, filed Mar. 22, 2017, which claims the benefit of priority to European Patent Application No. 16162887.0, filed Mar. 30, 2016, the entire contents of which are hereby incorporated by reference herein

REFERENCE TO AN ELECTRONIC SEQUENCE LISTING

The contents of the electronic sequence listing (DIV sequence listing_27843-2467.xml; Size: 194,086 bytes; and Date of Creation: Oct. 25, 2023) is herein incorporated by reference in its entirety.

FIELD OF THE INVENTION

The invention is directed to a recombinant nucleic acid molecule, a recombinant microorganism and to a method for fermentative production of n-butylacrylate and other esters from alcohols and acyl-CoA units using alcohol acyl transferase enzymes.

BACKGROUND

Acrylate esters are among the most versatile monomers for providing performance properties to a wide variety of polymers. Acrylate esters are chemically produced with acrylic acid and alcohols. For instance, n-butylacrylate (n-BA) is produced by esterifying acrylate with butanol.

Production of n-BA in a biological system has not been demonstrated. A pathway for the production of n-BA in a biological system may comprise an acryloyl-CoA biosynthesis pathway and a butanol biosynthesis pathway. In addition, for fermentative production of n-BA, an alcohol acyl transferase (AAT) enzyme, capable of catalysing an esterification reaction between acryloyl-CoA and butanol, forming an ester bond, would need to be present in a production system, such as a microorganism. Currently, multiple pathways have been reported for the production of acryloyl-CoA or butanol in a biological system via natural or engineered pathways (Teufel, Kung et al. 2009) (Schadeweg and Boles 2016).

Also, various publications describe AAT enzyme activities that combine acyl-CoAs with alcohols through ester formation (El-Sharkawy, Manriquez et al. 2005). They show that some AATs have broad substrate specificities resulting in various ester products. However, no AAT enzymes capable of forming n-BA esters in a biological system by esterification of acryloyl-CoA and butanol were described known.

The physiological properties of acryloyl-CoA and butanol and their intermediates limited the functionality and/or the capacity of fermentative production of these products in microorganisms (Zhou, Zhang et al. 2011). Many difficulties, such as reducing power imbalance, toxicity, ATP imbalance, and oxygen sensitivity of enzymes also make the development of engineered strain to produce acryl ester cumbersome.

Especially, acrylate, butanol, and n-BA are toxic to the cells. Although, there are some examples in public for producing acrylate and butanol by fermentation separately in yeast and various other host strains, there is no reported biological method to produce n-butyl acrylate in a biological system due to the lack of adequate AAT enzymes catalysing the esterification reaction.

Today n-BA is mainly produced from chemical methods based on petroleum based feedstock. Availability of a sustainable method for producing acrylate esters is becoming interesting. One way for such a sustainable method could be a biological system for fermentative production of acrylate esters from renewable feed stock, such as glucose or lignocellulose. Fermentative n-BA production is hypothetically possible, if acryloyl-CoA and butanol are produced in a cell and subsequently combined to form n-BA by an AAT enzyme.

Identifying AAT enzymes catalysing this esterification step is a key challenge for providing such fermentative production system.

SUMMARY

It is therefore one objective of the invention at hand to provide AAT enzymes having an activity of esterifying acryloyl-CoA and butanol to form n-BA. Furthermore, it is an objective of the invention at hand to develop a microorganism capable of fermentative production of n-BA by esterification of acryloyl-CoA and butanol and to provide fermentation systems for the production of n-BA.

It is an additional objective of the invention at hand to provide AAT enzymes having an activity of esterifying propionyl-CoA and butanol to form butylpropionate and/or of esterifying lactoyl-CoA and butanol to form butyl lactate and or of esterifying acetyl-CoA and ethanol to form ethyl acetate. Further it is an objective of the invention at hand to develop microorganisms capable of fermentative production of butyl propionate, butyl lactate and/or ethyl acetate by esterification of propionyl-CoA and butanol, lactoyl-CoA and butanol and/or acetyl-CoA and ethanol, respectively and to provide fermentation systems for the production of butyl propionate, butyl lactate and/or ethyl acetate.

DETAILED DESCRIPTION OF THE INVENTION

Figure 1:
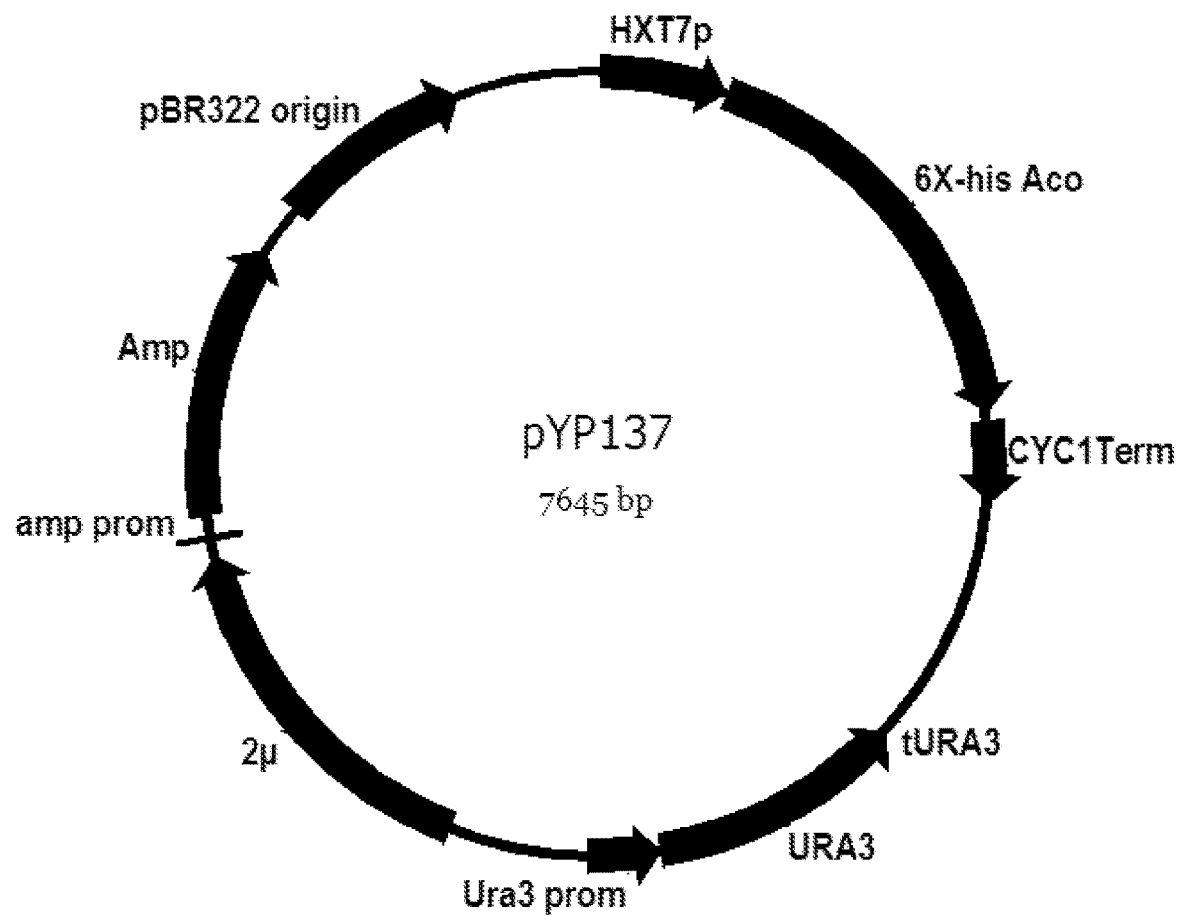
FIG. 1 is a diagram of pYP137 construction vector for overexpression of Aco in S. cerevisiae.

One embodiment of the invention is a method for fermentative production of n-butylacrylate (n-BA) comprising the steps of i) providing a recombinant microorganism comprising a butanol producing pathway, an acryloyl-CoA producing pathway and expressing an AAT gene encoding an AAT enzyme having an n-BA forming activity and ii) culturing said microorganism under conditions that allow for the production of n-BA and iii) recovering n-BA from the fermentation broth.

The term AAT enzyme or AAT enzyme activity means an enzyme or an enzyme activity as defined by EC 2.3.1.84, catalysing an esterification step, transferring an acyl-CoA to an alcohol. An AAT enzyme having an n-BA forming activity means an AAT enzyme catalysing the reaction of acryloyl-CoA and butanol to n-BA and CoA. The AAT enzyme may be endogenous or heterologous to the microorganism.

A "butanol producing pathway" means a metabolic pathway comprising all enzymes catalysing the biochemical reactions to form butanol from other metabolite(s). Such pathways have previously been established in microorganisms as for example described in (Schadeweg and Boles 2016).

A "acryloyl-CoA producing pathway" means a metabolic pathway comprising all enzymes catalyzing the biochemical reactions to form acryloyl-CoA from other metabolite(s). Such pathways have previously been established in microorganisms as for example described in (Zhou, Zhang et al. 2011) (Chu, Ahn et al. 2015).

Another embodiment of the invention is a method for fermentative production of n-BA as described above wherein the AAT gene encoding an AAT enzyme having an n-BA forming activity is selected from the group consisting of (I) a nucleic acid molecule comprising a sequence of SEQ ID NO: 1, 3, 5, 7, 9, 11 or 13, and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11 or 13, and (III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11 or 13, and (IV) a nucleic acid molecule encoding a polypeptide of SEQ ID NO: 2, 4, 6, 8, 10, 12, or 14 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, or 14 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the n-BA forming activity as the polypeptide having SEQ ID NO: 2, 4, 6, 8, 10, 12, or 14.

n-BA forming activity may be quantified by an assay as described in (Fikri E. L. Yahyaoui 2002).

A further embodiment of the invention is a recombinant microorganism comprising an introduced, increased or enhanced activity and/or expression of a nucleic acid molecule encoding an AAT gene encoding an AAT enzyme having an n-BA forming activity.

Preferably, said recombinant microorganism is further comprising a butanol producing pathway and an acryloyl-CoA producing pathway. More preferably, the nucleic acid molecule encoding an AAT gene encoding an AAT enzyme having an n-BA forming activity that is having an introduced, increased or enhanced activity and/or expression in the recombinant microorganism of the invention is selected from the group consisting of (I) a nucleic acid molecule comprising a sequence of SEQ ID NO: 1, 3, 5, 7, 9, 11 or 13, and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11 or 13, and (III) a nucleic acid molecule hybridizing under medium stringent conditions, more preferably under high stringent conditions, most preferably under very high stringent conditions to the complement of a nucleic acid molecule having SEQ ID NO: 1, 3, 5, 7, 9, 11 or 13, and (IV) a nucleic acid molecule encoding a polypeptide of SEQ ID NO: 2, 4, 6, 8, 10, 12, or 14 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, or 14 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the n-BA forming activity as the polypeptide having SEQ ID NO: 2, 4, 6, 8, 10, 12, or 14.

In one embodiment the n-BA forming recombinant microorganism of the invention is selected from the group of prokaryotic microorganisms comprising, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Clostridium propionicum, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavo-*

*bacterium meningosepticum, Lactobacillus* spp., *Micrococcus* sp. CCM825, *Morganella morganii, Nocardia opaca, Nocardia rugosa, Pantoea agglomerans, Planococcus eucinatus, Proteus rettgeri, Propionibacterium shermanii, Pseudomonas synxantha, Pseudomonas azotoformans, Pseudomonas jluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus coagulans, Escherichia freundii, Microbacterium ammoniaphilum, Serratia marcescens, Salmonella typhimurium, Salmonella schottmulleri, Xanthomonas citri, Synechocystis* sp., *Synechococcus elongatus, Thermosynechococcus elongatus, Microcystis aeruginosa, Nostoc* sp., *N. commune, N. sphaericum, Nostoc punctiforme, Spirulina platensis, Lyngbya majuscula, L. lagerheimii, Phormidium tenue, Anabaena* sp., *Leptolyngbya* sp, *Zymomonas mobilis* and so forth.

In another embodiment of the invention, the microorganism is a eukaryotic cell. Suitable eukaryotic cells include yeast cells, as for example *Saccharomyces* spec, such as *Saccharomyces cerevisiae, Hansenula* spec, such as *Hansenula polymorpha, Schizosaccharomyces* spec, such as *Schizosaccharomyces pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris, Zygosaccharomyces* spec, such as *Zygosaccharomyces rouxii* and *Zygosaccharomyces bailii, Candida* spec, such as *Candida boidinii, Candida utilis, Candida freyschussii, Candida glabrata* and *Candida sonorensis, Schwanniomyces* spec, such as *Schwanniomyces occidentalis, Arxula* spec, such as *Arxula adeninivorans, Ogataea* spec such as *Ogataea minuta, Klebsiella* spec, such as *Klebsiella pneumonia* or *Trichosporon* spp., *Yamadazyma* spp. or *Pseudozyma* spp.

Preferably, the microorganism is a yeast of the genus *Saccharomyces* spec, most preferably *Saccharomyces cerevisiae* TYC-072 [MATa; ura3-52; trp1-289; leu2-3_112; his3 Δ1; MAL2-8C; SUC2 adh1::IoxP adh3::IoxP; adh4Δ::IoxP, adh5Δ::IoxP Δadh1,3,4,5 (all with IoxP)].

A further embodiment of the invention is a composition comprising one or more recombinant n-BA forming microorganisms of the invention as defined above. The composition may further comprise a medium that allows grow of the recombinant microorganism of the invention. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. (Steen, Chan et al. 2008, Krivoruchko, Serrano-Amatriain et al. 2013, Tang, Feng et al. 2013). Preferably the carbon source is glucose or sucrose, more preferably the carbon source is glucose.

A further embodiment of the invention is a method for producing a recombinant microorganism producing n-BA comprising the steps of:
(I) introducing, increasing or enhancing the activity and/or expression of an AAT gene encoding an AAT enzyme having an n-BA forming activity in a microorganism; and
(II) further introducing in the microorganism a butanol producing pathway and an acryloyl-CoA producing pathway.

Introducing a butanol or an acryloyl-CoA producing pathway means introducing into the recombinant microorganism all enzymes necessary for catalysing the biochemical reactions to form butanol or acryloyl-CoA respectively, from other metabolite(s).

The AAT gene that is introduced, increased or enhanced in the recombinant microorganism used in the method for producing a recombinant microorganism producing n-BA is selected from the group consisting of
(I) a nucleic acid molecule comprising a sequence of SEQ ID NO: 1, 3, 5, 7, 9, 11 or 13, and
(II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11 or 13, and
(III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11 or 13, and
(IV) a nucleic acid molecule encoding a polypeptide of SEQ ID NO: 2, 4, 6, 8, 10, 12, or 14 or a functional fragment thereof, and
(V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, or 14 or a functional fragment thereof,
wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the n-BA forming activity as the polypeptide having SEQ ID NO: 2, 4, 6, 8, 10, 12, or 14.

The microorganism may be selected from the group of microorganisms as defined above.

A further embodiment of the invention is a recombinant expression construct or a recombinant vector comprising said recombinant expression construct wherein the recombinant expression construct is comprising a promoter functional in a microorganism functionally linked to a nucleic acid molecule having a sequence selected from the group consisting of
(I) a nucleic acid molecule comprising a sequence of SEQ ID NO: 1, 3, 5, 7, 9, 11 or 13, and
(II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11 or 13, and (III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11 or 13, and
(IV) a nucleic acid molecule encoding a polypeptide of SEQ ID NO: 2, 4, 6, 8, 10, 12, or 14 or a functional fragment thereof, and
(V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, or 14 or a functional fragment thereof,
wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the n-BA forming activity as the polypeptide having SEQ ID NO: 2, 4, 6, 8, 10, 12, or 14 and wherein the promoter is heterologous to said nucleic acid molecule.

A further embodiment of the invention is a method of culturing or growing the n-BA forming recombinant microorganism of the invention comprising the steps of inoculating a culture medium with one or more recombinant microorganism of the invention and culturing or growing said recombinant microorganism in culture medium. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. Preferably the carbon source is glucose or sucrose, more preferably the carbon source is glucose.

In some embodiments, the n-BA forming recombinant microorganisms encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation which also finds use in the present invention is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out in a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. In a preferred embodiment the temperature is about 28° C., 30° C. or 32° C. In a most preferred embodiment the temperature is about 28° C. or 30° C.

In some other embodiments, the fermentation is carried out for a period of time within the range of from about 8 hours to 240 hours, from about 8 hours to about 168 hours, from about 10 hours to about 144 hours, from about 15 hours to about 120 hours, or from about 20 hours to about 72 hours. Preferably the fermentation is carried out from about 20 hours to about 40 hours.

In some other embodiments, the fermentation is carried out at a pH in the range of about 4 to about 9, in the range of about 4.5 to about 8.5, in the range of about 5 to about 8, or in the range of about 5.5 to about 7.5. Preferably the fermentation will be carried out at a pH of 5-6.

In one embodiment of the method of producing n-BA, the microorganism is cultured in a medium comprising between 1% and 30% (w/v) of a sugar, between 5% and 25% (w/v) of a sugar, between 10% and 20% (w/v) of a sugar, between 14% and 18% (w/v) of a sugar. Preferably the microorganism is cultured in a medium comprising between 15% and 20% (w/v) of a sugar.

A use of a n-BA forming recombinant microorganism of the invention or a composition of the invention for the fermentative production of n-BA is an additional embodiment of the invention. A further embodiment of the invention is a process for fermentative production of n-BA comprising the steps of
I) growing the n-BA forming microorganism as defined above in a fermenter and
II) recovering n-BA from the fermentation broth obtained in I).

A further embodiment of the invention is a method for fermentative production of butyl propionate comprising the steps of
i) providing a recombinant microorganism comprising a butanol producing pathway, an propionyl-CoA producing pathway and expressing an AAT gene encoding an AAT enzyme having an butyl propionate forming activity and
ii) culturing said microorganism under conditions that allow for the production of butyl propionate and
iii) recovering butyl propionate from the fermentation broth.

The term AAT enzyme or AAT enzyme activity means an enzyme or an enzyme activity as defined by EC 2.3.1.84, catalysing an esterification step, transferring an acyl-CoA to an alcohol. An AAT enzyme having a butyl propionate forming activity means an AAT enzyme catalysing the reaction of propionyl-CoA and butanol to butyl propionate and CoA. The AAT enzyme may be endogenous or heterologous to the microorganism.

A "butanol producing pathway" means a metabolic pathway comprising all enzymes catalysing the biochemical reactions to form butanol from other metabolite(s). Such pathways have previously been established in microorganisms as for example described in (Schadeweg and Boles 2016).

A "propionyl-CoA producing pathway" means a metabolic pathway comprising all enzymes catalyzing the biochemical reactions to form propionyl-CoA from other metabolite(s). Such pathways have previously been established in microorganisms as for example described in (Yuzawa, Chiba et al. 2012).

Another embodiment of the invention is a method for fermentative production of butyl propionate wherein the AAT gene encoding an AAT enzyme having a butyl propionate forming activity is selected from the group consisting of
(I) a nucleic acid molecule comprising a sequence of SEQ ID NO: 1, 3, 5, 7, 9, 11, 13, 15, 17, 19, 21, 23 or 25, and
(II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11, 13, 15, 17, 19, 21, 23 or 25, and
(III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11, 13, 15, 17, 19, 21, 23 or 25, and
(IV) a nucleic acid molecule encoding a polypeptide of SEQ ID NO: 2, 4, 6, 8, 10, 12, 14, 16, 18, 20, 22, 24 or 26 or a functional fragment thereof, and
(V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, 14, 16, 18, 20, 22, 24 or 26 or a functional fragment thereof,
wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl propionate forming activity as the polypeptide having SEQ ID NO: 2, 4, 6, 8, 10, 12, 14, 16, 18, 20, 22, 24 or 26.

Butyl propionate forming activity may be quantified by an assay as described in (Fikri E. L. Yahyaoui 2002).

A further embodiment of the invention is a butyl propionate forming recombinant microorganism comprising an introduced, increased or enhanced activity and/or expression of a nucleic acid molecule encoding an AAT gene encoding an AAT enzyme having a butyl propionate forming activity. Preferably, said recombinant microorganism is further comprising a butanol producing pathway and an propionyl-CoA producing pathway. More preferably, the nucleic acid molecule encoding an AAT gene encoding an AAT enzyme having a butyl propionate forming activity that is having an introduced, increased or enhanced activity and/or expression in the recombinant microorganism of the invention is selected from the group consisting of
(I) a nucleic acid molecule comprising a sequence of SEQ ID NO: 1, 3, 5, 7, 9, 11, 13, 15, 17, 19, 21, 23 or 25, and
(II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11, 13, 15, 17, 19, 21, 23 or 25, and
(III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11, 13, 15, 17, 19, 21, 23 or 25, and
(IV) a nucleic acid molecule encoding a polypeptide of SEQ ID NO: 2, 4, 6, 8, 10, 12, 14, 16, 18, 20, 22, 24 or 26 or a functional fragment thereof, and
(V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, 14, 16, 18, 20, 22, 24 or 26 or a functional fragment thereof,
wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl propionate forming activity as the polypeptide having SEQ ID NO: 2, 4, 6, 8, 10, 12, 14, 16, 18, 20, 22, 24 or 26,
wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl propionate forming activity as the polypeptide having SEQ ID NO: 2, 4, 6, 8, 10, 12, 14, 16, 18, 20, 22, 24 or 26.

In one embodiment the butyl propionate forming recombinant microorganism of the invention is selected from the group of prokaryotic microorganisms comprising, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Clostridium propionicum, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Lactobacillus* spp., *Micrococcus* sp. CCM825, *Morganella morganii, Nocardia opaca, Nocardia rugosa, Pantoea agglomerans, Planococcus eucinatus, Proteus rettgeri, Propionibacterium shermanii, Pseudomonas synxantha, Pseudomonas azotoformans, Pseudomonas jluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coeli-* color, *Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus coagulans, Escherichia freundii, Microbacterium ammoniaphilum, Serratia marcescens, Salmonella typhimurium, Salmonella schottmulleri, Xanthomonas citri, Synechocystis* sp., *Synechococcus elongatus, Thermosynechococcus elongatus, Microcystis aeruginosa, Nostoc* sp., *N. commune, N. spaericum, Nostoc punctiforme, Spirulina platensis, Lyngbya majuscula, L. lagerheimii, Phormidium tenue, Anabaena* sp., *Leptolyngbya* sp, *Zymomonas mobilis* and so forth.

In another embodiment of the invention, the microorganism is a eukaryotic cell. Suitable eukaryotic cells include yeast cells, as for example *Saccharomyces* spec, such as *Saccharomyces cerevisiae, Hansenula* spec, such as *Hansenula polymorpha, Schizosaccharomyces* spec, such as *Schizosaccharomyces pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris, Zygosaccharomyces* spec, such as *Zygosaccharomyces rouxii* and *Zygosaccharomyces bailii, Candida* spec, such as *Candida boidinii, Candida utilis, Candida freyschussii, Candida glabrata* and *Candida sonorensis, Schwanniomyces* spec, such as *Schwanniomyces occidentalis, Arxula* spec, such as *Arxula adeninivorans, Ogataea* spec such as *Ogataea minuta, Klebsiella* spec, such as *Klebsiella pneumonia* or *Trichosporon* spp., *Yamadazyma* spp. or *Pseudozyma* spp.

Preferably, the microorganism is a yeast of the genus *Saccharomyces* spec, most preferably *Saccharomyces cerevisiae* TYC-072 [MATa; ura3-52; trp1-289; leu2-3_112; his3 Δ1; MAL2-8C; SUC2 adh1::IoxP adh3::IoxP; adh4Δ:: IoxP, adh5Δ:IoxP Δadh1,3,4,5 (all with IoxP)].

A further embodiment of the invention is a composition comprising one or more recombinant butyl propionate forming microorganisms of the invention. The composition may further comprise a medium that allows grow of the recombinant microorganism of the invention. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. (Steen, Chan et al. 2008, Krivoruchko, Serrano-Amatriain et al. 2013, Tang, Feng et al. 2013). Preferably the carbon source is glucose or sucrose, more preferably the carbon source is glucose.

A further embodiment of the invention is a method for producing a recombinant microorganism producing butyl propionate comprising the steps of:
(I) introducing, increasing or enhancing the activity and/or expression of an AAT gene encoding an AAT enzyme having an butyl propionate forming activity in a microorganism; and
(II) further introducing in the microorganism a butanol producing pathway and an propionyl-CoA producing pathway.

Introducing a butanol or a propionyl-CoA producing pathway means introducing into the recombinant microorganism all enzymes necessary for catalysing the biochemical reactions to form butanol or propionyl-CoA respectively, from other metabolite(s).

The AAT gene that is introduced, increased or enhanced in the recombinant microorganism used in the method for producing a recombinant microorganism producing butyl propionate is selected from the group consisting of
(I) a nucleic acid molecule comprising a sequence of SEQ ID NO: 1, 3, 5, 7, 9, 11, 13, 15, 17, 19, 21, 23 or 25, and
(II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11, 13, 15, 17, 19, 21, 23 or 25, and
(III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11, 13, 15, 17, 19, 21, 23 or 25, and
(IV) a nucleic acid molecule encoding a polypeptide of SEQ ID NO: 2, 4, 6, 8, 10, 12, 14, 16, 18, 20, 22, 24 or 26 or a functional fragment thereof, and
(V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, 14, 16, 18, 20, 22, 24 or 26 or a functional fragment thereof,
wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl propionate forming activity as the polypeptide having SEQ ID NO: 2, 4, 6, 8, 10, 12, 14, 16, 18, 20, 22, 24 or 26,
wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl propionate forming activity as the polypeptide having SEQ ID NO: 2, 4, 6, 8, 10, 12, 14, 16, 18, 20, 22, 24 or 26.

The microorganism may be selected from the group of microorganisms as defined above.

A further embodiment of the invention is a recombinant expression construct or a recombinant vector comprising said recombinant expression construct wherein the recombinant expression construct is comprising a promoter functional in a microorganism functionally linked to a nucleic acid molecule having a sequence selected from the group consisting of
(I) a nucleic acid molecule comprising a sequence of SEQ ID NO: 1, 3, 5, 7, 9, 11, 13, 15, 17, 19, 21, 23 or 25, and
(II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11, 13, 15, 17, 19, 21, 23 or 25, and
(III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11, 13, 15, 17, 19, 21, 23 or 25, and (IV) a nucleic acid molecule encoding a polypeptide of SEQ ID NO: 2, 4, 6, 8, 10, 12, 14, 16, 18, 20, 22, 24 or 26 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, 14, 16, 18, 20, 22, 24 or 26 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl propionate forming activity as the polypeptide having SEQ ID NO: 2, 4, 6, 8, 10, 12, 14, 16, 18, 20, 22, 24 or 26 and wherein the promoter is heterologous to said nucleic acid molecule.

A further embodiment of the invention is a method of culturing or growing the butyl propionate forming recombinant microorganism of the invention comprising the steps of inoculating a culture medium with one or more recombinant microorganism of the invention and culturing or growing said recombinant microorganism in culture medium. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. Preferably the carbon source is glucose or sucrose, more preferably the carbon source is glucose.

In some embodiments, the butyl propionate forming recombinant microorganisms encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation which also finds use in the present invention is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out in a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. In a preferred embodiment the temperature is about 28° C., 30° C. or 32° C. In a most preferred embodiment the temperature is about 28° C. or 30° C.

In some other embodiments, the fermentation is carried out for a period of time within the range of from about 8 hours to 240 hours, from about 8 hours to about 168 hours, from about 10 hours to about 144 hours, from about 15 hours to about 120 hours, or from about 20 hours to about 72 hours. Preferably the fermentation is carried out from about 20 hours to about 40 hours.

In some other embodiments, the fermentation is carried out at a pH in the range of about 4 to about 9, in the range of about 4.5 to about 8.5, in the range of about 5 to about 8, or in the range of about 5.5 to about 7.5. Preferably the fermentation will be carried out at a pH of 5-6.

In one embodiment of the method of producing butyl propionate, the microorganism is cultured in a medium comprising between 1% and 30% (w/v) of a sugar, between 5% and 25% (w/v) of a sugar, between 10% and 20% (w/v) of a sugar, between 14% and 18% (w/v) of a sugar. Preferably the microorganism is cultured in a medium comprising between 15% and 20% (w/v) of a sugar.

A use of a butyl propionate forming recombinant microorganism of the invention or a composition of the invention for the fermentative production of butyl propionate is an additional embodiment of the invention. A further embodiment of the invention is a process for fermentative production of butyl propionate comprising the steps of I) growing the butyl propionate forming microorganism of the invention in a fermenter and II) recovering butyl propionate from the fermentation broth obtained in I).

A further embodiment of the invention is a method for fermentative production of butyl lactate comprising the steps of i) providing a recombinant microorganism comprising a butanol producing pathway, a lactoyl-CoA producing pathway and expressing an AAT gene encoding an AAT enzyme having a butyl lactate forming activity and ii) culturing said microorganism under conditions that allow for the production of butyl lactate and iii) recovering butyl lactate from the fermentation broth.

The term AAT enzyme or AAT enzyme activity means an enzyme or an enzyme activity as defined by EC 2.3.1.84, catalysing an esterification step, transferring an acyl-CoA to an alcohol. An AAT enzyme having a butyl lactate forming activity means an AAT enzyme catalysing the reaction of lactoyl-CoA and butanol to butyl lactate and CoA. The AAT enzyme may be endogenous or heterologous to the microorganism.

A "butanol producing pathway" means a metabolic pathway comprising all enzymes catalysing the biochemical reactions to form butanol from other metabolite(s). Such pathways have previously been established in microorganisms as for example described in (Schadeweg and Boles 2016).

A "lactoyl-CoA producing pathway" means a metabolic pathway comprising all enzymes catalyzing the biochemical reactions to form lactoyl-CoA from other metabolite(s). Such pathways have previously been established in microorganisms as for example described in (Nevoigt 2008).

Another embodiment of the invention is a method for fermentative production of butyl lactate wherein the AAT gene encoding an AAT enzyme having a butyl lactate forming activity is selected from the group consisting of (I) a nucleic acid molecule comprising a sequence of SEQ ID NO: 1, 3, 5, 7, 9, 15, 17 or 19 and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 15, 17 or 19, and (III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 15, 17 or 19, and (IV) a nucleic acid molecule encoding a polypeptide of SEQ ID NO: 2, 4, 6, 8, 10, 16, 18 or 20 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO:: 2, 4, 6, 8, 10, 16, 18 or 20 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl lactate forming activity as the polypeptide having SEQ ID NO:: 2, 4, 6, 8, 10, 16, 18 or 20.

Butyl lactate forming activity may be quantified by an assay as described in (Fikri E. L. Yahyaoui 2002).

A further embodiment of the invention is a butyl lactate forming recombinant microorganism comprising an introduced, increased or enhanced activity and/or expression of a nucleic acid molecule encoding an AAT gene encoding an AAT enzyme having a butyl lactate forming activity. Preferably, said recombinant microorganism is further comprising a butanol producing pathway and a lactoyl-CoA producing pathway. More preferably, the nucleic acid molecule encoding an AAT gene encoding an AAT enzyme having a butyl lactate forming activity that is having an introduced, increased or enhanced activity and/or expression in the recombinant microorganism of the invention is selected from the group consisting of (I) a nucleic acid molecule comprising a sequence of SEQ ID NO: 1, 3, 5, 7, 9, 15, 17 or 19 and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 15, 17 or 19, and (III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 15, 17 or 19, and (IV) a nucleic acid molecule encoding a polypeptide of SEQ ID NO: 2, 4, 6, 8, 10, 16, 18 or 20 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 16, 18 or 20 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl lactate forming activity as the polypeptide having SEQ ID NO: 2, 4, 6, 8, 10, 16, 18 or 20.

In one embodiment the butyl lactate forming recombinant microorganism of the invention is selected from the group of prokaryotic microorganisms comprising, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Clostridium propionicum, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Lactobacillus spp., Micrococcus sp. CCM825, Morganella morganii, Nocardia opaca, Nocardia rugosa, Pantoea agglomerans, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus coagulans, Escherichia freundii, Microbacterium ammoniaphilum, Serratia marcescens, Salmonella typhimurium, Salmonella schottmulleri, Xanthomonas citri, Synechocystis* sp., *Synechococcus elongatus, Thermosynechococcus elongatus, Microcystis aeruginosa, Nostoc* sp., *N. commune, N. spaericum, Nostoc punctiforme, Spirulina platensis, Lyngbya majuscula, L. lagerheimii, Phormidium tenue, Anabaena* sp., *Leptolyngbya* sp, *Zymomonas mobilis* and so forth.

In another embodiment of the invention, the microorganism is a eukaryotic cell. Suitable eukaryotic cells include yeast cells, as for example *Saccharomyces* spec, such as *Saccharomyces cerevisiae, Hansenula* spec, such as *Han-*

*senula polymorpha, Schizosaccharomyces* spec, such as *Schizosaccharomyces pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris, Zygosaccharomyces* spec, such as *Zygosaccharomyces rouxii* and *Zygosaccharomyces bailii, Candida* spec, such as *Candida boidinii, Candida utilis, Candida freyschussii, Candida glabrata* and *Candida sonorensis, Schwanniomyces* spec, such as *Schwanniomyces occidentalis, Arxula* spec, such as *Arxula adeninivorans, Ogataea* spec such as *Ogataea minuta, Klebsiella* spec, such as *Klebsiella pneumonia* or *Trichosporon* spp., *Yamadazyma* spp. or *Pseudozyma* spp.

Preferably, the microorganism is a yeast of the genus *Saccharomyces* spec, most preferably *Saccharomyces cerevisiae* TYC-072 [MATa; ura3-52; trp1-289; leu2-3_112; his3 Δ1; MAL2-8C; SUC2 adh1::loxP adh3::loxP; adh4Δ::loxP, adh5Δ::loxP Δadh 1,3,4,5 (all with loxP)].

A further embodiment of the invention is a composition comprising one or more recombinant butyl lactate forming microorganisms of the invention. The composition may further comprise a medium that allows grow of the recombinant microorganism of the invention. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. (Steen, Chan et al. 2008, Krivoruchko, Serrano-Amatriain et al. 2013, Tang, Feng et al. 2013). Preferably the carbon source is glucose or sucrose, more preferably the carbon source is glucose.

A further embodiment of the invention is a method for producing a recombinant microorganism producing butyl lactate comprising the steps of:
  (I) introducing, increasing or enhancing the activity and/or expression of an AAT gene encoding an AAT enzyme having a butyl lactate forming activity in a microorganism; and
  (II) further introducing in the microorganism a butanol producing pathway and a lactoyl-CoA producing pathway.

Introducing a butanol or a lactoyl-CoA producing pathway means introducing into the recombinant microorganism all enzymes necessary for catalysing the biochemical reactions to form butanol or lactoyl-CoA respectively, from other metabolite(s).

The AAT gene that is introduced, increased or enhanced in the recombinant microorganism used in the method for producing a recombinant microorganism producing butyl lactate is selected from the group consisting of
  (I) a nucleic acid molecule comprising a sequence of SEQ ID NO: 1, 3, 5, 7, 9, 15, 17 or 19 and
  (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 15, 17 or 19, and
  (III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 15, 17 or 19, and
  (IV) a nucleic acid molecule encoding a polypeptide of SEQ ID NO: 2, 4, 6, 8, 10, 16, 18 or 20 or a functional fragment thereof, and
  (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 16, 18 or 20 or a functional fragment thereof,
  wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl lactate forming activity as the polypeptide having SEQ ID NO: 2, 4, 6, 8, 10, 16, 18 or 20.

The microorganism may be selected from the group of microorganisms as defined above.

A further embodiment of the invention is a recombinant expression construct or a recombinant vector comprising said recombinant expression construct wherein the recombinant expression construct is comprising a promoter functional in a microorganism functionally linked to a nucleic acid molecule having a sequence selected from the group consisting of
  (I) a nucleic acid molecule comprising a sequence of SEQ ID NO: 1, 3, 5, 7, 9, 15, 17 or 19 and
  (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 15, 17 or 19, and
  (III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 15, 17 or 19, and
  (IV) a nucleic acid molecule encoding a polypeptide of SEQ ID NO: 2, 4, 6, 8, 10, 16, 18 or 20 or a functional fragment thereof, and
  (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 16, 18 or 20 or a functional fragment thereof,
  wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl lactate forming activity as the polypeptide having SEQ ID NO: 2, 4, 6, 8, 10, 16, 18 or 20 and wherein the promoter is heterologous to said nucleic acid molecule.

A further embodiment of the invention is a method of culturing or growing the butyl lactate forming recombinant microorganism of the invention comprising the steps of inoculating a culture medium with one or more recombinant microorganism of the invention and culturing or growing said recombinant microorganism in culture medium. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. Preferably the carbon source is glucose or sucrose, more preferably the carbon source is glucose.

In some embodiments, the butyl lactate forming recombinant microorganisms encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation which also finds use in the present invention is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out in a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. In a preferred embodiment the temperature is about 28° C., 30° C. or 32° C. In a most preferred embodiment the temperature is about 28° C. or 30° C.

In some other embodiments, the fermentation is carried out for a period of time within the range of from about 8 hours to 240 hours, from about 8 hours to about 168 hours, from about 10 hours to about 144 hours, from about 15 hours to about 120 hours, or from about 20 hours to about 72 hours. Preferably the fermentation is carried out from about 20 hours to about 40 hours.

In some other embodiments, the fermentation is carried out at a pH in the range of about 4 to about 9, in the range of about 4.5 to about 8.5, in the range of about 5 to about 8, or in the range of about 5.5 to about 7.5. Preferably the fermentation will be carried out at a pH of 5-6.

In one embodiment of the method of producing butyl lactate, the microorganism is cultured in a medium comprising between 1% and 30% (w/v) of a sugar, between 5% and 25% (w/v) of a sugar, between 10% and 20% (w/v) of a sugar, between 14% and 18% (w/v) of a sugar. Preferably the microorganism is cultured in a medium comprising between 15% and 20% (w/v) of a sugar.

A use of a butyl lactate forming recombinant microorganism of the invention or a composition of the invention for the fermentative production of butyl lactate is an additional embodiment of the invention. A further embodiment of the invention is a process for fermentative production of butyl lactate comprising the steps of
I) growing the butyl lactate forming microorganism of the invention in a fermenter and
II) recovering butyl lactate from the fermentation broth obtained in I).

A further embodiment of the invention is a method for fermentative production of ethyl acetate comprising the steps of
i) providing a recombinant microorganism comprising an ethanol producing pathway, an acetyl-CoA producing pathway and expressing an AAT gene encoding an AAT enzyme having an ethyl acetate forming activity and
ii) culturing said microorganism under conditions that allow for the production of ethyl acetate and
iii) recovering ethyl acetate from the fermentation broth.

The term AAT enzyme or AAT enzyme activity means an enzyme or an enzyme activity as defined by EC 2.3.1.84, catalysing an esterification step, transferring an acyl-CoA to an alcohol. An AAT enzyme having an ethyl acetate forming activity means an AAT enzyme catalysing the reaction of acetyl-CoA and ethanol to ethyl acetate and CoA. The AAT enzyme may be endogenous or heterologous to the microorganism.

An "ethanol producing pathway" means a metabolic pathway comprising all enzymes catalysing the biochemical reactions to form ethanol from other metabolite(s). Such pathways have previously been established in microorganisms (Oeser, 2015, *Yeast*, 32(1)).

An "acetyl-CoA producing pathway" means a metabolic pathway comprising all enzymes catalyzing the biochemical reactions to form acetyl-CoA from other metabolite(s). Such pathways have previously been established in microorganisms (Schadeweg, V. and E. Boles, 2016, BIOTECHNOLOGY FOR BIOFUELS (9)).

Another embodiment of the invention is a method for fermentative production of ethyl acetate wherein the AAT gene encoding an AAT enzyme having an ethyl acetate forming activity is selected from the group consisting of
(I) a nucleic acid molecule comprising a sequence of SEQ ID NO: 3, 5, 7, 9, 11, 13, 15, 17, 19, 21, 23, 25 or 27, and
(II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 3, 5, 7, 9, 11, 13, 15, 17, 19, 21, 23, 25 or 27, and
(III) a nucleic acid molecule hybridizing under medium stringent conditions, preferably under high stringent conditions, more preferably under very high stringent conditions to the complement of a nucleic acid molecule having SEQ ID NO: 3, 5, 7, 9, 11, 13, 15, 17, 19, 21, 23, 25 or 27, and
(IV) a nucleic acid molecule encoding a polypeptide of SEQ ID NO: 4, 6, 8, 10, 12, 14, 16, 18, 20, 22, 24, 26 or 28 or a functional fragment thereof, and
(V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 4, 6, 8, 10, 12, 14, 16, 18, 20, 22, 24, 26 or 28 or a functional fragment thereof,
wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the ethyl acetate forming activity as the polypeptide having SEQ ID NO: 4, 6, 8, 10, 12, 14, 16, 18, 20, 22, 24, 26 or 28.

Ethyl acetate forming activity may be quantified by an assay as described in (Fikri E. L. Yahyaoui 2002).

A further embodiment of the invention is an ethyl acetate forming recombinant microorganism comprising an introduced, increased or enhanced activity and/or expression of a nucleic acid molecule encoding an AAT gene encoding an AAT enzyme having an ethyl acetate forming activity. Preferably, said recombinant microorganism is further comprising an ethanol producing pathway and a ethyl-CoA producing pathway. More preferably, the nucleic acid molecule encoding an AAT gene encoding an AAT enzyme having an ethyl acetate forming activity that is having an introduced, increased or enhanced activity and/or expression in the recombinant microorganism of the invention is selected from the group consisting of (I) a nucleic acid molecule comprising a sequence of SEQ ID NO: 3, 5, 7, 9, 11, 13, 15, 17, 19, 21, 23, 25 or 27, and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 3, 5, 7, 9, 11, 13, 15, 17, 19, 21, 23, 25 or 27, and (III) a nucleic acid molecule hybridizing under medium stringent conditions, preferably under high stringent conditions, more preferably under very high stringent conditions to the complement of a nucleic acid molecule having SEQ ID NO: 3, 5, 7, 9, 11, 13, 15, 17, 19, 21, 23, 25 or 27, and (IV) a nucleic acid molecule encoding a polypeptide of SEQ ID NO: 4, 6, 8, 10, 12, 14, 16, 18, 20, 22, 24, 26 or 28 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 4, 6, 8, 10, 12, 14, 16, 18, 20, 22, 24, 26 or 28 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the ethyl acetate forming activity as the polypeptide having SEQ ID NO: 4, 6, 8, 10, 12, 14, 16, 18, 20, 22, 24, 26 or 28.

In one embodiment the ethyl acetate forming recombinant microorganism of the invention is selected from the group of prokaryotic microorganisms comprising, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Clostridium propionicum, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Lactobacillus* spp., *Micrococcus* sp. CCM825, *Morganella morganii, Nocardia opaca, Nocardia rugosa, Pantoea agglomerans, Planococcus eucinatus, Proteus rettgeri, Propionibacterium shermanii, Pseudomonas synxantha, Pseudomonas azotoformans, Pseudomonas jluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus coagulans, Escherichia freundii, Microbacterium ammoniaphilum, Serratia marcescens, Salmonella typhimurium, Salmonella schottmulleri, Xanthomonas citri, Synechocystis* sp., *Synechococcus elongatus, Thermosynechococcus elongatus, Microcystis aeruginosa, Nostoc* sp., *N. commune, N. sphaericum, Nostoc punctiforme, Spirulina platensis, Lyngbya majuscula, L. lagerheimii, Phormidium tenue, Anabaena* sp., *Leptolyngbya* sp, *Zymomonas mobilis* and so forth.

In another embodiment of the invention, the microorganism is a eukaryotic cell. Suitable eukaryotic cells include yeast cells, as for example *Saccharomyces* spec, such as *Saccharomyces cerevisiae, Hansenula* spec, such as *Hansenula polymorpha, Schizosaccharomyces* spec, such as *Schizosaccharomyces pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris, Zygosaccharomyces* spec, such as *Zygosaccharomyces rouxii* and *Zygosaccharomyces bailii, Candida* spec, such as *Candida boidinii, Candida utilis, Candida freyschussii, Candida glabrata* and *Candida sonorensis, Schwanniomyces* spec, such as *Schwanniomyces occidentalis, Arxula* spec, such as *Arxula adeninivorans, Ogataea* spec such as *Ogataea minuta, Klebsiella* spec, such as *Klebsiella pneumonia* or *Trichosporon* spp., *Yamadazyma* spp. or *Pseudozyma* spp.

Preferably, the microorganism is a yeast of the genus *Saccharomyces* spec, most preferably *Saccharomyces cerevisiae* TYC-072 [MATa; ura3-52; trp1-289; leu2-3_112; his3 Δ1; MAL2-8C; SUC2 adh1::IoxP adh3::IoxP; adh4Δ:: IoxP, adh5Δ::IoxP Δadh1,3,4,5 (all with IoxP)].

A further embodiment of the invention is a composition comprising one or more recombinant ethyl acetate forming microorganisms of the invention. The composition may further comprise a medium that allows grow of the recombinant microorganism of the invention. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. (Steen, Chan et al. 2008, Krivoruchko, Serrano-Amatriain et al. 2013, Tang, Feng et al. 2013). Preferably the carbon source is glucose or sucrose, more preferably the carbon source is glucose.

A further embodiment of the invention is a method for producing a recombinant microorganism producing ethyl acetate comprising the steps of:
  (I) introducing, increasing or enhancing the activity and/or expression of an AAT gene encoding an AAT enzyme having an ethyl acetate forming activity in a microorganism; and
  (II) further introducing in the microorganism an ethanol producing pathway and an acetyl-CoA producing pathway.

Introducing an ethanol or an acetyl-CoA producing pathway means introducing into the recombinant microorganism all enzymes necessary for catalysing the biochemical reactions to form ethanol or acetyl-CoA respectively, from other metabolite(s).

The AAT gene that is introduced, increased or enhanced in the recombinant microorganism used in the method for producing a recombinant microorganism producing ethyl acetate is selected from the group consisting of
  (I) a nucleic acid molecule comprising a sequence of SEQ ID NO: 3, 5, 7, 9, 11, 13, 15, 17, 19, 21, 23, 25 or 27, and
  (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 3, 5, 7, 9, 11, 13, 15, 17, 19, 21, 23, 25 or 27, and
  (III) a nucleic acid molecule hybridizing under medium stringent conditions, preferably under high stringent conditions, more preferably under very high stringent conditions to the complement of a nucleic acid molecule having SEQ ID NO: 3, 5, 7, 9, 11, 13, 15, 17, 19, 21, 23, 25 or 27, and
  (IV) a nucleic acid molecule encoding a polypeptide of SEQ ID NO: 4, 6, 8, 10, 12, 14, 16, 18, 20, 22, 24, 26 or 28 or a functional fragment thereof, and
  (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 4, 6, 8, 10, 12, 14, 16, 18, 20, 22, 24, 26 or 28 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the ethyl acetate forming activity as the polypeptide having SEQ ID NO: 4, 6, 8, 10, 12, 14, 16, 18, 20, 22, 24, 26 or 28.

The microorganism may be selected from the group of microorganisms as defined above.

A further embodiment of the invention is a recombinant expression construct or a recombinant vector comprising said recombinant expression construct wherein the recombinant expression construct is comprising a promoter functional in a microorganism functionally linked to a nucleic acid molecule having a sequence selected from the group consisting of
  (I) a nucleic acid molecule comprising a sequence of SEQ ID NO: 3, 5, 7, 9, 11, 13, 15, 17, 19, 21, 23, 25 or 27, and
  (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 3, 5, 7, 9, 11, 13, 15, 17, 19, 21, 23, 25 or 27, and
  (III) a nucleic acid molecule hybridizing under medium stringent conditions, preferably under high stringent conditions, more preferably under very high stringent conditions to the complement of a nucleic acid molecule having SEQ ID NO: 3, 5, 7, 9, 11, 13, 15, 17, 19, 21, 23, 25 or 27, and
  (IV) a nucleic acid molecule encoding a polypeptide of SEQ ID NO: 4, 6, 8, 10, 12, 14, 16, 18, 20, 22, 24, 26 or 28 or a functional fragment thereof, and
  (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 4, 6, 8, 10, 12, 14, 16, 18, 20, 22, 24, 26 or 28 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the ethyl acetate forming activity as the polypeptide having SEQ ID NO: 4, 6, 8, 10, 12, 14, 16, 18, 20, 22, 24, 26 or 28 and wherein the promoter is heterologous to said nucleic acid molecule.

A further embodiment of the invention is a method of culturing or growing the ethyl acetate forming recombinant microorganism of the invention comprising the steps of inoculating a culture medium with one or more recombinant microorganism of the invention and culturing or growing said recombinant microorganism in culture medium. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. Preferably the carbon source is glucose or sucrose, more preferably the carbon source is glucose.

In some embodiments, the ethyl acetate forming recombinant microorganisms encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation which also finds use in the present invention is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out in a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. In a preferred embodiment the temperature is about 28° C., 30° C. or 32° C. In a most preferred embodiment the temperature is about 28° C. or 30° C.

In some other embodiments, the fermentation is carried out for a period of time within the range of from about 8 hours to 240 hours, from about 8 hours to about 168 hours, from about 10 hours to about 144 hours, from about 15 hours to about 120 hours, or from about 20 hours to about 72 hours. Preferably the fermentation is carried out from about 20 hours to about 40 hours.

In some other embodiments, the fermentation is carried out at a pH in the range of about 4 to about 9, in the range of about 4.5 to about 8.5, in the range of about 5 to about 8, or in the range of about 5.5 to about 7.5. Preferably the fermentation will be carried out at a pH of 5-6.

In one embodiment of the method of producing ethyl acetate, the microorganism is cultured in a medium comprising between 1% and 30% (w/v) of a sugar, between 5% and 25% (w/v) of a sugar, between 10% and 20% (w/v) of a sugar, between 14% and 18% (w/v) of a sugar. Preferably the microorganism is cultured in a medium comprising between 15% and 20% (w/v) of a sugar.

A use of an ethyl acetate forming recombinant microorganism of the invention or a composition of the invention for the fermentative production of ethyl acetate is an additional embodiment of the invention. A further embodiment of the invention is a process for fermentative production of ethyl acetate comprising the steps of I) growing the ethyl acetate forming microorganism of the invention in a fermenter and II) recovering ethyl acetate from the fermentation broth obtained in I).

Definitions

It is to be understood that this invention is not limited to the particular methodology or protocols. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine, prokaryotes also use the triplets "GTG" and "TTG" as startcodon. On the 3'-side it is bounded by one of the three triplets which specify stop codons (i.e., TAA, TAG, TGA). In addition a gene may include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Endogenous: An "endogenous" nucleotide sequence refers to a nucleotide sequence, which is present in the genome of a wild type microorganism.

Enhanced expression: "enhance" or "increase" the expression of a nucleic acid molecule in a microorganism are used equivalently herein and mean that the level of expression of a nucleic acid molecule in a microorganism is higher compared to a reference microorganism, for example a wild type. The terms "enhanced" or "increased" as used herein mean herein higher, preferably significantly higher expression of the nucleic acid molecule to be expressed. As used herein, an "enhancement" or "increase" of the level of an agent such as a protein, mRNA or RNA means that the level is increased relative to a substantially identical microorganism grown under substantially identical conditions. As used herein, "enhancement" or "increase" of the level of an agent, such as for example a preRNA, mRNA, rRNA, tRNA, expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a suitable reference microorganism. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, densitometric measurement of nucleic acid concentration in a gel, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a microorganism. Depending on the type of the induced protein product, its activity or the effect on the phenotype of the microorganism may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry OH et al. (1951) J Biol Chem 193:265-275) or measuring the absorption of CBB G-250 (Bradford M M (1976) Analyt Biochem 72:248-254).

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Foreign: The term "foreign" refers to any nucleic acid molecule (e.g., gene sequence) which is introduced into a cell by experimental manipulations and may include sequences found in that cell as long as the introduced sequence contains some modification (e.g., a point mutation, the presence of a selectable marker gene, etc.) and is therefore different relative to the naturally-occurring sequence.

Functional fragment: the term "functional fragment" refers to any nucleic acid and/or protein which comprises merely a part of the full length nucleic acid and/or full length polypeptide of the invention but still provides the same function, i.e. the function of an AAT enzyme catalyzing the reaction of acryloyl-CoA and butanol to n-BA and CoA. Preferably, the fragment comprises at least 50%, at least 60%, at least 70%, at least 80%, at least 90% at least 95%, at least 98%, at least 99% of the sequence from which it is derived. Preferably, the functional fragment comprises contiguous nucleic acids or amino acids of the nucleic acid and/or protein from which the functional fragment is derived. A functional fragment of a nucleic acid molecule encoding a protein means a fragment of the nucleic acid molecule encoding a functional fragment of the protein.

Functional linkage: The term "functional linkage" or "functionally linked" is equivalent to the term "operable linkage" or "operably linked" and is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form or can be inserted into the genome, for example by transformation.

Gene: The term "gene" refers to a region operably linked to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleoid but also the DNA of the self-replicating plasmid.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural genomic locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

Suitable hybridization conditions are for example hybridizing under conditions equivalent to hybridization in 7% sodium dodecyl sulfate (SDS), 0.5 M NaPO4, 1 mM EDTA at 50° C. with washing in 2×SSC, 0.1% SDS at 50° C. (low stringency) to a nucleic acid molecule comprising at least 50, preferably at least 100, more preferably at least 150, even more preferably at least 200, most preferably at least 250 consecutive nucleotides of the complement of a sequence. Other suitable hybridizing conditions are hybridization in 7% sodium dodecyl sulfate (SDS), 0.5 M NaPO4, 1 mM EDTA at 50° C. with washing in 1×SSC, 0.1% SDS at 50° C. (medium stringency) or 65° C. (high stringency) to a nucleic acid molecule comprising at least 50, preferably at least 100, more preferably at least 150, even more preferably at least 200, most preferably at least 250 consecutive nucleotides of a complement of a sequence. Other suitable hybridization conditions are hybridization in 7% sodium dodecyl sulfate (SDS), 0.5 M NaPO4, 1 mM EDTA at 50° C. with washing in 0.1×SSC, 0.1% SDS at 65° C. (very high stringency) to a nucleic acid molecule comprising at least 50, preferably at least 100, more preferably at least 150, even more preferably at least 200, most preferably at least 250 consecutive nucleotides of a complement of a sequence.

"Identity": "Identity" when used in respect to the comparison of two or more nucleic acid or amino acid molecules means that the sequences of said molecules share a certain degree of sequence similarity, the sequences being partially identical. To determine the percentage identity (homology is herein used interchangeably if referring to nucleic acid sequences) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are identical at this position. The percentage identity between the two sequences is a function of the number of identical positions shared by the sequences (i.e. % identity=number of identical positions/total number of positions×100). The terms "homology" and "identity" are thus to be considered as synonyms when referring to nucleic acid sequences. When referring to amino acid sequences the term identity refers to identical amino acids at a specific position in a sequence, the term homology refers to homologous amino acids at a specific position in a sequence. Homologous amino acids are amino acids having a similar side chain. Families of amino acid residues having similar side chains have been defined in the art.

A nucleic acid molecule encoding a protein homologous to a protein of the invention can be created by introducing one or more nucleotide substitutions, additions or deletions into a nucleotide sequence such that one or more amino acid substitutions, additions or deletions are introduced into the encoded protein. Mutations can be introduced into one of the sequences of the invention by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a protein of the invention is preferably replaced with another amino acid residue from the same side chain family.

Alternatively, in another embodiment, mutations can be introduced randomly along all or part of a coding sequence, such as by saturation mutagenesis, and the resultant mutants can be screened for the respective activity described herein to identify mutants that retain their activity. Following mutagenesis of one of the sequences of the invention, the encoded protein can be expressed recombinantly and the activity of the protein can be determined using, for example, assays described herein.

For the determination of the percentage identity of two or more amino acids or of two or more nucleotide sequences several computer software programs have been developed. The identity of two or more sequences can be calculated with for example the software fasta, which presently has been used in the version fasta 3 (W. R. Pearson and D. J. Lipman, PNAS 85, 2444(1988); W. R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of identities of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences:

-p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in deflines [T/F]; default=F; -q Penalty for a nucleotide mismatch (blastn only) [Integer]; default=-3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perfom gapped alignment (not available with tblastx) [T/F]; default=T; -Q Query Genetic code to use [Integer]; default=1; -D DB Genetic code (for tblast [nx] only) [Integer]; default=1; -a Number of processors to use [Integer]; default=1; -O SeqAlign file [File Out] Optional; -J Believe the query defline [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; -I Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wisconsin, USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence identity are done with the programs "Gap" or "Needle" over the whole range of the sequences. The following standard adjustments for the comparison of nucleic acid sequences were used for "Needle": matrix: EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which is said to have 80% identity with sequence SEQ ID NO: 1 at the nucleic acid level is understood as meaning a sequence which, upon comparison with the sequence represented by SEQ ID NO: 1 by the above program "Needle" with the above parameter set, has a 80% identity. Preferably the identity is calculated on the complete length of the query sequence, for example SEQ ID NO:1.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring nucleic acid molecule or polypeptide present in a living cell is not isolated, but the same nucleic acid molecule or polypeptide, separated from some or all of the coexisting materials in the natural system, is isolated. Such nucleic acid molecules can be part of a vector and/or such nucleic acid molecules or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO: 1 where the nucleic acid sequence is in a genomic or plasmid location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Non-coding: The term "non-coding" refers to sequences of nucleic acid molecules that do not encode part or all of an expressed protein. Non-coding sequences include but are not limited enhancers, promoter regions, 3' untranslated regions, and 5' untranslated regions.

Nucleic acids and nucleotides: The terms "nucleic acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "nucleic acid molecule". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Polypeptide: The terms "polypeptide", "peptide", "oligopeptide", "polypeptide", "gene product", "expression product" and "protein" are used interchangeably herein to refer to a polymer or oligomer of consecutive amino acid residues.

Promoter: The terms "promoter", or "promoter sequence" are equivalents and as used herein, refer to a DNA sequence which when operably linked to a nucleotide sequence of interest is capable of controlling the transcription of the nucleotide sequence of interest into RNA. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. The promoter does not comprise coding regions or 5' untranslated regions. The promoter may for example be heterologous or homologous to the respective cell. A nucleic acid molecule sequence is "heterologous to" an organism or a second nucleic acid molecule sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host.

Purified: As used herein, the term "purified" refers to molecules, either nucleic or amino acid sequences that are removed from their natural environment, isolated or separated.

"Substantially purified" molecules are at least 60% free, preferably at least 75% free, and more preferably at least 90% free from other components with which they are naturally associated. A purified nucleic acid sequence may be an isolated nucleic acid sequence.

Significant increase: An increase for example in enzymatic activity, gene expression, productivity or yield of a certain product, that is larger than the margin of error inherent in the measurement technique, preferably an increase by about 10% or 25% preferably by 50% or 75%, more preferably 2-fold or 5 fold or greater of the activity, expression, productivity or yield of the control enzyme or expression in the control cell, productivity or yield of the control cell, even more preferably an increase by about 10-fold or greater.

Significant decrease: A decrease for example in enzymatic activity, gene expression, productivity or yield of a certain product, that is larger than the margin of error inherent in the measurement technique, preferably a decrease by at least about 5% or 10%, preferably by at least about 20% or 25%, more preferably by at least about 50% or 75%, even more preferably by at least about 80% or 85%, most preferably by at least about 90%, 95%, 97%, 98% or 99%.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with at least one recombinant nucleic acid molecule.

Vector: As used herein, the term "vector" refers to a nucleic acid molecule capable of transporting another nucleic acid molecule to which it has been linked. One type of vector is a genomic integrated vector, or "integrated vector", which can become integrated into the genomic DNA of the host cell. Another type of vector is an episomal vector, i.e., a plasmid or a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context.

Wild type: The term "wild type", "natural" or "natural origin" means with respect to an organism that said organism is not changed, mutated, or otherwise manipulated by man. With respect to a polypeptide or nucleic acid sequence, that the polypeptide or nucleic acid sequence is naturally occurring or available in at least one naturally occurring organism which is not changed, mutated, or otherwise manipulated by man.

A wild type of a microorganism refers to a microorganism whose genome is present in a state as before the introduction of a genetic modification of a certain gene. The genetic modification may be e.g. a deletion of a gene or a part thereof or a point mutation or the introduction of a gene.

The terms "production" or "productivity" are art-recognized and include the concentration of the fermentation product (for example, dsRNA) formed within a given time and a given fermentation volume (e.g., kg product per hour per liter). The term "efficiency of production" includes the time required for a particular level of production to be achieved (for example, how long it takes for the cell to attain a particular rate of output of a fine chemical).

The term "yield" or "product/carbon yield" is art-recognized and includes the efficiency of the conversion of the carbon source into the product (i.e., fine chemical). This is generally written as, for example, kg product per kg carbon source. By increasing the yield or production of the compound, the quantity of recovered molecules or of useful recovered molecules of that compound in a given amount of culture over a given amount of time is increased.

The term "recombinant microorganism" includes microorganisms which have been genetically modified such that they exhibit an altered or different genotype and/or phenotype (e. g., when the genetic modification affects coding nucleic acid sequences of the microorganism) as compared to the wild type microorganism from which it was derived. A recombinant microorganism comprises at least one recombinant nucleic acid molecule.

The term "recombinant" with respect to nucleic acid molecules refers to nucleic acid molecules produced by man using recombinant nucleic acid techniques. The term comprises nucleic acid molecules which as such do not exist in nature or do not exist in the organism from which the nucleic acid molecule is derived, but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecules" may also comprise a "recombinant construct" which comprises, preferably operably linked, a sequence of nucleic acid molecules not naturally occurring in that order. Preferred methods for producing said recombinant nucleic acid molecules may comprise cloning techniques, directed or non-directed mutagenesis, gene synthesis or recombination techniques.

An example of such a recombinant nucleic acid molecule is a plasmid into which a heterologous DNA-sequence has been inserted or a gene or promoter which has been mutated compared to the gene or promoter from which the recombinant nucleic acid molecule derived. The mutation may be introduced by means of directed mutagenesis technologies known in the art or by random mutagenesis technologies such as chemical, UV light or x-ray mutagenesis or directed evolution technologies.

The term "directed evolution" is used synonymously with the term "metabolic evolution" herein and involves applying a selection pressure that favors the growth of mutants with the traits of interest. The selection pressure can be based on different culture conditions, ATP and growth coupled selection and redox related selection. The selection pressure can be carried out with batch fermentation with serial transferring inoculation or continuous culture with the same pressure.

The term "expression" or "gene expression" means the transcription of a specific gene(s) or specific genetic vector construct. The term "expression" or "gene expression" in particular means the transcription of gene(s) or genetic vector construct into mRNA. The process includes transcription of DNA and may include processing of the resulting RNA-product. The term "expression" or "gene expression" may also include the translation of the mRNA and therewith the synthesis of the encoded protein, i.e. protein expression.

EXAMPLES

The following examples serve to illustrate the invention without limiting the scope thereof.

Chemicals and Common Methods

Unless indicated otherwise, cloning procedures carried out for the purposes of the present invention including restriction digest, agarose gel electrophoresis, purification of nucleic acids, ligation of nucleic acids, transformation, selection and cultivation of bacterial cells are performed as described (Sambrook et al., 1989). Sequence analyses of recombinant DNA are performed with a laser fluorescence DNA sequencer (Applied Biosystems, Foster City, CA, USA) using the Sanger technology (Sanger et al., 1977). Unless described otherwise, chemicals and reagents are obtained from Sigma Aldrich (Sigma Aldrich, St. Louis, USA), from Promega (Madison, WI, USA), Duchefa (Haarlem, The Netherlands) or Invitrogen (Carlsbad, CA, USA). Restriction endonucleases are from New England Biolabs (Ipswich, MA, USA) or Roche Diagnostics GmbH (Penzberg, Germany). Oligonucleotides are synthesized by IDT (Coralville, USA).

1. In Vivo Production of Acryloyl-CoA in *S. cerevisiae*

1.1 Heterologous Expression of Short-Chain Acyl-CoA Oxidase (Aco) in *S. cerevisiae*

Short-chain acyl-CoA (coenzyme A) oxidase catalyses an oxidation reaction with saturated acyl-CoAs (e.g. propionyl-CoA) to enoyl-CoAs (e.g. acryloyl-CoA). Nucleotide sequence of the Aco gene (GB: AB017643.1) from *Arabidopsis thaliana* was obtained from the NCBI (http://www.ncbi.nlm.nih.gov/). The nucleotide sequence was codon optimized for expression in yeast with an N-terminal 6x-His tag based on the standard codon usage table in IDT Gene synthesis service (Seq ID No. 57). The 1337 bp of ACO gene was synthesized by IDT (Coralville, USA). The ACO gene fragment flanked by BamHI and HindIII restriction sites was inserted in a vector with 2 micron and pBR322 origin of replicon, ura3 and bla gene as markers to yield pYP137 (high-copy *E. coli/S. cerevisiae* shuttle vector; complements Ura-auxotrophy in *S. cerevisiae*: pBR322; CEN4-origin; AmpR; URA3, ACO under control of truncated HXT71-392 promoter and CYC1 terminator, Seq ID No. 67). The construct is subjected to be introduced in *S. cerevisiae* with various combinations of other genes in the pathway (FIG. 1).

1.2 Heterologous Expression of Propionyl-CoA Transferase in *S. cerevisiae*

Figure 2:
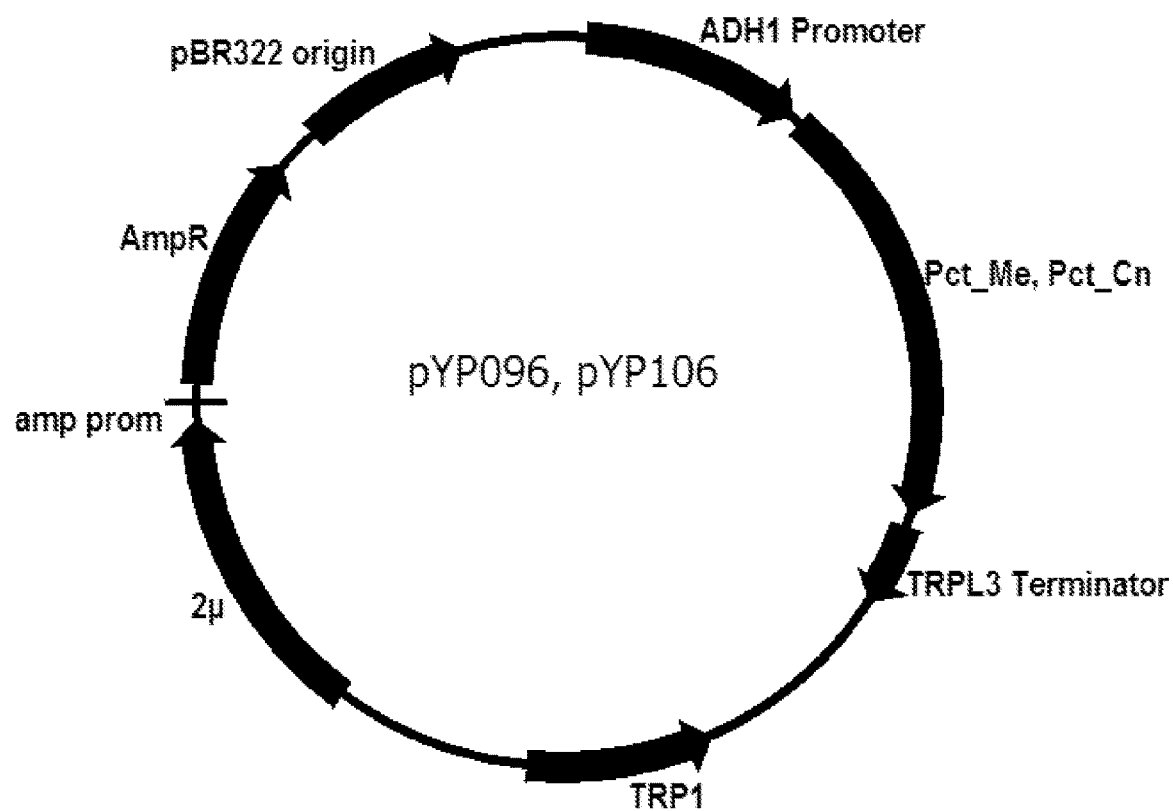
FIG. 2 is a diagram of pYP096, pYP106 construction vector for overexpression of pct in S. cerevisiae.

Enzymatic activity of pct is to transfer CoA to short carbon length acids by forming thioester bond. This yield various acyl-CoAs as intermediates of various biosynthetic pathways. Propionyl-CoA transferases use acetyl-CoA as a CoA donor to create propionyl-CoA from propionate. Pct genes used for this experiment from *Megasphaera elsdenii*, (CCC72964) and from *Cupriavidus necator* (CAJ93797) were codon-optimized for expression in *S. cerevisiae* and synthesized by GeneScript (Piscataway, USA) and IDT (Coralville, USA), yielding pct-Me (Seq ID No. 59) and pct-CN (Seq ID No. 61) (Prabhu et. al 2012). These genes were cloned into gene overexpression plasmids by homologous recombination methods described in prior publications (Gietz et. al., 2007). The pct genes were inserted seamlessly into the *E. coli/S. cerevisiae* shuttle plasmid to overexpress the protein from the strong constitutive promoter ADH1 and TRPL3 terminator with tryptophan auxotrophic marker in 2 micron base high-copy expression vector. The resulting plasmids pYP096 (Seq ID No. 65), and pYP106 (Seq ID No. 66) are listed in the Table 1 (FIG. 2).

TABLE 1

List of plasmids encoding for different propionate CoA-transferase

| Plasmid | Plasmid description | Enzyme Key | Species/Protein | Accession #, Seq ID No. |
|---|---|---|---|---|
| pYP096 | high-copy *E. coli/S. cerevisiae* shuttle vector; complements Trp-auxotrophy in *S. cerevisiae*: pBR322; 2 µm-ori; AmpR; TRP1; ADH1 promoter and RPL3 terminator, contains codon-optimized pct of *M. elsdenii* | Pct-Me | *Megasphaera elsdenii* | CCC72964, Seq ID No. 65 |

TABLE 1-continued

List of plasmids encoding for different propionate CoA-transferase

| Plasmid | Plasmid description | Enzyme Key | Species/Protein | Accession #, Seq ID No. |
|---|---|---|---|---|
| pYP106 | high-copy E. coli/S. cerevisiae shuttle vector; complements Trp-auxotrophy in S. cerevisiae: pBR322; 2 μm-ori; AmpR; TRP1; ADH1 promoter and RPL3 terminator, contains codon-optimized pct of Cupriavidus necator | Pct-Cn | Cupriavidus necator | CAJ93797, Seq ID No. 66 |

2. In Vivo Production of Lactoyl-CoA in S. cerevisiae

In order to produce lactoyl-CoA in the cytosol of S. cerevisiae, conversion of pyruvate to lactate and lactate to lactoyl-CoA has to occur by heterologous enzymes. Lactate dehydrogenase is responsible to convert pyruvate to lactate with NADH, and lactate dehydrogenase (IdhA) from E. coli was expresses in yeast after codon optimization, yielding IdhA-sc (Seq ID No. 69). To overexpress IdhA-sc in S. cerevisiae, a yeast shuttle expression vector was constructed. The IdhA-sc was inserted seamlessly by homologues recombination between the HXT7 promoter and CYC1 terminator on a plasmid (high-copy E. coli/S. cerevisiae shuttle vector; complements His-auxotrophy in S. cerevisiae: pBR322; 2 μ-ori; AmpR; HIS3). The resulting plasmid was named pYP024 (Seq ID No. 71). This plasmid was transformed into S. cerevisiae W303-1A strain to yield strain TYC-006. TYC-006 was cultured in the synthetic media and the cultured broth contained lactate which was converted from lactate. This lactate was converted further to lactoyl-CoA by expression of propionyl-CoA transferase, pct-Me (Seq ID No. 59), and pct-Cn (Seq ID No. 61) in the S. cerevisiae strain with IdhA-sc.

Figure 3:
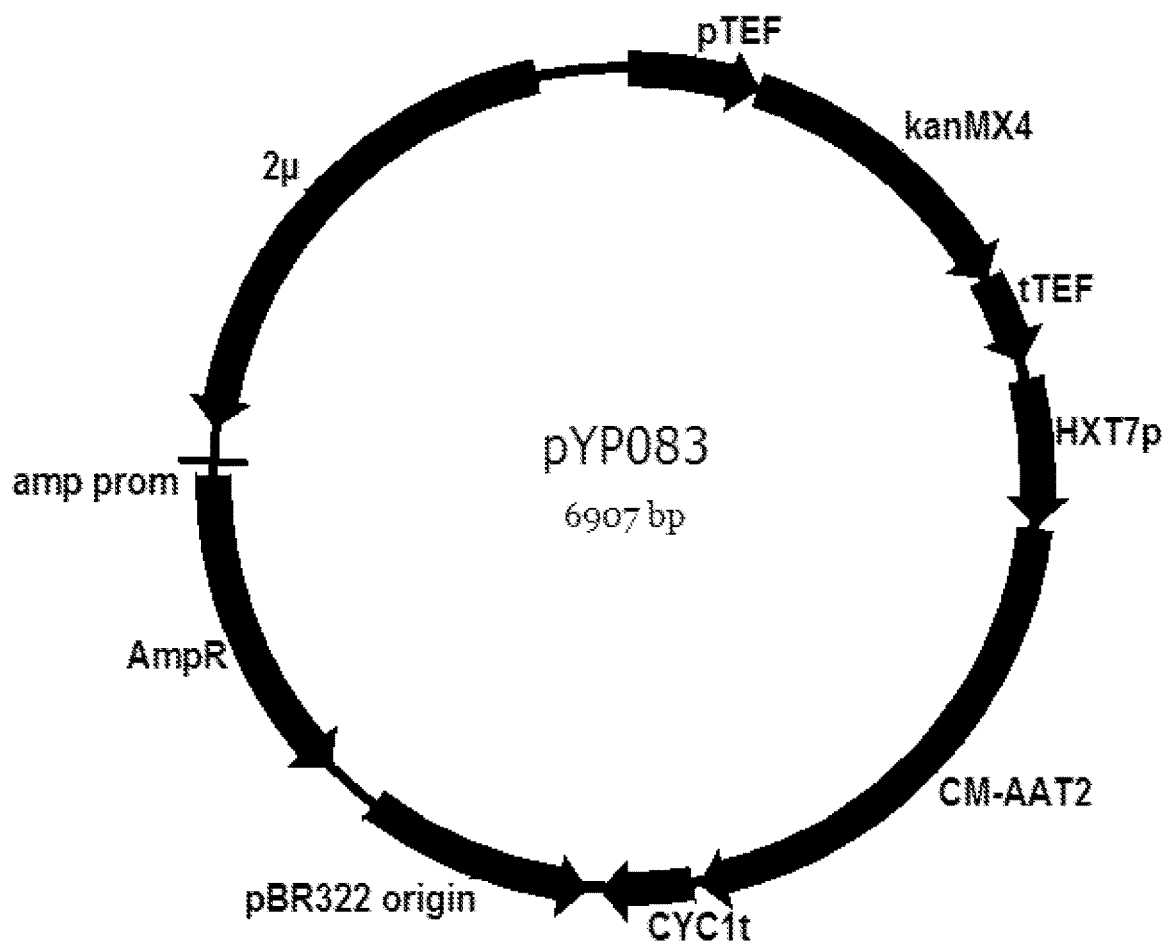
FIG. 3 is a diagram of pYP083 construction vector for overexpression of AAT in S. cerevisiae.

3. Heterologous Expression of Alcohol Acyl Transferase (AAT) in P. pastoris and S. cerevisiae AAT is responsible for forming an ester bond between alcohols and acyl-CoAs. Various putative AATs were chosen for analysis (see Table 2). Selected AAT genes were subjected to go through activity screening tests in vitro. The methylotrophic yeast P. pastoris was chosen as expression host for the evaluation of expression of candidate genes encoding putative AATs. Expression constructs were set up in the plasmid pD902 (DNA 2.0) which provides the strong methanol-inducible AOX promoter. The plasmid was modified by inserting the PARS1 element, which allowed the episomal replication of the plasmid (Cregg, J. M., et al., 1985). Selected candidate AATs were constructed into pD902e plasmids (Seq ID No. 68) and transformed in P. pastoris GapChap. In order to overexpress for example Cm-AAT2 in S. cerevisiae, the gene was cloned in a high copy overexpression vector with a strong promoter and a terminator, yielding pYP083 (Seq ID No. 64, high-copy E. coli/S. cerevisiae shuttle vector; confers geneticin resistance: pBR322; 2 μm-ori; AmpR; lac Z; kanMX; truncated HXT71-392 promoter and CYC1 terminator CDS: N-terminal His tagged CmAAT2_Cucumis melo) (FIG. 3).

TABLE 2

Overview of the AATs selected for expression and characterization

| SEQ ID NO | gene name | identifier | Origin | Origin | reference |
|---|---|---|---|---|---|
| 1 | CM-AAT1 | CAA94432 | Cucumis melo | melon | Yahyaoui et al., 2002 El-Sharkaway et al., 2005 |
| 3 | MpAAT1 | AY707098 | Malus pumila | apple | Souleyre et al., 2005 |
| 5 | VAAT | CAC09062 | Fragaria vesca | strawberry | Beckwilder et al., 2004 |
| 7 | CM-AAT2 | AAL77060 | Cucumis melo | melon | El-Sharkaway et al., 2005 |
| 9 | Md-AAT2 | AAS79797 | Malus domestica | apple | Li et al., 2006 |
| 11 | BEBT | AF500200 | Clarkia breweri | flower | D'Auria et al., 2002 |
| 13 | CbBEAT | AAC18062 | Clarkia breweri | flower | Dudareva et al., 1998 |
| 15 | SAAT | CAC09048 | Fragaria × ananassa | strawberry | Beekwilder et al., 2004 |
| 17 | FaAAT2 | JN089766) | Fragaria × ananassa | strawberry | Cumplido-Laso et al., 2012 |
| 19 | AeAT9 | HO772637 | Actinidia eriantha | kiwi | Günther et al., 2011 |
| 21 | Rh-AAT1 | AAW31948 | Rosa hybrid cultivar | flower | Guterman et al., 2006 |
| 23 | CM-AAT4 | AAW51126 | Cucumis melo | melon | El-Sharkaway et al., 2005 |
| 25 | ACT | WP_001010387 | (Staphylococcus sciuri) | bacterium | Rodriguez et al., 2014 |

TABLE 2-continued

Overview of the AATs selected for expression and characterization

| SEQ ID NO | gene name | identifier | Origin | Origin | reference |
|---|---|---|---|---|---|
| 27 | BanAAT | AX025506 | *Musa sapientum* | banana | Beekwilder et al., 2004 |
| 29 | Glossy2 | CAA61258 | *Zea mays* | maize | Tacke et al., 1995 |
| 31 | CM-AAT3 | AAW51125 | *Cucumis melo* | melon | El-Sharkaway et al., 2005 |
| 33 | BAHDFox | EMT69722 | *Fusarium oxysporum* | fungi | — |
| 35 | VpAAT1 | FJ548611 | *Vasconcellea pubescens* | papaya | Balbotin et al., 2010 |
| 37 | AMAT | AY705388 | *Vitis labrusca* | grape | Wang & De Luca, 2005 |
| 39 | Pun1 | AAV66311 | *Capsicum annum* | pepper | Stewart et al., 2005 |
| 41 | Dv3MaT | AAO12206 | *Dahlia variabilis* | flower | Suzuki et al., 2002 |
| 43 | NtHCT | CAD47830 | *Nicotiana tababcum* | tobacco | Hoffmann et al., 2003 |
| 45 | DBATAca | ACI47063 | *Aspergillus candidus* | fungi | — |
| 47 | TSga | WP_006129805 | *Streptomyces gancidicus* | bacterium | — |
| 49 | TSvi | YP_004810992 | *Streptomyces violaceusniger* | bacterium | — |
| 51 | CAT | YP_007500975 | *Shigella sonnei* | bacterium | Rodriguez et al., 2014 |
| 53 | EHT | NP_009736 | *Saccharomyces cerevisiae* | yeast | Rodriguez et al., 2014 |
| 55 | ATF | NP_015022 | *Saccharomyces cerevisiae* | yeast | Rodriguez et al., 2014 |

4. In Vivo Production of Butanol in *S. cerevisiae*

A butanol producing *S. cerevisiae* (TYC-185) strain was established as described in Schadeweg, V. and E. Boles, 2016.

5. In Vivo Production of nBA by Feeding Substrate

We have established a pathway within *S. cerevisiae* that is able to create n-butylacrylate from feeding of propionate and n-butanol. The first step uses propionyl-CoA transferase (*M. elsdenii*) to convert propionate to propionyl-CoA. Then, the Acyl-CoA dehydrogenase (ACO) enzyme from *A. thaliana* to convert the propionyl-CoA to acryloyl-CoA. Further down the pathway, acryloyl-CoA and n-butanol become key intermediates, which are esterified by the activity of an alcohol acyltransferase (AAT) to the desired end product n-butylacrylate. We used TYC-072 modified strain of *S. cerevisiae* to introduce nBA biosynthetic pathway plasmids. TYC-072 was transformed with a set of plasmids, pYP137 (Seq ID No. 67), pYP096 (Seq ID No. 65), and pYP083 (Seq ID No. 64) from which Aco, pct-Me, and cm-AAT2 are overexpressed, to yield *S. cerevisiae* strain TYC-166. TYC-166 was cultured in synthetic defined SD media (Bacto-Yeast nitrogen base without amino acids, 1.7 g; Glucose, 20 g; Dropout mix, 2 g/1 L) with G418 and without TRP and URA. As a negative control, an empty control vector instead of the Aco vector was introduced into TYC-072 with pct-Me and cm-AAT2 overexpression vectors to yield *S. cerevisiae* strain TYC-181. These strains were grown in SE-TRP-URA+G418 selective minimal media (glutamic acid, 1 g; Bacto-Yeast nitrogen base without amino acids and ammonium sulfate, 1.7 g; Dropoutmix, 2 g; glucose 20 g/1 L) at 30° C. (Table 3).

TABLE 3

Strains to produce n-butylacrylate in *S. cerevisiae*.

| Strain Name | Description of strain | plasmids | Selection markers |
|---|---|---|---|
| TYC-72 | MATa; ura3-52; trp1-289; leu2-3_112; his3 Δ1; MAL2-8C; SUC2 adh1::loxP adh3::loxP; adh4Δ::loxP, adh5Δ::loxP Δadh1,3,4,5 (all with loxP), Ethanol non-producer | none | Auxotrophic: Trp, Ura, Leu, His |
| TYC-166 | Prepared from TYC-072, Ethanol non-producer, overexpress Aco, pct-Me, and Cm-AAT2 | pYP083 (Cm-AAT2) pYP096 (pct-ME) pYP137 (ACO) | Dominant: G418 Auxotrophic: Trp, Ura |
| TYC-181 | Prepared from TYC-072, Ethanol non-producer, overexpress pct-Me, and Cm-AAT2 | pYP004 (empty) pYP083 (Cm-AAT2) pYP096 (pct-ME) | Dominant: G418 Auxotrophic: Trp, Ura |

TABLE 3-continued

Strains to produce n-butylacrylate in *S. cerevisiae*.

| Strain Name | Description of strain | plasmids | Selection markers |
|---|---|---|---|
| TYC-185 | n-Butanol producer. Ethanol non-producer, MATa; ura3-52; trp1-289; leu2 3_112; his3Δ1; MAL2-8C; SUC2; adh1::loxP; adh2Δ::LEU2; adh3::loxP; adh4Δ::loxP; adh5::loxP; adh6Δ::coaA, natNT2; sfa1Δ::adhE, A267T/E568K, hphNT1; gpd2::ERG10, hbd, crt, ter, adhE2, EutE, KanMX | none | Auxotrophic: Ura, Trp, His |

Strains were grown aerobically in test tubes from glycerol stocks in 10 mL of SE-TRP-URA+G418 minimal media overnight at 30° C. and 250 rpm. These cultures were then transferred into a 250 mL baffled glass shake flask and normalized to an OD600 of 0.2 for a 25 mL culture. 3.0 g/L Sodium Propionate and 0.5% butanol were fed to the cultures every 24 hours. An additional 2% of glucose was also fed after the first 24 hours and every 24 hours thereafter. Samples were taken at 3, 6, 9, 12, 24, 36 and 48 hour time points for HPLC and Solid Phase Micro Extraction (SPME) detection. The SPME method was used to detect esters, specifically Butylacrylate, and Butyl propionate.

6. In Vivo Production of nBA from Glucose

In order to demonstrate nBA production in microorganism from glucose as a carbon source, multiple pathways are introduced to generate substrates to the final esterification step, which is performed by AAT enzymes. The two major pathways to produce two key intermediates are heterologous biosynthetic pathways for butanol and acryloyl-CoA. Two *S. cerevisiae* production host as described in the examples 1 and 4 showed production of acryloyl-CoA and butanol in separate experiments. We use the *S. cerevisiae* strain (TYC-185), which can produce butanol by reverse beta-oxidation described in example 4 as a base strain to add an acryloyl-CoA pathway and alcohol acyl transferase (AAT). AAT and genes for the acryloyl-CoA pathway, short chain acyl-CoA oxidase (ACO), propionyl-CoA transferase (pct-Me), methylmalonyl-CoA mutase, methylmalonyl-CoA decarboxylase, are integrated into the chromosome of the base strain with functional promoters and terminators. In addition, other acryloyl-CoA production pathways are used separately and/or collectively. Some of example of other acryloyl-CoA pathways are the lactate route and the 3HP route. The lactate route is composed of a set of enzymes to convert pyruvate to lactate and from lactate to lactoyl-CoA and then to acryloyl-CoA. A 3HP route is composed of a set of enzymes to convert malonyl-CoA or beta-alanine to 3-oxopropanate, which is converted to 3-hydroxypropanoate (3HP) and further to 3-hydroxypropanoyl-CoA and then form acryloyl-CoA. Other routes from glucose to 3HP to acryloyl-CoA are tested. Optimization of the protein expression is achieved by testing various promoters, integration loci, copy-number of genes, episomal plasmid expression, and culture conditions. Once all the necessary genes are expressed in *S. cerevisiae*, glucose is converted to acryloyl-CoA and together with butanol then esterified by an AAT to form nBA and/or other ester compounds.

7. Production of Other Ester Compounds 7.1 In Vivo Production of Other Esters

Various ester compound were produced in the engineered *S. cerevisiae* strains with expression of heterologous pathways for nBA formation. TYC-166 and TYC-181 strains, in which an AAT and pct gene were overexpressed, showed production of n-butylpropionate (nBP) as a by-product along with nBA production. Propionate was fed to the culture broth and transformed by the cells to propionyl-CoA due to the enzyme activity of pct-ME. The propionyl-CoA together with fed butanol were esterified by the AAT activity resulting in production of n-butyl propionate (nBP). Detailed experimental methods are described in example 5. nBP in the culture broth was detected by the methods described in Example 8. Additionally, in vivo production of butyllactate was demonstrated by expression of lactate dehydrogenase and AAT in yeast.

7.2 In Vitro Production of nBA and Other Esters by AATs

In addition to nBA, in vitro formation of other ester compounds, such as butyl propionate, butyl lactate, butyl acetate, and ethyl acetate, were confirmed by in vitro enzyme activity assays using the activity of the purified AAT enzymes, which form ester compounds from acyl-CoAs and alcohols. The methylotrophic yeast *P. pastoris* GapChap, which provides a chaperonin co-expression, was chosen as expression host for the evaluation of expression of candidate genes encoding putative AATs. Plasmid constructs with N-terminal 6X-his-tagged AATs were cloned with the strong methanol-inducible AOX promoter. The cultures of individual constructs were pooled, washed once with 100 mM sodium phosphate buffer pH 7.5 and re-suspended in 50 mM sodium phosphate buffer pH 8.0 containing complete plus EDTA free protease inhibitor (Roche), 300 mM NaCl, mM imidazole. A Branson Sonifier 250 was used to generate a crude cell extract; 8×5 min pulses with 50% duty cycle and output level 7 were used to disrupt the cells in an appropriate vessel on ice. After centrifugation the supernatant was filtered before loading onto a HisTrap HF Ni-NTA column (1 ml, GE Healthcare) equilibrated with buffer A (300 mM NaCl, 50 mM sodium phosphate buffer pH 8.0, 10 mM imidazole). Buffer A was also used for loading and washing. A gradient was applied by switching from buffer A to buffer B (300 mM NaCl, 50 mM sodium phosphate buffer pH 8.0, 500 mM imidazole) within 10 column volumes (CV). Elution was prolonged by 5 additional CV of buffer B. Fractions of 1 ml were collected and separately analyzed by SDS-PAGE and activity measurements (GC/MS) for the identification of AAT protein. Up to 3 fractions were pooled and desalted by size exclusion chromatography (PD10, GE-Healthcare). Final preparations contained 100 mM sodium phosphate buffer pH 7.5 and were stored on ice. Purity was analyzed by SDS-PAGE and densitometric analysis of the corresponding protein band. Total protein amount was determined by Micro-BCA Assay (Thermo Fisher). The assay to determine the activity of AATs was set up as follows: 100 mM potassium phosphate buffer pH 7.5, 5 mM alcohol (e.g. butanol), 0.5 mM acyl-CoA, 1 mg/mL BSA, and 20 µl enzyme sample in a total volume of 100 µl in a 2 mL glass vial, which was sealed immediately after setup. Samples were set up in duplicate and incubated at room temperature (RT) for 0, 2, 4, 8 and 24 h respectively. Subsequently enzymes were inactivated by heat denaturation at 65° C. for 20 min. Afterward samples were analyzed by the methods described in Example 8. Various AATs showed esterase activities to various substrates to form butylacrylate, butyl propionate, butyl lactate, butyl acetate, and ethyl acetate. (Table. 4)

TABLE 4

Activities of AATs towards the formation of variable compounds.

| SEQ ID NO | Enzyme | butyl acrylate | butyl propionate | butyl lactate | ethyl acetate |
|---|---|---|---|---|---|
| 2 | Cm-AAT1 | o | o | o | x |
| 4 | Mp-AAT1 | o | o | o | o |
| 6 | VAAT | o | o | o | o |
| 8 | CM-AAT2 | o | o | o | o |
| 10 | Md-AAT2 | o | o | o | o |
| 12 | BEBT | o | o | x | o |
| 14 | CbBEAT | o | o | x | o |
| 16 | SAAT | x | o | o | o |
| 18 | Fa-AAT2 | x | o | o | o |
| 20 | AeAT9 | x | o | o | o |
| 22 | Rh-AAT1 | x | o | x | o |
| 24 | CM-AAT4 | x | o | x | o |
| 26 | ACT | x | o | x | o |
| 28 | BanAAT | x | x | x | o | o: detected,
x: not detected

8. Detection of nBA from Culture Broth

Figure 4:
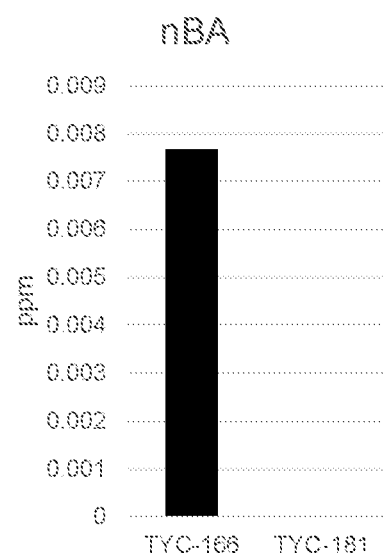
FIGS. 4A and 4B are graphs of nBA and nBP, respectively, production in S. cerevisiae by feeding propionate and butanol. TYC-166 is a test strain with ACO, Pct-Me, and Cm-AAT2 expressed. TYC-181 is a negative control strain with Pct-Me and Cm-AAT2 but without ACO expressed.
Figure 4:
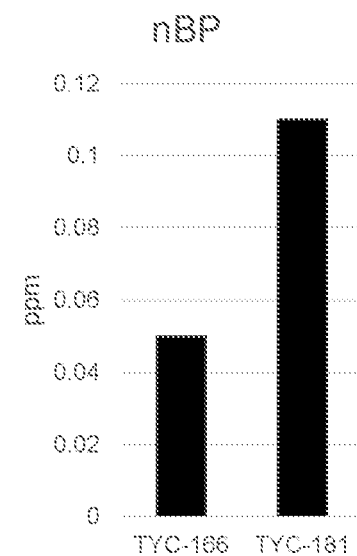

Solid phase micro extraction (SPME)/GC/MS was used to detect nBA and other ester compounds from the culture broth. SPME samples were prepared by adding 500 µL of filtered (0.22 µm) cultured media into the head space analysis vial. SPME was done with carboxen/polydimethylsiloxane fiber. Extraction was done at 40° C. for 15 min after samples were conditioned at 40° C. for 10 min. Desorption was carried out at injection port at 250° C., followed by GC separation (column DB-624) and MS detection (full scan mode). nBA was detected from the broth of TYC-166 culture. No nBA was detected from TYC-181, which was negative control experiment. Both strains produced n-butyl-propionate as a by-product formed by esterification of butanol and propionyl-CoA (FIG. 4).

What is claimed is:

1. A recombinant microorganism comprising a nucleic acid molecule encoding an alcohol acyl transferase (AAT) gene encoding an AAT enzyme having an n-butylacrylate (n-BA) forming activity, wherein the microorganism also comprises a butanol producing pathway and an acryloyl-CoA producing pathway, and wherein the microorganism has an introduced, increased, or enhanced n-butylacrylate forming activity and/or expression of said AAT enzyme;
wherein the AAT gene encoding an AAT enzyme having an n-BA forming activity is selected from the group consisting of:
(I) a nucleic acid molecule comprising a sequence selected from the group consisting of SEQ ID NO: 1, 3, 5, 7, 9, 11, and 13;
(II) a nucleic acid molecule having at least 95% identity to a nucleic acid molecule selected from the group consisting of SEQ ID NO: 1, 3, 5, 7, 9, 11, and 13;
(III) a nucleic acid molecule hybridizing to the full complement of a nucleic acid molecule having a sequence selected from the group consisting of SEQ ID NO: 1, 5, 7, 9, 11, and 13;
(IV) a nucleic acid molecule encoding a polypeptide selected from the group consisting of SEQ ID NO: 2, 6, 8, 10, 12, and 14; and
(V) a nucleic acid molecule encoding a polypeptide having at least 95% identity to a polypeptide selected from the group consisting of SEQ ID NO: 2, 6, 8, 10, 12, and 14.

2. The recombinant microorganism of claim 1, wherein the microorganism is selected from a genus of the group consisting of Saccharomyces, Yarrowia, Arxula, Kluyveromyces, Lactobacillus, Clostridium, Pseudomonas, Corynebacterium, Bacillus, Erwinia, Escherichia, Pantoea, Streptomyces, Zymomonas and Rhodococcus.

3. A composition comprising one or more recombinant microorganisms according to claim 1.

4. The composition of claim 3 further comprising a medium and a carbon source.

5. A method for producing a recombinant microorganism producing n-BA comprising the steps of:
(I) introducing, increasing, or enhancing the activity and/or expression of an alcohol acyl transferase (AAT) gene encoding an AAT enzyme having an n-BA forming activity in a microorganism; and
(II) further introducing in the microorganism a butanol producing pathway and an acryloyl-CoA producing pathway;
wherein the AAT gene encoding an AAT enzyme having an n-BA forming activity is selected from the group consisting of:
(I) a nucleic acid molecule comprising a sequence selected from the group consisting of SEQ ID NO: 1, 3, 5, 7, 9, 11, and 13;
(II) a nucleic acid molecule having at least 95% identity to a nucleic acid molecule selected from the group consisting of SEQ ID NO: 1, 3, 5, 7, 9, 11, and 13;
(III) a nucleic acid molecule hybridizing to the full complement of a nucleic acid molecule having a sequence selected from the group consisting of SEQ ID NO: 1, 5, 7, 9, 11, and 13;
(IV) a nucleic acid molecule encoding a polypeptide selected from the group consisting of SEQ ID NO: 2, 6, 8, 10, 12, and 14; and
(V) a nucleic acid molecule encoding a polypeptide having at least 95% identity to a polypeptide selected from the group consisting of SEQ ID NO: 2, 6, 8, 10, 12, and 14.

6. The method of claim 5, wherein the microorganism is selected from a genus of the group consisting of Saccharomyces, Lactobacillus, Clostridium, Pseudomonas, Corynebacterium, Bacillus, Erwinia, Escherichia, Pantoea, Streptomyces, Zymomonas and Rhodococcus.

7. A recombinant expression construct comprising a promoter functional in a microorganism functionally linked to a nucleic acid molecule having a sequence selected from the group consisting of:
(I) a nucleic acid molecule comprising a sequence selected from the group consisting of SEQ ID NO: 1, 3, 5, 7, 9, 11, and 13; and
(II) a nucleic acid molecule having at least 95% identity to a nucleic acid molecule selected from the group consisting of SEQ ID NO: 1, 3, 5, 7, 9, 11, and 13; and
(III) a nucleic acid molecule hybridizing to the full complement of a nucleic acid molecule having a sequence selected from the group consisting of SEQ ID NO: 1, 5, 7, 9, 11, and 13; and
(IV) a nucleic acid molecule encoding a polypeptide of SEQ ID NO: 2, 6, 8, 10, 12, and 14; and
(V) a nucleic acid molecule encoding a polypeptide having at least 95% identity to a polypeptide selected from the group consisting of SEQ ID NO: 2, 6, 8, 10, 12, and 14,
wherein the promoter is heterologous to the nucleic acid molecule.

8. A recombinant vector comprising the recombinant expression construct of claim 7.

9. A method of culturing or growing a recombinant microorganism comprising inoculating a culture medium with one or more recombinant microorganism according to claim 1 and culturing or growing the one or more recombinant microorganism in the culture medium.

\* \* \* \* \*

```
                       SEQUENCE LISTING

Sequence total quantity: 71
SEQ ID NO: 1            moltype = DNA  length = 1407
FEATURE                 Location/Qualifiers
misc_feature            1..1407
                        note = CM-AAT1
source                  1..1407
                        mol_type = genomic DNA
                        organism = Cucumis melo
SEQUENCE: 1
atgcatcatc accaccacca cgagactatg cagactatcg atttctcatt ccacgttaga   60
aagtgtcagc cagagttgat cgctccagct aacccaactc catacgagtt caagcaattg  120
tccgacgttg acgaccaaca gtccttgaga ttgcagttgc cattcgttaa catctaccca  180
cacaacccat ccttggaggg tagagatcca gttaaggtta tcaaagaggc tatccggtaag  240
gctttggttt tctactaccc attggctggt agattgagag agggtccagg tagaaagttg  300
ttcgttgagt gtactggtga gggtatcttg ttcattgaag ctgacgctga cgtttccttg  360
gaagagttct gggatacttt gccatactcc ttgtcctcca tgcagaacaa catcatccac  420
aacgctttga actccgacga ggtttttgaac tccccttttgt tgttgatcca ggttactaga  480
ttgaagtgtg gtggtttcat cttcggtttg tgtttcaacc acactatggc tgacggtttc  540
ggtatcgttc agttcatgaa ggctactgct gagatcgcta gaggtgcttt cgctccatct  600
attttgccag tttggcagag agcttttgttg actgctagag atccaccaag aatcactttc  660
agacactacg agtacgacca ggttgttgac atgaagtccg gttttgatcc agttaactcc  720
aagatcgacc agttgttctt cttctcccaa ttgcaaatct ccactttgag acagactttg  780
ccagctcact tgcacgactg tccatctttc gaagttttga ctgcttacgt ttggagattg  840
agaactatcg ctttgcagtt caagccagag gaagaggtta gattcctttg tgtttatgaac  900
ttgagatcca agattgacat cccattgggt tactacggta acgctgttgt tgttccagct  960
gttatcacta ctgctgctaa gttgtgtggt aaccctttgg gttacgctgt tgacttgatc 1020
agaaaggcta aggctaaagc tactatgtgaa tacatcaagt ccactgttga tttgatggtt 1080
atcaagggta gaccatactt cactgttgtt ggttccttca tgatgtccga cttgactaga 1140
atcggtgttg agaacgttga cttcggttgg tgtaaggcta ttttcggtgg tccaactact 1200
actggtgcta gaatcactag aggtttggtt tcttctgtgt ttccattcat gaacagaaac 1260
ggtgagaagg gtactgcttt gtccttgtgt ttgccaccac cagctatgga aagattcaga 1320
gctaacgttc acgcttcctt gcaggttaag caagttgttg atgctgttga ctcccacatg 1380
cagactattc aatccgcttc caagtaa                                     1407

SEQ ID NO: 2            moltype = AA  length = 468
FEATURE                 Location/Qualifiers
REGION                  1..468
                        note = CM-AAT1_AA
source                  1..468
                        mol_type = protein
                        organism = Cucumis melo
SEQUENCE: 2
MHHHHHHETM QTIDFSFHVR KCQPELIAPA NPTPYEFKQL SDVDDQQSLR LQLPFVNIYP   60
```

```
HNPSLEGRDP VKVIKEAIGK ALVFYYPLAG RLREGPGRKL FVECTGEGIL FIEADADVSL    120
EEFWDTLPYS LSSMQNNIIH NALNSDEVLN SPLLLIQVTR LKCGGFIFGL CFNHTMADGF    180
GIVQFMKATA EIARGAFAPS ILPVWQRALL TARDPPRITF RHYEYDQVVD MKSGLIPVNS    240
KIDQLFFFSQ LQISTLRQTL PAHLHDCPSF EVLTAYVWRL RTIALQFKPE EEVRFLCVMN    300
LRSKIDIPLG YYGNAVVVPA VITTAAKLCG NPLGYAVDLI RKAKAKATME YIKSTVDLMV    360
IKGRPYFTVV GSFMMSDLTR IGVENVDFGW GKAIFGGPTT TGARITRGLV SFCVPFMNRN    420
GEKGTALSLC LPPPAMERFR ANVHASLQVK QVVDAVDSHM QTIQSASK                 468

SEQ ID NO: 3              moltype = DNA   length = 1383
FEATURE                   Location/Qualifiers
misc_feature              1..1383
                          note = MpAAT1
source                    1..1383
                          mol_type = genomic DNA
                          organism = Malus pumila
SEQUENCE: 3
atgcatcacc accaccatca ctcattctcc gtcttgcagg ttaagagatt gcagccagag      60
ttgatcactc cagctaagtc tactccacaa gagactcctg tcttgtccga catcgacgac    120
caagagtcct tgagagttca gatcccaatc atcatgtgct acaaggacaa cccatccctg    180
aacaagaaca gaaacccagt caaggctatc agagaggctt gtccagagc cttggtttac     240
tactaccca t ggccggtag attgagagag gtccaaaaca gaaagttggt cgttgactgt    300
aacggtgagg gtatcttgtt cgttgaagct tccgctgacg ttaccttgga acaattgggt    360
gacaagatcc tgccaccatg tcctttgttg gaagagttcc tgtacaactt cccaggttcc    420
gacggtatta tcgactgtcc attgctgttg atccaggtta cctgtttgac ctgcggtggt    480
ttcatcttgg ccttgagatt gaaccacact atgtgtgacg ctgccggttt gttgttgttc    540
ttgactgcta ttgctgagat ggctagaggt gctcacgctc catctatttt gccagtttgg    600
gagagagagt tgttgttcgc tagagatcca ccaagaatca cttgtgctca ccacgaatac    660
gaggacgtta ttggtcactc tgacggttct tacgcttctt ccaaccagtc caacatggtc    720
cagagatcct tttacttcgg tgccaaagag atgagggtcc tgagaaagca aattccacca    780
cacttgatct ccacctgttc caccttcgac ttgatcactg ccttgtctgt gaagtgtgaa    840
accttggcct tgaacatcaa cccaaaagag gccgttagag tctcctgtat cgttaacgct    900
agaggtaagc acaacaacgt cagattgcca ttgggttact acggtaacgc tttcgctttc    960
ccagctgcta tttctaaggc tgagccattg tgcaagaacc ctttgggtta cgcttttggag   1020
ttggtcaaga aagctaaggc caccatgaac gaagagtact tggagatccg tgccgacttg   1080
ttggtcttga gaggtagacc acaatactcc ccactggtt cctacttgat cgtttccgac    1140
aacaccagag ttggttcgg tgacgttaac ttccgttggg gtcaaccagt ttttgccggt    1200
ccagttaagg cttttgacct gatctctttc tacgtccaac acaagaacaa caccgaggac   1260
ggtattttgg tcccaatgtg tttgccatcc tccgccatgt ccagagagg atctgcaaca    1320
gagagaatca cccaagagcc aaaagaggac atctgcaaca acttgagatc cacctctcag   1380
taa                                                                 1383

SEQ ID NO: 4              moltype = AA    length = 460
FEATURE                   Location/Qualifiers
REGION                    1..460
                          note = MpAAT1_AA
source                    1..460
                          mol_type = protein
                          organism = Malus pumila
SEQUENCE: 4
MHHHHHHSFS VLQVKRLQPE LITPAKSTPQ ETKFLSDIDD QESLRVQIPI IMCYKDNPSL     60
NKNRNPVKAI REALSRALVY YYPLAGRLRE GPNRKLVVGC NGEGILFVEA SADVTLEQLG    120
DKILPPCPLL EEFLYNFPGS DGIIDCPLLL IQVTCLTCGG FILALRLNHT MCDAAGLLLF    180
LTAIAEMARG AHAPSILPVW ERELLFARDP PRITCAHHEY EDVIGHSDGS YASSNQSNMV    240
QRSFYFGAKE MRVLRKQIPP HLISTCSTFD LITACLWKCR TLALNINPKE AVRVSCIVNA    300
RGKHNNVRLP LGYYGNAFAF PAAISKAEPL CKNPLGYALE LVKKAKATMN EEYLRSVADL    360
LVLRGRPQYS STGSYLIVSD NTRVGFGDVN FGWGQPVFAG PVKALDLISF YVQHKNNTED    420
GILVPMCLPS SAMERFQQEL ERITQEPKED ICNNLRSTSQ                          460

SEQ ID NO: 5              moltype = DNA   length = 1386
FEATURE                   Location/Qualifiers
misc_feature              1..1386
                          note = VAAT
source                    1..1386
                          mol_type = genomic DNA
                          organism = Fragaria vesca
SEQUENCE: 5
atgcaccatc accatcacca tgagaagatt gaggtttcaa tcatatccaa acacacaatc      60
aaaccagca cgagcagttc tccttttgcaa ccatacaaag taaccttatt ggatcagtta    120
actccaccgt cctacgtccc tatggtgttt tctacccta ttacgggtcc agccgtgttc     180
aatttgcaaa cattggcaga tctgagacac gcattgtctg agactttgac actgtactat    240
ccattatcgg tcgtgtgaa aaacaatctg tatattgatg atttgaaga gggtgttccc     300
tacttggaag cgagagtgaa ctgcgacatg aatgactttt tgaggcttcc aaaaatcgaa    360
tgtttgaatg aatttgttcc aatcaagcct ttttctatgg aggctatatc cgatgaaaga    420
tatctcttac ttggtgtgca agtcaacatt ttcaattccg gatcgcaat tggagttagc    480
gtatcccata agttgatcga cggtcgtaca tctgactgct ccctgaagtc atggtgtgct    540
gtattccgag gatcacgtga caaaatcatc catcccaatc tttcgcaggc agctttgttg    600
tttcctccgc gtgacgatct cccagagaaa tatgctagac aaatggaggg cttgtggttt    660
gttggtaaaa aggttgctac tagaagattc gtgttcggag caaggctat ctctgttatt    720
caagacgagg ctaagtcaga gtccgttcca aaaccatcaa gagttcaagc tgtcacatcc    780
```

```
ttcttatgga aacaccttat tgcaacttct agagctttaa cttcgggtac aactagtact    840
agactatcca ttgctaccca ggtcgtcaac attagaagta ggagaaatat ggaaacggtg    900
tgggataatg ccattggtaa tcttatctgg tttgctcctg caatcttgga actgtctcat    960
acaaccttgg agatctccga tttgaaactg tgtgatctgg ttaacctact caatggttcc   1020
gtcaaacaat gtaatggcga ttacttcgag actttttatg gtaaggaagg ttatgatca    1080
atgtgtgagt acttggactt ccaacgtaca atgtccagca tggaaccagc tccagaaatc   1140
taccttttca cttcatggac caatttcttc aaccagctag actttggatg gggtagaacc   1200
agctggattg tgtagctgg aaagataaa agtgcttttt gtaacctgac tacattggta   1260
cccactcctt gcgatacagg aattgaggca tgggttaacc ttgaagagga aaagatggcc   1320
atgttggaac aagaccctca gtttctggcc ttagcctctc caaaaacttt gatatctagg   1380
tattaa                                                              1386

SEQ ID NO: 6            moltype = AA   length = 461
FEATURE                 Location/Qualifiers
REGION                  1..461
                        note = VAAT_AA
source                  1..461
                        mol_type = protein
                        organism = Fragaria vesca
SEQUENCE: 6
MHHHHHHEKI EVSIISKHTI KPSTSSSPLQ PYKLTLLDQL TPPSYVPMVF FYPITGPAVF     60
NLQTLADLRH ALSETLTLYY PLSGRVKNNL YIDDFEGVTP YLEARVNCDM NDFLRLPKIE    120
CLNEFVPIKP FSMEAISDER YPLLGVQVNI FNSGIAIGVS VSHKLIDGRT SDCFLKSWCA    180
VFRGSRDKII HPNLSQAALL FPPRDDLPEK YARQMEGLWF VGKKVATRRF VFGAKAISVI    240
QDEAKSESVP KPSRVQAVTS FLWKHLIATS RALTSGTTST RLSIATQVVN IRSRRNMETV    300
WDNAIGNLIW FAPAILELSH TTLEISDLKL CDLVNLLNGS VKQCNGDYFE TFMGKEGYGS    360
MCEYLDFQRT MSSMEPAPEI YLFTSWTNFF NQLDFGWGRT SWIGVAGKIE SAFCNLTTLV    420
PTPCDTGIEA WVNLEEEKMA MLEQDPQFLA LASPKTLISR Y                       461

SEQ ID NO: 7            moltype = DNA   length = 1404
FEATURE                 Location/Qualifiers
misc_feature            1..1404
                        note = CM-AAT2
source                  1..1404
                        mol_type = genomic DNA
                        organism = Cucumis melo
SEQUENCE: 7
atgcatcacc atcaccacca cgagactatg cagactatcg acttctcatt ccaggttaga     60
aagtgtcagc cagagttgat cgctccagct aacccaactc catacgagtt caagcaattg    120
tccgacgttg acgaccaaca gtccttgaga ttccagttgc cattggttaa catctaccac    180
cacaacccat cctggagggg tagagatcca gttaaggtta tcaaagaggc tatcgctaag    240
gctttggttt tctactaccc attggctggt agattgagag agggtcctgg tagaaagttg    300
ttcgttgagt gtactggtga gggtatcttg ttcattgaag ctgacgctga cgtttccttg    360
gagcagttca gagatacttt gccatactcc ttgtcctcca tggaaaacaa catcatccac    420
aactcattga actccgacgg tgttttgaac tccccttttgt tgttgatcca ggttactaga    480
ttgaagtgtg gtggtttcat cttcggtatc cacttcgacc acactatggc tgacggtttt    540
ggtatcgctc agttcatgaa ggctatcgct gagatcgctc gaggtgcttt cgctccatct    600
attttgccag tttggcagag agcttttgttg actgctagag atcctccaag aatcactgtt    660
agacactacg agtacgacca ggtcgttgac actaagtcca ctttgatccc agctaacaac    720
atgatcgaca gattgttctt cttcactcag agacagatct ccacattgag acagactttg    780
ccagctcact tgcacgactg ttcttcattc gaggttttac ttggagattg taggaagttg    840
agaactatcg ctttccagtt gaagccagag gaagaggtta gattcttgtg tgttgttaac    900
ttgagatcca gatcgacat cccattgggt ttctacggta acgctatcgt tttcccagct    960
gttatcacta ctgttgctaa gttgtgtggt aaccctttgg gttacgctgt tgacttgatc   1020
agaaaggcta aggctaaagc tacaaaagag tacatcaagt ccatggttga cttcatggtt   1080
atcaagggta gaccaagatt cactgagatc ggtccattca tgatgtccga cattactaga   1140
atcggtttcg agaacgttga cttcggttgg ggtaaggcta ttttcggtgg tccaattatc   1200
ggtggttgtg tatcatcag aggtatgatc tcttactcca ttgctttcat gaacagaaac   1260
ggtgagaagg gaatcgttgt tccattgtgt ttgccaccac agctatgga agattcaga     1320
gctaacgttc acgcttcctt gcaggttatc caggttttga caaggttga cagagacatg   1380
caaacaatct tgtccgcttt gtaa                                          1404

SEQ ID NO: 8            moltype = AA   length = 467
FEATURE                 Location/Qualifiers
REGION                  1..467
                        note = CM-AAT2_AA
source                  1..467
                        mol_type = protein
                        organism = Cucumis melo
SEQUENCE: 8
MHHHHHHETM QTIDFSFQVR KCQPELIAPA NPTPYEFKQL SDVDDQQSLR FQLPLVNIYH     60
HNPSLEGRDP VKVIKEAIAK ALVFYYPLAG RLREGPGRKL FVECTGEGIL FIEADADVSL    120
EQFRDTLPYS LSSMENNIIH NSLNSDGVLN SPLLLIQVTR LKCGGFIFGI HFDHTMADGF    180
GIAQFMKAIA EIARGAFAPS ILPVWQRALL TARDPPRITV RHYEYDQVVD TKSTLIPANN    240
MIDRLFFFTQ RQISTLRQTL PAHLHDCSSF EVLTAYVWRL RTIAFQLKPE EEVRFLCVVN    300
LRSKIDIPLG FYGNAIVFPA VITTVAKLCG NPLGYAVDLI RKAKAKATKE YIKSMVDFMV    360
IKGRPRFTEI GPFMMSDITR IGFENVDFGW GKAIFGGPII GGCGIIRGMI SYSIAFMNRN    420
GEKGIVVPLC LPPPAMERFR ANVHASLQVI QVLDKVDRDM QTILSAL                 467
```

| SEQ ID NO: 9 | moltype = DNA  length = 1398 |
|---|---|
| FEATURE | Location/Qualifiers |
| misc_feature | 1..1398 |
| | note = Md-AAT2 |
| source | 1..1398 |
| | mol_type = genomic DNA |
| | organism = Malus domestica |

SEQUENCE: 9

```
atgcatcacc atcaccacca catgccattc tccgttttgc aggttaagag attgcagttg    60
gagttgatca ctcctgctaa gccaacattg caagaggcta agttcttgtc cgacatcgac   120
gaccaagagg gtttgagatt ccaggttcca gttatcatgt gttacaagga caacccatcc   180
ttgaacaaga actgtaaccc agttaaggtt atcagagagg ctttgtccag agctttggtt   240
tactactacc cattggctgg tagattgaaa gagggtccaa acagaaagtt gatggttgac   300
tgtaacggtg agggtatctt gttcgttgaa gcttccgctg acgttacttt ggagcaattg   360
ggtgacaaga ttttgccacc atgtcctttg ttggaagagt ttttgttcaa cttcccaggt   420
tccgacggta tcatcggatg tcctttgttg ttggttcagg ttacttgttt gacttgtggt   480
ggtttcatct tggctttgag agttaaccac actatgtgtg acgctccagg tttgttgttg   540
ttcttgactg ctatcgctga gatggctaga ggtgctcatg ctccatctat tttgccagtt   600
tgggagagag agttgttgtt ttccagagat ccaccaagaa tcacttgtgc tcaccacgaa   660
tacgaggacg ttattgacca ctctgacggt tgtacgctt cttccaacca gtccaacatg   720
gttcagagat ccttctactt cggtgctaaa gagatgagag ttttgagaaa gcagatccca   780
ccacacttga tctccacttg ttccactttc gacttgatca ctgcttgttt gtggaagtgt   840
agaactttgg ctttgaacat caacccaaaa gaggctgtta gagtttcctg tatcgttaac   900
gctagaggta agcacaacaa cgttagattg ccattgggtt actacggtaa cgctttcgct   960
ttcccagctg ctatttctaa ggctgagcca ttgtgtaaga acccttttggg ttacgctttg  1020
gagttggtta gaaagctaa ggctactatg aacgaagagt tggttaagaa ggctactatg  1080
ttgttggttt tgagaggtag acctcagtac tcctccactg gatcctactt gatcgtttcc  1140
gacaacacta gagctggttt cggtgacgtt aacttcggtt ggggtcaacc agtttttgct  1200
ggtccagcta aagctttgga cttgatttcc ttctacgttc aacacaagaa caatactgag  1260
gacggaattt tggttccaat gtgtttgcca tcctccgcta tggaaagatt ccagcaagag  1320
ttggagagaa tcactcaaga gcctaaagag gacatctgta caatttgag atccactaga  1380
attatgtcca tgatgtaa                                                1398
```

| SEQ ID NO: 10 | moltype = AA  length = 465 |
|---|---|
| FEATURE | Location/Qualifiers |
| REGION | 1..465 |
| | note = Md-AAT2_AA |
| source | 1..465 |
| | mol_type = protein |
| | organism = Malus domestica |

SEQUENCE: 10

```
MHHHHHHMPF SVLQVKRLQL ELITPAKPTL QEAKFLSDID DQEGLRFQVP VIMCYKDNPS   60
LNKNCNPVKV IREALSRALV YYYPLAGRLK EGPNRKLMVD CNGEGILFVE ASADVTLEQL  120
GDKILPPCPL LEEFLFNFPG SDGIIGCPLL LVQVTCLTCG GFILALRVNH TMCDAPGLLL  180
FLTAIAEMAR GAHAPSILPV WERELLFSRD PPRITCAHHE YEDVIDHSDG LYASSNQSNM  240
VQRSFYFGAK EMRVLRKQIP PHLISTCSTF DLITACLWKC RTLALNINPK EAVRVSCIVN  300
ARGKHNNVRL PLGYYGNAFA FPAAISKAEP LCKNPLGYVL ELVKKAKATM NEEYLRSVAD  360
LLVLRGRPQY SSTGSYLIVS DNTRAGFGDV NFGWGQPVFA GPAKALDLIS FYVQHKNNTE  420
DGILVPMCLP SSAMERFQQE LERITQEPKE DICNNLRSTR IMSMM                  465
```

| SEQ ID NO: 11 | moltype = DNA  length = 1389 |
|---|---|
| FEATURE | Location/Qualifiers |
| misc_feature | 1..1389 |
| | note = BEBT |
| source | 1..1389 |
| | mol_type = genomic DNA |
| | organism = Clarkia breweri |

SEQUENCE: 11

```
atgcatcatc accatcacca cgctcacgac caatctttgt cttttcgaggt ctgcagaaga    60
aagcccgagt tgattagacc agctaagcaa actccacacg agttcaagaa gttgtccgac   120
gttgaagatc aagagggtct gagattccag atcccagtca tccaattcta caagcacaac   180
aacgagtcca tgcaagagag agatccagtc aggttatca gagagggtat cgctagagcc   240
ttggtctact actacccatt cgctggtaga ttgagagagg tcgacggtag aaagttggtt   300
gttgagtgta ctggtgaggg tgtcatgttc attgaagctg acgtgacgt taccttggag   360
caatttggtg atgcattgca gccaccattc ccatgtttcg accagttgtt gttcgacgtt   420
ccaggttccg gtggtattt ggactctcca ttgctgttga tccaggtcac cagattgaag   480
tgcggttcct tcatcttcgc cttgagattg aaccacacta ggctgatgc tgccggtatc   540
gtcttgttca tgaaggctgt tggtgagatg gctagaggtc ctgctactcc atctacttttg   600
ccagttgggg acagacacat cttgaacgct agagttccac cacagttac cttcaaccac   660
agagagtacg aagaggtcaa gggaactatc ttcactccat cgatgacttt ggcccacaga   720
tccttttttct tcggttccac tgaaatctcc gccatgagaa agcaaatccc accacacttg   780
agatcctgtt ccactaccat cgaggttttg actgcttgtt gtggcgttg tagaaccttg   840
gccattaagc aaacccccaga cgaagaggtg agaatgatct gtatcgttaa cgccagatcc   900
aagttcaacc caccattgcc agatggttac ttcgtcgact tccgctgttg  ga aaccttg   960
gttactactg ccggtaagtt gtgtaacaac ccattgggtt cgccttgga gttgatcaga  1020
aaggccaaga gagaggtcac cgaagagtac atgcattccg ttgctgactt gatggttgct  1080
actggtagac acactttcac cgttgtcaac acctacttgg tttccgacgt tactagagct  1140
ggtttcggtg aagttgattt cggttggggt gaagctgttt acggtggtcc agctaaaggt  1200
ggtgttggtg ttattccagg tgtcacctcc ttctacatcc cactgagaaa cagacaaggt  1260
```

-continued

```
gagaagggta tcgttctgcc aatctgtttg ccatccgctg ccatggaaat tttcgctgag  1320
gctttgaaca acaccctgaa cggtaaagag atcgagatcg ctaagcactt cactcagtcc  1380
tccctgtaa                                                          1389

SEQ ID NO: 12             moltype = AA  length = 462
FEATURE                   Location/Qualifiers
REGION                    1..462
                          note = BEBT_AA
source                    1..462
                          mol_type = protein
                          organism = Clarkia breweri
SEQUENCE: 12
MHHHHHHAHD QSLSFEVCRR KPELIRPAKQ TPHEFKKLSD VEDQEGLRFQ IPVIQFYKHN   60
NESMQERDPV QVIREGIARA LVYYYPFAGR LREVDGRKLV VECTGEGVMF IEADADVTLE  120
QFGDALQPPF PCFDQLLFDV PGSGGILDSP LLLIQVTRLK CGSFIFALRL NHTMADAAGI  180
VLFMKAVGEM ARGAATPSTL PVWDRHILNA RVPPQVTFNH REYEEVKGTI FTPFDDLAHR  240
SFFFGSTEIS AMRKQIPPHL RSCSTTIEVL TACLWRCRTL AIKPNPDEEV RMICIVNARS  300
KFNPPLPDGY YGNAFAIPAA VTTAGKLCNN PLGFALELIR KAKREVTEEY MHSVADLMVA  360
TGRPHFTVVN TYLVSDVTRA GFGEVDFGWG EAVYGGPAKG GVGVIPGVTS FYIPLRNRQG  420
EKGIVLPICL PSAAMEIFAE ALNNTLNGKE IEIAKHFTQS SL                     462

SEQ ID NO: 13             moltype = DNA  length = 1320
FEATURE                   Location/Qualifiers
misc_feature              1..1320
                          note = CbBEAT
source                    1..1320
                          mol_type = genomic DNA
                          organism = Clarkia breweri
SEQUENCE: 13
atgcatcatc accaccacca caacgttact atgcactcca agaagttgct gaagccatcc   60
atcccaactc caaaccactt gcagaagtta aacttgtcct tgctggacca gatccagatc  120
ccattctacg tcgtttgat cttccactac gagactttgt ctgacaactc cgacatcacc  180
ttgtccaagt tggaatcttc cttgtccgag actctgacct tgtactacca tgttgccggt  240
agatacaacg gtactgactg tgttatcgag tgcaacgacc agggtattgg ttacgttgaa  300
actgccttcg acgttgagtt gcaccacttc ttgttgggtg aagagtccaa caacttggac  360
ttgttggttg gtttgtccgg tttcttgtcc gaaactgaga ctccaccatt ggctgctatc  420
cagctgaaca tgtttaagtg cggtggtttg gttatcggtg cccagttcaa ccacattatc  480
ggtgacatgt tcaccatgtc caccttcatg aactcttggg ctaaggcctg tagagtcggt  540
atcaaagaag ttgctcaccc aactttcggt ttggcccat tgatgccatc tgccaaggtt  600
ttgaacattc caccaccacc atctttcgag ggtgtcaagt tcgtttccaa gaggttcgtg  660
ttcaacgaga acgccatcac cagattgaga aagaggcta ctgaagagga cggtgatggt  720
gatgacgacc aaaagaagaa gaggccatcc agagttgact tggttactgc cttcttgtcc  780
aagtcctga tcgagatgga ctgcgctaag aaagagcaga ctaagtccag accatccctg  840
atggttcaca tgatgaacct gagaaagaga actaagctgg ccttggagaa cgacgtttcc  900
ggtaacttct tcatcgttgt taacgccgag tccaagatca ctgttgctcc aaagatcact  960
gacttgaccg aatctttggg ttccgcttgt ggtgagatta tctccgaggt tgctaaggtt 1020
gacgacgctg aagttgtttc ctccatggtt ttgaactccg tccgtgagtt ctactacgaa 1080
tggggtaagg gtgagaagaa cgtgttcttg tacacctcct ggtgtagatt cccactgtac 1140
gaagttgatt tcggttgggg tatcccatcc ttggttgaca ctactgctgt tccattcggt 1200
ctgatcgttt tgatggatga agctccagct ggtgacggta tgctgttag agcttgtttg 1260
tctgagcacg acatgatcca attccaacag caccaccagt tgctgtccta cgtttcttaa 1320

SEQ ID NO: 14             moltype = AA  length = 439
FEATURE                   Location/Qualifiers
REGION                    1..439
                          note = CbBEAT_AA
source                    1..439
                          mol_type = protein
                          organism = Clarkia breweri
SEQUENCE: 14
MHHHHHHNVT MHSKKLLKPS IPTPNHLQKL NLSLLDQIQI PFYVGLIFHY ETLSDNSDIT   60
LSKLESSLSE TLTLYYHVAG RYNGTDCVIE CNDQGIGYVE TAFDVELHQF LLGEESNNLD  120
LLVGLSGFLS ETETPPLAAI QLNMFKCGGL VIGAQFNHII GDMFTMSTFM NSWAKACRVG  180
IKEVAHPTFG LAPLMPSAKV LNIPPPPSFE GVKFVSKRFV FNENAITRLR KEATEEDGDG  240
DDDQKKKRPS RVDLVTAFLS KSLIEMDCAK KEQTKSRPSL MVHMMNLRKR TKLALENDVS  300
GNFFIVVNAE SKITVAPKIT DLTESLGSAC GEIISEVAKV DDAEVVSSMV LNSVREFYYE  360
WGKGEKNVFL YTSWCRFPLY EVDFGWGIPS LVDTTAVPFG LIVLMDEAPA GDGIAVRACL  420
SEHDMIQFQQ HHQLLSYVS                                               439

SEQ ID NO: 15             moltype = DNA  length = 1377
FEATURE                   Location/Qualifiers
misc_feature              1..1377
                          note = SAAT
source                    1..1377
                          mol_type = genomic DNA
                          organism = Fragaria X ananassa
SEQUENCE: 15
atgcatcatc accaccacca cgagaagatc gaggtttcca ttaactccaa gcacactatc   60
aagccttcca cttcctccac tccattgcag ccatacaagt tgactttgtt ggaccagttg  120
```

-continued

```
actccaccag cttacgttcc aatcgttttc ttctacccaa tcactgacca cgacttcaac    180
ttgccacaaa ctttggctga cttgagacag gctttgtccg agactttgac tttgtactac    240
ccattgtccg gtagagttaa gaacaacttg tacatcgacg acttcgaaga gggtgttcca    300
tacttggagg ctagagttaa ctgtgatatg actgacttct tgagattgag aaagatcgag    360
tgtttgaacg agttcgttcc aatcaagcca ttctccatgg aagctatctc cgacgagaga    420
tacccttttgt tggggtgttca ggttaacgtt ttcgactccg gtatcgctat cggtgttttct    480
gtttcccaca agttgatcga cggtggtact gctgactgtt tcttgaagtc ttgggggtgct    540
gttttcagag gttgtagaga gaacatcatc cacccatctt tgtccgaggc tgctttgttg    600
tttccaccaa gagatgactt gccagagaag tacgttgacc agatggaagc tttgtggttg    660
gctggtaaga aggttgctac tagaagattc gttttcggtg taaggctat ctcctccatt    720
caggacgaag ctaagtctga gtctgttcca aagccatcca gagttcacgc tgttactggt    780
ttcttgtgga agcacttgat cgctgcttcc agagctttga cttctggtac tacttccact    840
agattgtcca ttgctgctca ggctgttaac ttgagaacta gaatgaacat ggaaactgtt    900
ttggacaacg ctactggtaa ccttgttctgg tgggctcagg ctatttttga gttgtctcac    960
actactccag agatcccga cttgaagttg tgtgacttgg ttaacttgtt gaacggttcc   1020
gttaagcagt gtaacggtga ctacttcgag acttttcaagg gtaaagaggg ttacggtaga   1080
atgtgtgagt acttggactt ccagagaact atgtcctcca tggaaccagc tccagatatc   1140
tacttgtttct cctcctggac taacttcttc aacccattgg atttcggttg gggtagaact   1200
tcctggattg tgttgctgg taagattgag tccgcttcct gtaagttcat catttttggtt   1260
ccaactcagt gtggttccgg tatcgaagct tgggttaact tggaagaaga aagatggct   1320
atgttggagc aagaccccaca cttcttggct ttggcttctc caaagacttt gatctaa      1377
```

```
SEQ ID NO: 16          moltype = AA   length = 458
FEATURE                Location/Qualifiers
REGION                 1..458
                       note = SAAT_AA
source                 1..458
                       mol_type = protein
                       organism = Fragaria X ananassa
SEQUENCE: 16
MHHHHHHEKI EVSINSKHTI KPSTSSTPLQ PYKLTLLDQL TPPAYVPIVF FYPITDHDFN    60
LPQTLADLRQ ALSETLTLYY PLSGRVKNNL YIDDFEEGVP YLEARVNCDM TDFLRLRKIE   120
CLNEFVPIKP FSMEAISDER YPLLGVQVNV FDSGIAIGVS VSHKLIDGGT ADCFLKSWGA   180
VFRGCRENII HPSLSEAALL FPPRDDLPEK YVDQMEALWF AGKKVATRRF VFGVKAISSI   240
QDEAKSESVP KPSRVHAVTG FLWKHLIAAS RALTSGTTST RLSIAAQAVN LRTRMNMETV   300
LDNATGNLFW WAQAILELSH TTPEISDLKL CDLVNLLNGS VKQCNGDYFE TFKGKEGYGR   360
MCEYLDFQRT MSSMEPAPDI YLFSSWTNFF NPLDFGWGRT SWIGVAGKIE SASCKFIILV   420
PTQCGSGIEA WVNLEEEKMA MLEQDPHFLA LASPKTLI                           458
```

```
SEQ ID NO: 17          moltype = DNA   length = 1194
FEATURE                Location/Qualifiers
misc_feature           1..1194
                       note = Fa-AAT2
source                 1..1194
                       mol_type = genomic DNA
                       organism = Fragaria X ananassa
SEQUENCE: 17
atgcatcatc accaccacca ctcctacaag aacaaccact ccattttgtc caagccaaac    60
gacccagttg aggttatcag agatgctttg tccaaggctt tgcagttcta ctacccattg   120
gctggtagat tgagagaggg tccaaacaag aaattgatgg ttgactgtac tggtgagggt   180
atcttgttcg ttgaagctaa cgctgaggtt actttggacg aattgggtga acgctatctg   240
ccaccatgtc cattcttgga cggttcttt ttcaacgttc caggttccga cggtattttg   300
ggttccccat tgtgtttgat ccaggttact agattgtcct gtggtggttt catcttcgct   360
ttgagattga accacactat ctgtgacgct ttgggttgg ttcagttctt gaacgctgtt   420
ggtgagatcg ctcagggtaa atacgctcca tccattactc cagtttggga gagagagttg   480
ttgtccgcta gagatccacc aagaatctct tgtactcacg aagagttcga cgactccatt   540
gaccactctt acccaaacta cggtgctact gttcagcagt gttactgttt cggtccaaaa   600
gagatcaagt ccttgagaga gcatttgcca ccacacttgt ctacttgttc ctccactttc   660
gagttgatca ctgccttgtgt ttggaagtgt agaactatct ccttggacat ggaccccagg   720
cagatcgtta gattgtcttg tgttgttact gctttgggta agcacaacaa cgttgtttg   780
ccattgggtt actacggtaa cactttccact tacccagctg ttgtttccac tgctgagaga   840
ttgtgtaact ccccctttggg ttacgctgtt gagttggtta agaaatccaa ggctaagatg   900
tccgaagagt acttgagatc cgctatcgac ttcgttgagg ttagaggtag accaccattc   960
gctttggaag tatgtccga cttcttgtt tccgacaaca tgaacttggt tttgggtgg   1020
atcgacttcg gttccggtaa gccagtttac gctggtgttg ctaagctccac tgacttgatc   1080
tcattctacg ttagatccac taacaaagaa gagagagaga ttttggttcc agtttgtttg   1140
cctatcttgt ccatggaaat cttccagcaa gagttgaaga gatgatcgg ttag           1194
```

```
SEQ ID NO: 18          moltype = AA   length = 397
FEATURE                Location/Qualifiers
REGION                 1..397
                       note = Fa-AAT2_AA
source                 1..397
                       mol_type = protein
                       organism = Fragaria X ananassa
SEQUENCE: 18
MHHHHHHSYK NNHSILSKPN DPVEVIRDAL SKALQFYYPL AGRLREGPNK KLMVDCTGEG    60
ILFVEANAEV TLDELGDAIL PPCPFLDGFL FNVPGSDGIL GSPLCLIQVT RLSCGGFIFA   120
LRLNHTICDA LGLVQFLNAV GEIAQGKYAP SITPVWEREL LSARDPPRIS CTHEEFDDSI   180
```

```
DHSYPNYGAT VQQCYCFGPK EIKSLREHLP PHLSTCSSTF ELITACVWKC RTISLDMDPE    240
QIVRLSCVVT ALGKHNNVCL PLGYYGNTFT YPAVVSTAER LCNSPLGYAV ELVKKSKAKM    300
SEEYLRSAID FVEVRGRPPF ALEGMSDFLV SDNTRTGLGE IDFGFGKPVY AGVAKSTDLI    360
SFYVRSTNKE EREILVPVCL PILSMEIFQQ ELKKMIG                             397

SEQ ID NO: 19           moltype = DNA  length = 1317
FEATURE                 Location/Qualifiers
misc_feature            1..1317
                        note = AeAT9
source                  1..1317
                        mol_type = genomic DNA
                        organism = Fragaria X ananassa
SEQUENCE: 19
atgcaccatc accatcacca tgcctcctcc gtccgtctag tcaaaaagcc tgttttagtg      60
gcaccagttg acccaacacc atcaaccgtc ttgagccttt cctctctaga ctcgcaactg     120
ttcctccgat tccccattga gtatctgctt gtctatgctt ctccacatgg agtggatagg     180
gcagtcactg ctgcaagggt aaaagcagca ctggcaagat cattagtgcc atactatcct     240
ttggctggac gtgtgaaaac tagaccggat tctactgagt tagacgttgt ctgtcaagct     300
caaggtgctg gtttgctgga ggcagttttc gactacacgg ctagtgactt tcaaagagcc     360
cccagatctg ttacagaatg gaggaagctg ctgttggtcg aagtctttaa ggttgtacct     420
ccactggtgg ttcaattaac ttggttatca gatggttgtg tagctttggg tgttggcttc     480
agtcactgtg taatcgatgg aattggttca agtgagtttt tgaacctttt tgctgagcta     540
gccacaggta gagctagatt gagcgaattt cagccaaaac ccgtttggga tagacattta     600
ctcaatagcg ctggtagaac aaatcttggt actcaccccg agttcggacg tgtgcctgat     660
ttgtcagggt tcgttacccg tttcactcag gaaagacttt cccctacctc gatcacattt     720
gataagacat ggttgaaaga gttgaaaaat attgcaatgt ccacttcaca acctggcgga     780
ttcccataca catcctttga ggtattgagc ggacatatct ggcgtagttg ggcccgttcg     840
tgaatttgc cagctaaaca ggtattgaaa ctactcttct ccataaacat cagaaacaga     900
gttaagcctt ctttgcctgc gggatactat ggtaatgcat ttgttctggg ttgtgctcaa     960
acatccgtta aggatcttac tgagaaagga ttgggttact gtgctgactt ggtcagaggt    1020
gctaaggaaa gagtgggtga tgaatatgcc agggaagtcg ttgagtcagt gagttggcca    1080
cgtagagcat cccccggactc cgtgggtgtg ttgatcatta gccaatggtc tagattagga    1140
ctggaccgtg ttgactttgg ttgggccgt cctgtacagg tgggtccaat ttgttgcgat    1200
agatattgcc ttttcttgcc tgttaggaa tccacggaat ctgtgaaggt tatggttgct    1260
gttccaactt ctgctgttga cagatacgaa tacttcatca gatcaccata ctcctag       1317

SEQ ID NO: 20           moltype = AA  length = 438
FEATURE                 Location/Qualifiers
REGION                  1..438
                        note = AeAT9_AA
source                  1..438
                        mol_type = protein
                        organism = Fragaria X ananassa
SEQUENCE: 20
MHHHHHHASS VRLVKKPVLV APVDPTPSTV LSLSSLDSQL FLRFPIEYLL VYASPHGVDR     60
AVTAARVKAA LARSLVPYYP LAGRVKTRPD STGLDVVCQA QGAGLLEAVS DYTASDFQRA    120
PRSVTEWRKL LLVEVFKVVP PLVVQLTWLS DGCVALGVGF SHCVIDGIGS SEFLNLFAEL    180
ATGRARLSEF QPKPVWDRHL LNSAGRTNLG THPEFGRVPD LSGFVTRFTQ ERLSPTSITF    240
DKTWLKELKN IAMSTSQPGE FPYTSFEVLS GHIWRSWARS LNLPAKQVLK LLFSINIRNR    300
VKPSLPAGYY GNAFVLGCAQ TSVKDLTEKG LGYCADLVRG AKERVGDEYA REVVESVSWP    360
RRASPDSVGV LIISQWSRLG LDRVDFGLGR PVQVGPICCD RYCLFLPVRE STESVKVMVA    420
VPTSAVDRYE YFIRSPYS                                                  438

SEQ ID NO: 21           moltype = DNA  length = 1392
FEATURE                 Location/Qualifiers
misc_feature            1..1392
                        note = Rh-AAT1
source                  1..1392
                        mol_type = genomic DNA
                        organism = Fragaria X ananassa
SEQUENCE: 21
atgcatcacc atcaccacca cgagaagatt gaggtttcca tcatctccag agacactatc      60
aagccttccg ctgcttcttc ttccttgcac ccatacaagt tgtccatcat cgaccagttc     120
actccaacta cttacctccc agttatcttc ttctcaccaa tcactgacag agttttcaac     180
ttgccacaga ctttgactga cttgaagaac actgttttcc caggctttga ctttgtaccac    240
ccattgtccg gtagaatcaa gaacaacttg tacatcgacg acttcgaggc tggtatccca     300
tacttggaag ctagagttaa cttccacatg atcgatttct tgagattgcc aaagatcgag     360
tggttgaacg agttcgttcc aatggctcca tacagaaaag agactatctc cgagttcttg     420
cctttgttgg gtatccaggt taacatcttc gactccgta tcgctatcgg tgtttcattc     480
tcccacaaga tcaacgacgg tcagactgct cctgtttct tgaagtcctg ggttgctatc     540
ttcagaggtt acagaaacaa gatcatccac ccaaacttgt cccaggctgc tttgttgttg     600
ccatccagag atgatttgcc agagaagtac gttgctatga tggaagaat gtggttcggt     660
gagaagaagg ttgttactag aagattcgtt tcgacgcta aggctatctc cgctttgcaa     720
gatgagggaa agtctgagta cgttccaaag ccttccaggt tcaagcttt gactggttcc     780
ttgtggaagc accagttggc tgcttctaga gctttgtcct ctggtactttc cactagattc     840
tccgttgctt cccagactgt taacttgaga tccaagatga acatgaagac tactttggac     900
aacgctatcg gaaatatctt cttgtgggct tccgctagat tggacttgaa cgatactgct     960
ccaggttcct ccgacttgaa gttgtgtgac ttggttaact gttgaacga atccatcaaa     1020
gagttcaact ccgattactt ggagatcttg aagggtaaag aggggttacgg tggtatgtgt    1080
```

```
gatttgttgg acttcatgga agagggttcc ttcgttgaac cagctccaga gttttactca   1140
ttctcctcat ggacaagatt cttcgaccag gttgatttcg gttggggtag accatcttgg   1200
gttggtttct ctggtagagt tgagactaga aacttcacta tcttcgttga gactcagtgt   1260
gacgacggta ttgacgcttg ggttactgtt gacgagaagc agatggctat gttggagcaa   1320
gacccacagt ttttggcttt cgcttctcca aacccaagaa tctctatcgc ttcctccgtt   1380
ggtatggact ag                                                         1392
```

| | | |
|---|---|---|
| SEQ ID NO: 22 | moltype = AA length = 463 | |
| FEATURE | Location/Qualifiers | |
| REGION | 1..463 | |
| | note = Rh-AAT1_AA | |
| source | 1..463 | |
| | mol_type = protein | |
| | organism = Fragaria X ananassa | |

```
SEQUENCE: 22
MHHHHHHEKI EVSIISRDTI KPSAASSSLH PYKLSIIDQF TPTTYFPVIF FYPITDRVFN    60
LPQTLTDLKN TVSQALTLYH PLSGRIKNNL YIDDFEAGIP YLEARVNFHM IDFLRLPKIE   120
WLNEFVPMAP YRKETISEFL PLLGIQVNIF DSGIAIGVSF SHKINDGQTA SCFLKSWVAI   180
FRGYRNKIIH PNLSQAALLL PSRDDLPEKY VAMMERMWFG EKKVVTRRFV FDAKAISALQ   240
DEGKSEYVPK PSRVQALTGF LWKHQLAASR ALSSGTSTRF SVASQTVNLR SKMNMKTTLD   300
NAIGNIFLWA SARLDLNDTA PGSSDLKLCD LVNLLNESIK EFNSDYLEIL KGKEGYGGMC   360
DLLDFMEEGS FVEPAPEFYS FSSWTRFFDQ VDFGWGRPSW VGFSGRVETR NFTIFVETQC   420
DDGIDAWVTV DEKQMAMLEQ DPQFLAFASP NPRISIASSV GMD                     463
```

| | | |
|---|---|---|
| SEQ ID NO: 23 | moltype = DNA length = 1458 | |
| FEATURE | Location/Qualifiers | |
| misc_feature | 1..1458 | |
| | note = CM-AAT4 | |
| source | 1..1458 | |
| | mol_type = genomic DNA | |
| | organism = Cucumis melo | |

```
SEQUENCE: 23
atgcatcacc atcaccacca cgaggttaag gttttgtcca aagagactat catcccatcc     60
tccccaactc caccacactt gcaaccattg aacttgtcac tggatcaact gtcgtcccca   120
atgttgtaca tccctttgtt gttgttctac ccaatgaaga agtcctacca gcaccaggat   180
cacaacaagg ctatcgctac tttgaaaact tccttgtcca agactttgtc agattctac    240
ttgttggctg gtagaatcat cggtaagtcc atccactgta acgacaaggg tgctgttttc   300
atggaagcta ctatcaactc caacatgttc gacatcttga agagcccaaa caacgaggtt   360
tgactaagt tgttgccatg ttcttttgttg tgtaacacta agcaatcga agagtaccca   420
cagatcgttg ttcaggctaa catcttcgaa tgtggtggta tcgctatctc cttgtgtttg   480
ttgcacaagt tgatcgacgc tgctactttc tgttgttct tgagatcctg ggctactaca   540
aacagagagt tgttgtcttt ggaccactct tccccaaaca acaatatggt ttgtgttgac   600
tacaagtcct tctcctcctt gttcccacaa acaaacttgt tgccttttcca ccagtcttg   660
atcaacaacg ataaggctgt tgttccacca tcctccatct ttaacagaaa gagaagattc   720
cagagattcg ttttcagatc cgaggctatc ttggacttga aggctaaggc taagtcctgt   780
gacatcccaa acccaacttg tgttgagact ttgacttgtt tcatctggaa gtacttgatg   840
aaggttgctg acgacggtga ctctcaaaga ccattcactc tgtcccacgt tgttaacatc   900
agaaagatgt tggagccatc cttgggtgag gtttctttgg gtaacatcat gtggggtact   960
gttgctcacc acttctccac tactagaaac gaagagttcg agggtttgga gttgtccaag  1020
ttggtttcct tgttgagaca gtccttcaag aagattaaca aggactacat caaagaattg  1080
atcatgggtg gtgacaaaga aaagagaaac gttgttatga gttggttgg tgagatcaat  1140
aagtggccaa tctccaacta ctacttcttc acttcctgga agaatttgaa gttgaacgag  1200
gttgacttcg gttggggtaa gccattgtgg tctgctattg ctggtgaccc aaacgagatg  1260
atgggaaaca ttatcgttt ggttgacaac gttttggacg acggttctac tgaggcttgg  1320
attttgttgg acgagaaaga gatgcagttg ttggagcaga tcccacagtt tttggagttc  1380
gctttgttga acccatccat caactcgcca cacaaccaga aaactgctga cgagattttc  1440
tccaacaaat tgatctaa                                                 1458
```

| | | |
|---|---|---|
| SEQ ID NO: 24 | moltype = AA length = 485 | |
| FEATURE | Location/Qualifiers | |
| REGION | 1..485 | |
| | note = CM-AAT4_AA | |
| source | 1..485 | |
| | mol_type = protein | |
| | organism = Cucumis melo | |

```
SEQUENCE: 24
MHHHHHHEVK VLSKETIIPS SPTPPHLQPL NLSLLDQLSP MLYIPLLLFY PMKKSYQHQD    60
HNKAIATLKT SLSKTLSRFY LLAGRIIGKS IHCNDKGAVF MEATINSNMF DILKEPNNEV   120
LTKLLPCSLL CNTKPIEEYP QIVVQANIFE CGGIAISLCL LHKLIDAATF CCFLRSWATT   180
NRELLSLDHS SPNNNMVCVD YKSFSSLFPQ TNLLPFHQSL INNDKAVVPP SSIFNRKRRF   240
QRFVFRSEAI LDLKAKAKSC DIPNPTCVET LTCFIWKYLM KVADDGDSQR PSTLSHVVNI   300
RKMLEPSLGE VSLGNIMWGT VAHHFSTTRN EEFEGLELSK LVSLLRQSFK KINKDYIKEL   360
IMGGDKERRN GVMKLVGEIN KWPISNYYFF TSWKNLKLNE VDFGWGKPLW SAIAGDPNEM   420
MGNIIVLVDN VLDDGSTEAW ILLDEKEMQL LEQIPQFLEF ALLNPSINLP HNQKTADEIF   480
SNKLI                                                               485
```

| | | |
|---|---|---|
| SEQ ID NO: 25 | moltype = DNA length = 669 | |
| FEATURE | Location/Qualifiers | |
| misc_feature | 1..669 | |

```
                    note           = ACT
source              1..669
                    mol_type       = genomic DNA
                    organism       = Staphylococcus sciuri
SEQUENCE: 25
atgcatcatc accatcacca caactttaat aaaattgatt tagacaattg gaagagaaaa   60
gagatattta atcattattt gaaccaacaa acgactttta gtataaccac agaaaattgat 120
attagtgttt tataccgaaa cataaaacaa gaaggtata aattttaccc tgcatttatt   180
ttcttagtga caagggtgat aaactcaaat acagcttata gaactggtta caatagcgac  240
ggagagttag gttattggga taagttagag ccacttttata caatttttga tggtgtatct 300
aaaacattct ctggtatttg gactcctgta aagaatgact tcaaagagtt ttatgattta  360
tacctttctg atgtagagaa atataatggt tcgggggaaat tgtttcccaa acacacctata 420
cctgaaaatg ctttttctct ttctattatt ccatggactt cattgactgg gttaactta   480
aatatcaata ataatagtaa ttaccttcta cccattatta cagcaggaaa attcattaat  540
aaaggtaatt caatatattt accgctatct ttacaggtac atcattcgt ttgtgatggt   600
tatcatgcag gattgtttat gaactctatt caggaattgt cagataggcc taatgactgg  660
cttttataa                                                           669

SEQ ID NO: 26       moltype = AA   length = 222
FEATURE             Location/Qualifiers
REGION              1..222
                    note           = ACT_AA
source              1..222
                    mol_type       = protein
                    organism       = Staphylococcus sciuri
SEQUENCE: 26
MHHHHHHNFN KIDLDNWKRK EIFNHYLNQQ TTFSITTEID ISVLYRNIKQ EGYKFYPAFI   60
FLVTRVINSN TAFRTGYNSD GELGYWDKLE PLYTIFDGVS KTFSGIWTPV KNDFKEFYDL  120
YLSDVEKYNG SGKLFPKTPI PENAFSLSII PWTSFTGFNL NINNNSNYLL PIITAGKFIN  180
KGNSIYLPLS LQVHHSVCDG YHAGLFMNSI QELSDRPNDW LL                     222

SEQ ID NO: 27       moltype = DNA   length = 1278
FEATURE             Location/Qualifiers
misc_feature        1..1278
                    note           = BanAAT
source              1..1278
                    mol_type       = genomic DNA
                    organism       = Fragaria X ananassa
SEQUENCE: 27
atgcatcacc accaccacca ttccttcgct gttactagaa cttccagatc cttggttacc   60
ccatgtggtg ttactccaac tggttctttg ggtttgtccg ccattgatag agtcccaggt  120
ttgagacaca tggtcagatc cttgcacgtt ttcagacaag gtagagagcc agccagaatc  180
atcagagaag ctttgtccaa ggccctggtc aagtactaca catttgctgg tagattcgtt  240
gacgatcctg aaggtggtgg tgaggttaga gttgcttgta ctggtgaagg tgcctggttc  300
gttgaagcta aggctgactg tttctttgga gacgtcaagt acttggacct gccattgatg  360
attccagagg acgctttgtt gccaaagcca tgtccaggtt tgaacccatt ggacttgcct  420
ttgatgttgc aggttaccga gtttgtcggt ggtggttttc ttgttggttt gatctccgtt  480
cacactatcg ctgacggttt gggtgttgtc cagttcatta cgctgttgc tgagatcgct   540
agaggtttgc caaagcctac tgttgaacca gcttggtcca gagaggttat tccaaaccca  600
ccaaagttgc caccaggtgg tccaccagtt tttccatcct ttaagttgtt gcacgccacc  660
gttgatttgt cccagatca cattgaccac gtcaagtca gacacttgga gttgactggt   720
cagatgttt ccactttcga cgttgctatc gctaacttgt ggcagtccag aactagagcc  780
attaacttgg atccaggtgt tgacgtccac gtctgtttct tcgctaacac cagacacttg  840
ttgagacagg tcgttttgtt gccaccagag gatggttact acggtaactg ttcctaccca  900
gttactgcta ctgctccctc cggtagaatt gcttctgctg agttgattga cgtcgtgtcc  960
atcatcagag atgccaagtc tagattgcca ggtgagtttg ctaaatgggc tgctggtgat 1020
ttcaaggacg acccataca gttgtccttt acctacaact ccctgttcgt ttccgactgg  1080
actagattgg gtttcttgga cgttgattac ggttggggta agccattgca cgttatccca  1140
ttcgcttact ggacatcat ggccgttggt attattggtg ctccaccagc tccacaaaag  1200
ggtactagag ttatggctca gtgcgtcgag aaagaacaca tgcaagcttt cttggaagag 1260
atgaagggtt tcgcttaa                                                1278

SEQ ID NO: 28       moltype = AA   length = 425
FEATURE             Location/Qualifiers
REGION              1..425
                    note           = BanAAT_AA
source              1..425
                    mol_type       = protein
                    organism       = Fragaria X ananassa
SEQUENCE: 28
MHHHHHHSFA VTRTSRSLVT PCGVTPTGSL GLSAIDRVPG LRHMVRSLHV FRQGREPARI   60
IREALSKALV KYYPFAGRFV DDPEGGGEVR VACTGEGAWF VEAKADCSLE DVKYLDLPLM  120
IPEDALLPKP CPGLNPLDLP LMLQVTEFVG GFVVGLISV HTIADGLGVV QFINAVAEIA   180
RGLPKPTVEP AWSREVIPNP PKLPPGGPPV FPSFKLLHAT VDLSPDHIDH VKSRHLELTG  240
QRCSTFDVAI ANLWQSRTRA INLDPGVDVH VCFFANTRHL LRQVVLLPPE DGYYGNCFYP  300
VTATAPSGRI ASAELIDVVS IIRDAKSRLP GEFAKWAAGD FKDDPYELSF TYNSLFVSDW  360
TRLGFLDVDY GWGKPLHVIP FAYLDIMAVG IIGAPPAPQK GTRVMAQCVE KEHMQAFLEE  420
MKGFA                                                               425
```

| SEQ ID NO: 29 | moltype = DNA   length = 1299 |
|---|---|
| FEATURE | Location/Qualifiers |
| misc_feature | 1..1299 |
| | note = Glossy2 |
| source | 1..1299 |
| | mol_type = genomic DNA |
| | organism = Zea mays |

SEQUENCE: 29

```
atgcatcatc accaccacca cgttttcgaa caacacgaag aagaggctgt tgctccaggt   60
gctgttcatg gtcatagatt gtctaccgtt gttccatcct ccgttactgg tgaagttgac  120
tacgctttgg ctgatgctga cttggctttc aagttgcact acctgagagg tgtctactac  180
tacagatctg gtgacggttt ggccaccaag gttttgaagg atccaatgtt gccatggctg  240
gatgaccact ttccagttgc tggtagagtt agaaggctg aaactgaagg tgatggtgct  300
ccaagacgtc cttacatcaa gtgtaacgac tgcggtgtta gaatcgttga ggccagatgt  360
gatagagaca tggctgagtg gattagagat gctgctccag gtagaatcag acagttgtgt  420
tacgacaagt tcttgggtcc agagttgttc ttctccccat gctgtacgt tcagatcacc  480
aacttcaagt gtggtggttt ggcttgggt ttctcttggg ctcacttgat tggtgacatt  540
ccatccgctg ctacctgctt taacaagtgg gctcaaatcc tgtccggtaa gaagccagaa  600
gctactgttt tgactccacc aaaccagcca ttgcaaggtc aatctccagc tgctccaaga  660
tccgttaagc aggttggtcc aattgaggac ttgtggttgg ttccagctgg tagagatatg  720
gcctgttact ctttccacgt ttccgacgcc gttttgaaga agttgcacca acaacagaac  780
ggtagacagg atgctgctgc tggtactttc gaattgattc ccgctttggt ttggcaggct  840
gttgctaaga ttagaggtga cgttgacacc gttaccgttg ttagagctga tgctgctggt  900
agatctggta agtcttggc caacgagatg aaggttggtt acgttgaatc tgctggatcc  960
tccccagcta agactgattt ggctgaattg gctgctttgc tggccaagaa cttgttgac  1020
gaaactgctg ctgttgctgc tttccaaggt gacgttttgg tttacggtgg tgccaacttg  1080
accttggttg acatggaaca ggttgacctg tacggttttg agatcaaggg tcaaagacca  1140
gttcacgtcg aatacggtat ggatggtgtt ggtgatgagg gtgctgtttt ggttcaacca  1200
gatgctgatg gtagaggtag attggttact gccgttttgc caggtgacga gattgactct  1260
ttgagagctg cttttgggtct cgccttgcag gttgcttaa               1299
```

| SEQ ID NO: 30 | moltype = AA   length = 432 |
|---|---|
| FEATURE | Location/Qualifiers |
| REGION | 1..432 |
| | note = Glossy2_AA |
| source | 1..432 |
| | mol_type = protein |
| | organism = Zea mays |

SEQUENCE: 30

```
MHHHHHHVFE QHEEEAVAPG AVHGHRLSTV VPSSVTGEVD YALADADLAF KLHYLRGVYY   60
YRSGDGLATK VLKDPMLPWL DDHFPVAGRV RRAETEGDGA PRRPYIKCND CGVRIVEARC  120
DRDMAEWIRD AAPGRIRQLC YDKVLGPELF FSPLLYVQIT NFKCGGLALG FSWAHLIGDI  180
PSAATCFNKW AQILSGKKPE ATVLTPPNQP LQGQSPAAPR SVKQVGPIED LWLVPAGRDM  240
ACYSFHVSDA VLKKLHQQQN GRQDAAAGTF ELVSALVWQA VAKIRGDVDT VTVVRADAAG  300
RSGKSLANEM KVGYVESAGS SPAKTDLAEL AALLAKNLVD ETAAVAAFQG DVLVYGGANL  360
TLVDMEQVDL YGLEIKGQRP VHVEYGMDGV GDEGAVLQP DADGRGRLVT AVLPGDEIDS  420
LRAALGSALQ VA                                                     432
```

| SEQ ID NO: 31 | moltype = DNA   length = 1398 |
|---|---|
| FEATURE | Location/Qualifiers |
| misc_feature | 1..1398 |
| | note = CM-AAT3 |
| source | 1..1398 |
| | mol_type = genomic DNA |
| | organism = Cucumis melo |

SEQUENCE: 31

```
atgcatcatc atcaccacca cgcatcctcc ctggttttcc aagttcaaag atcccagcca   60
cagttgattc caccatctga tccaactcca cacgagttca agcagttgtc tgacattgac  120
gaccaagagg gtctgagatt ccagatccca gttatccagt tctacagaca cgaccccaaga  180
atggctggta ctgatccagc cagagttatc aaagaggcta tcgctaaggc cctggttttc  240
tactacccat cgctggtag attgagagag ggtccaggta gaaagttgtt cgttgagtgt  300
actggtgagg gtgtcatgtt cattgaagct gacgctgacg tttccttgga gcaatttggt  360
gatgcattgc agccaccatt cccatgtttg gaggaacctt tgttcgacgt tccaaactcc  420
tctggtgttt tggactgtcc attgctgttg atccaggtca ccagattgaa gtgcggtagt  480
ttcatcttcg ccttgagatt gaaccacact atgtctgacg cttccggttt ggtccaattc  540
atgatggctg ttggtgagat ggctagagt gctactgctc catctgttag accagtttgg  600
cagagagctt tgctgaacgc tagagatcca ccaaaggtta cctgtcacca cagagaatac  660
gacgaggttg ttgacaccaa gggtactatc attccattgg acgacatggc ccagatgcc  720
ttttttttcg gtccatccga aatctccgcc atcagaaagt ctttgccatc ccacttgaga  780
cagtgttcct cattcgaggt tttgaccgct tgtctgtggc gttcagaac tatttccttg  840
caaccagacc cagaggaaga ggttagagtt ttgtgtatcg tcaactccag atccaagttc  900
aacccaccat tgccaactgg ttactacggt aacgctttcg ctttcccagt tgctttgact  960
actgccggta agtgtgtca gaacccattg ggttacgcct tggagttggt tagaaaggct 1020
aagtcctgtg tcaccgagga ctacatgaag tctgttgctg acttgatgat catcaaggt 1080
agaccacact tcaccgttgt cagaacctac tggtttccgc acgttactag agctggtttc 1140
gaggatgttg attccggttg gggtaaggct atgtacggtg tccagctaa aggtggtgtt 1200
ggtgctattc caggtgttgc ctcttttctac atcccattca agaacaagaa gggcgagaga 1260
ggtatccttg tcccatttgtg tttaccagct ccagccatgg aagattcgt caaagaattg 1320
gacgccttgc tgaaggctgg taagactatt gatggtgtcg caacaagaa gccctgttc  1380
```

```
attgcttccg ccttgtaa                                                  1398

SEQ ID NO: 32          moltype = AA  length = 465
FEATURE                Location/Qualifiers
REGION                 1..465
                       note = CM-AAT3_AA
source                 1..465
                       mol_type = protein
                       organism = Cucumis melo
SEQUENCE: 32
MHHHHHHASS LVFQVQRSQP QLIPPSDPTP HEFKQLSDID DQEGLRFQIP VIQFYRHDPR    60
MAGTDPARVI KEAIAKALVF YYPFAGRLRE GPGRKLFVEC TGEGVMFIEA DADVSLEQFG    120
DALQPPFPCL EEPLFDVPNS SGVLDCPLLL IQVTRLKCGG FIFALRLNHT MSDASGLVQF    180
MMAVGEMARG ATAPSVRPVW QRALLNARDP PKVTCHHREY DEVVDTKGTI IPLDDMAHRS    240
FFFGPSEISA IRKALPSHLR QCSSFEVLTA CLWRFRTISL QPDPEEEVRV LCIVNSRSKF    300
NPPLPTGYYG NAFAFPVALT TAGKLCQNPL GYALELVRKA KADVTEDYMK SVADLMVIKG    360
RPHFTVVRTY LVSDVTRAGF EDVDFGWGKA MYGGPAKGGV GAIPGVASFY IPFKNKKGER    420
GILVPLCLPA PAMERFVKEL DALLKAGKTI DGVDNKKPLF IASAL                    465

SEQ ID NO: 33          moltype = DNA  length = 1464
FEATURE                Location/Qualifiers
misc_feature           1..1464
                       note = BAHDFox
source                 1..1464
                       mol_type = genomic DNA
                       organism = Fragaria X ananassa
SEQUENCE: 33
atgcatcatc accatcacca cccatccact ttgaacttcc aatccgagac tccaactgtt    60
caaggtgaac aagacccatc cttggttacc ttggaacact acggattgca accaccatcc    120
gctcaacaaa agttgacccc attggacatg aacatgccaa gactgtacgg tatcagactg    180
atcttgtgct tcccaactaa cccaggtatg gacaagagac agatctacga gaacctgaag    240
aagggtttgg ctcacaccgt tacttccgtt ccatggattt ctggtcacat cggtccagaa    300
gaaggtcagg atccaaagac cagaaaggtc cagattttgg actccccata cggtttcaga    360
ttcccataca aggacttgac tgacgcctca ccaccagctg aattgcaaga gaaagaaac     420
ttcccactgg ctgagttcac tactgctcag gttggtccaa tgacgttat gccacaaggt     480
ccaaaccagc cagttttgc tgctcaggct aacttcgtta agggtggttt gttgttgacc     540
gttggtgttc accactctgc ttgtgatgct ttggctttgg acgctatctt gtctacttgg    600
tcccacaaca ctgctgttgc ttcaggtggt tctggttcct tctctacttt ggacggtcca    660
tctaacgaca gatccccatt gatggaaggt gacttgggta acgctgatgt tgctgcttc     720
cctgagtacg ttttgatgcc aactccacac tctactgagg gtgacttgtc ctctatgtcc    780
ggttttcaaa tgccaccatt ggcctctaga ctgttccact tctaccagag gtccctgaga    840
aagttgaagg ctgaagctgg tgctttctct tctcacgatg ctttgtgtgc tttcatctgg    900
cagagaatga cctgcggctag aatgcactcc ggtatctca gagatcacc aggtgacttg    960
acctccagat tctgtttcgc cgtcaacatc agaaacagaa tgtccccacc attgccacca   1020
tcctacatgg gtaatgcttc catgggttgt gtcaccgaga gatttctgt tgcctccatg   1080
atctccaaca acgtttgaa gcaagcctcc gtcactatca gaagatccct gaacgatttc   1140
aactcccaa gaagggctac ttccaccatc ggttgttca gatctagacc agacccaacc   1200
gacttcaagt tgtccttcaa cggtttcttg gtccagacg ttgttgaatc ttcttgggct   1260
gacttgggtg tttacggtca tcaatggggt gacgctattg gtactttga cgctgttaga   1320
atcccaggtg aaggttctga cggtactatg atgatcctgc caagattgaa ggacggtggt   1380
ttggacgttg ttgttggttt gtctactgct gccatgaaa gactgttga ggacgaaaag    1440
ttcgtttccg ttgctcactc ttaa                                         1464

SEQ ID NO: 34          moltype = AA  length = 487
FEATURE                Location/Qualifiers
REGION                 1..487
                       note = BAHDFox_AA
source                 1..487
                       mol_type = protein
                       organism = Fragaria X ananassa
SEQUENCE: 34
MHHHHHHPST LNFQSETPTV QGEQDPSLVT LEHYGLQPPS AQQKLTPLDM NMPRLYGIRL    60
ILCFPTNPGM DKRQIYENLK KGLAHTVTSV PWISGHIGPE EGQDPKTRKV QILDSPYGFR    120
FPYKDLTDAL PPYAELQERN FPLAEFTTAQ VGPIDVMPQG PNQPVFAAQA NFVKGGLLLT    180
VGVHHSACDA LALDAILSTW SHNTAVASGG SGSFSTLDGP SNDRSPLMEG DLGNADVAAF    240
PEYVLMPTPH STEGDLSSMS GFQMPPLASR LFHFSPESLR KLKAEAGAFS SHDALCAFIW    300
QRMTLARMHS GIFNDPPGDL TSRFCFAVNI RNRMSPPLPP SYMGNASMGC VTEKISVASM    360
ISNNGLKQAS VTIRRSLNDF NSPRRATSTI GLLRSRPDPT DFKLSFNGFL GPDVVESSWA    420
DLGVYGHQWG DAIGTLDAVR IPGEGSDGTM MILPRLKDGG LDVVVGLSTA AMERLLEDEK    480
FVSVAHS                                                              487

SEQ ID NO: 35          moltype = DNA  length = 1410
FEATURE                Location/Qualifiers
misc_feature           1..1410
                       note = VpAAT1
source                 1..1410
                       mol_type = genomic DNA
                       organism = Vasconcellea pubescens
SEQUENCE: 35
```

```
atgcatcatc accaccacca tgctgaaaag gcctcttctc tgatgttcaa cgttagaagg    60
cacgagccag agttgatcac tccagctaaa cctactccaa gagagatcaa gttgctgtcc   120
gacattgatg accaggacgg tttgagattc caggtcccaa ttatccagtt ctacaagaac   180
aactcctcca tgcagggtaa gaacccagcc aagattatca agtctgcttt ggccgagact   240
ctggtccatt actatccatt ggctggtaga ctgagagagg gtttcggtag aaagttgatg   300
gttgagtgta ccggtgaggg tatcttgttc attgaagctg atgccgacgt taccttgcac   360
gaatttggtg atgatctgcc accaccattc ccatgtttgg tcgagttgtt gtacgacgtt   420
ccaggttcct ccggtattat cgacactcca ttgctgttga tccaggtcac cagattgaag   480
tgccgtggtt tcatcttcgc cttgagattg aaccacacta tgtctgacgc ttccggtttg   540
gttcagttca tgactgctgt tggtgagatg gctagaggtc aaagatcctt gtccattcag   600
ccagtttggg agagacactt gttgaacgct agagatccac caagagttac ccacattcac   660
cacgaatacg atgacttgga ggacaccaag ggtactatca ttccattgga cgacatggtc   720
cacaggtcct ttttttcgg tccatccgaa atggccgcca tcaagagatt ggttccagct   780
cactttcaca gatccactac ctccgaagtt ttgaccgtct acttgtggcg ttgttacact   840
attgccttgc aaccagaccc agaggaagag atgagagtta tctgtgtcgt caactccagg   900
accaagttga acccaccatt gccaactggt tctacggta acggtattgc tttcccagct   960
gctatctccc aggctaagaa gatttgcgaa accccattcg ttacaccct gcagttggtt  1020
aagcgacca aggttgacgt taccgaagag tacatgaagc ccgctgctga cttgatggct  1080
atgaagggta gaccacactt caccgtcgtt agaaggtaca tggtttccga cgttactaga  1140
gccggtttcg gtttggttga tttcggttgg ggtagaccag aaccagttta tggtggtcca  1200
gctaaggggtg tgttggtcc aattccaggt gttacctcat tcttcgtccc attcaagaac  1260
agaaagggtg agaagggtat cgttgtccca acttgtttgc caactccagc catggaaaga  1320
ttcgccaagt tgatgaacga gatcctgcag aaccagttgt tggtttccgc tgaagagaac  1380
aagtccgtgt tcatcgtttc cgctatctaa                                  1410

SEQ ID NO: 36           moltype = AA   length = 469
FEATURE                 Location/Qualifiers
REGION                  1..469
                        note = VpAAT1_AA
source                  1..469
                        mol_type = protein
                        organism = Vasconcellea pubescens
SEQUENCE: 36
MHHHHHHAEK ASSLMFNVRR HEPELITPAK PTPREIKLLS DIDDQDGLRF QVPIIQFYKN    60
NSSMQGKNPA KIIKSALAET LVHYYPLAGR LREGFGRKLM VECTGEGILF IEADADVTLH   120
EFGDDLPPPF PCLVELLYDV PGSSGIIDTP LLLIQVTRLK CGGFIFALRL NHTMSDASGL   180
VQFMTAVGEM ARGQRSLSIQ PVWERHLLNA RDPPRVTHIH HEYDDLEDTK GTIIPLDDMV   240
HRSFFFGPSE MAAIRRLVPA HFHRSTTSEV LTAYLWRCYT IALQPDPEEE MRVICVVNSR   300
TKLNPPLPTG FYGNGIAFPA AISQAKKICE NPFGYTLQLV KQTKVDVTEE YMRSAADLMA   360
MKGRPHFTVV RRYMVSDVTR AGFGLVDFGW GRPEPVYGGP AKGGVGPIPG VTSFFVPFKN   420
RKGEKGIVVP TCLPTPAMER FAKLMNEILQ NQLLVSAEEN KSVFIVSAI              469

SEQ ID NO: 37           moltype = DNA   length = 1368
FEATURE                 Location/Qualifiers
misc_feature            1..1368
                        note = AMAT
source                  1..1368
                        mol_type = genomic DNA
                        organism = Vitis labrusca
SEQUENCE: 37
atgcatcatc accaccatca cgcttctcca tcttccccat tggttttctc cgttaacaga    60
tgcgttcccc agatcgttag accagctaac ccaactccaa gagaggttaa gcagttgtcc   120
gacattgacg accaagaggg tagaagattc cagatcccag tcatcatgtt ctacagaaac   180
aacccctga tggaaggtaa ggacccagtt aaggttatca gagaggcttt gggtaaggcc   240
ctggtttact actacccatt cgctggtaga ttgatcgagg gtgacaacag aaagttgatg   300
gttgactgta ccggtgaggg tgtcttgttc attgaagctg atgctgacac caccttggag   360
aacttgggtg atgctattca gccaatgtgt ccatgcttcg aggaattgct gtacgacgtt   420
ccaggttcca ctactatttt gggttcccca ttgatcctga tccaggtcac cagattgaga   480
tgcggtggtt tcatcttcgc cttgagattg aaccacacta tgtctgacgc tgccggtttg   540
attcagttct tggacactat tggtgagatg gcccaaggtt tgtctgtccc atctttgttg   600
ccaatctggc agagagagtt gctgaacgct agaaacccac aagaatcac agaatccac   660
cacgaatacg agaaggtcac taacaccaag ggtactctga tggctatgga cgaaaactcc   720
ttggtccaca ggtcattttt cttcggtaga gaagagatca gggccctgcg taatagattg   780
ccagcttctt tgggtgcttg ttccacctc gaagtttgt tggcctgtgt ttggagattg   840
agaactatcg ctttcgctgt tgacccagac gaggttgtta gaatctcctg catcatcaac   900
atgagaggta agcacggttt cgagttgcca ccaggttact acgtaacgc ttttgttact   960
ccagcctcca tcactaaggc cggtatgttg tgtaagaacc cattggagtt cgccatcaga  1020
ctggtcaaga aagctaaggc tgaaatgtcc caagatgaca tcaagtccgt tgccgacttg  1080
atggtcatca agggtagacc tttgttcacc cagccaggta acttcactgt ttccgacgtt  1140
actagagctg gtttgggtga agttgattc ggttggggta agccagttta cggtggtgtt  1200
gctagagctt gtccaatcat ctccttcaga atgctgttca gaaactccaa gggtgaagag  1260
ggttccgtta tccaatttg gttgccacca ccagtcatgg aaagattcga gcaagagctg  1320
aagagaatga ccaagaaggc cgagttgttg atcacctcca tgttgtaa              1368

SEQ ID NO: 38           moltype = AA   length = 455
FEATURE                 Location/Qualifiers
REGION                  1..455
                        note = AMAT_AA
source                  1..455
```

```
                            mol_type = protein
                            organism = Vitis labrusca
SEQUENCE: 38
MHHHHHASP  SSPLVFSVNR  CVPQIVRPAN  PTPREVKQLS  DIDDQEGRRF  QIPVIMFYRN   60
NPLMEGKDPV  KVIREALGKA  LVYYYPFAGR  LIEGDNRKLM  VDCTGEGVLF  IEADADTTLE  120
NLGDAIQPMC  PCFEELLYDV  PGSTTILGSP  LILIQVTRLR  CGGFIFALRL  NHTMSDAAGL  180
IQFLDTIGEM  AQGLSVPSLL  PIWQRELLNA  RNPPRITRIH  HEYEKVTNTK  GTLMAMDENS  240
LVHRSFFFGR  EEIRALRNRL  PASLGACSTF  EVLMACVWRC  RTIAFAVDPD  EVVRISCIIN  300
MRGKHGFELP  PGYYGNAFVT  PASITKAGML  CKNPLEFAIR  LVKKAKAEMS  QEYIKSVADL  360
MVIKGRPLFT  QPGNFTVSDV  TRAGLGEVDF  GWGKPVYGGV  ARACPIISFR  MLFRNSKGEE  420
GSVIPIWLPP  PVMERFEQEL  KRMTKKAELL  ITSML                               455

SEQ ID NO: 39               moltype = DNA   length = 1341
FEATURE                     Location/Qualifiers
misc_feature                1..1341
                            note = Pun1
source                      1..1341
                            mol_type = genomic DNA
                            organism = Fragaria X ananassa
SEQUENCE: 39
atgcatcatc accaccaca cgcttttgct ttgccatctt ctttggtttc cgtctgcaac   60
aagtcctta tcaagccatc ctcctgacc ccatcgacct tgagatttca caagctgtcc  120
ttcatcgacc agtccctgtc caacatgtac atcccatgtg cattcttcta ccccaaggtc  180
caacaaagat tggaggactc taagaactcc gacgagttgt ctcacattgc ccacttgttg  240
caaacttccc tgtcccagac tctggttttcc tactaccat cgctggtaa gttgaaggac  300
aacgctaccg ttgactgtaa cgacatgggt gctgagttct tgtccgtcga aatcaagtgt  360
tccatgtccg agattttgga ccacccacat gcttctctgg ctgagtctat cgttttgcca  420
aaggatttgc catgggccaa caactgtgaa ggtggtaact tgttggttgt ccaggtgtcc  480
aagttcgact gtggtggtat tgctatctcc gtttgcttct cccacaagat cggtgacggt  540
tgttccttgt tgaacttctt gaacgactgg tcctccgtca ctagagatca cactactacc  600
actttggtcc catccccaag attcgttggt gactctgttt ctccacccca gaagtacggt  660
tccttgatca ctccacagat cctgtctgac ttgaaccagt gtgtccagaa gagactgatc  720
ttcccaactg acaagttgga cgctttgaga gctaaggttg ctgaagagtc cggtgttaag  780
aacccaacta gagctgaagt tgtctccgcc ttgttgttca agtgtgctac taaggcttcc  840
tcctccatgt tgccatctaa gttggtccac tttctgaaca tcaggaccat gatcaagcca  900
agattgccaa gaaacgccat cggtaacttg tcctccattt tctccattga ggccaccaac  960
atgcaggaca tggaattgcc aaccttggtc agaaacctga aaagaggt tgaggtcgcc 1020
tacaagaagg accaagttga gcagaacgag ctgatcttgg aagttgtcga atccatgaga 1080
gagggtaagc tgccattcga aaacatggac ggttacaaga acgtctacac ctgttccaac 1140
ctgtgcaagt accccttacta caccgttgat ttcggttggg gtagaccaga gagagtttgt 1200
ttgggtaacg gtccatccaa gaacgcattc tttctgaagg actacaaggc cggtcaaggt 1260
gttgaagcca gagttatgtt gcacaagcaa cagatgtccg agttcgagag aaacgaagag 1320
ttggtcgagt tcattgctta a                                             1341

SEQ ID NO: 40               moltype = AA   length = 446
FEATURE                     Location/Qualifiers
REGION                      1..446
                            note = Pun1_AA
source                      1..446
                            mol_type = protein
                            organism = Fragaria X ananassa
SEQUENCE: 40
MHHHHHHAFA  LPSSLVSVCN  KSFIKPSSLT  PSTLRFHKLS  FIDQSLSNMY  IPCAFFYPKV   60
QQRLEDSKNS  DELSHIAHLL  QTSLSQTLVS  YYPYAGKLKD  NATVDCNDMG  AEFLSVRIKC  120
SMSEILDHPH  ASLAESIVLP  KDLPWANNCE  GGNLLVVQVS  KFDCGGIAIS  VCFSHKIGDG  180
CSLLNFLNDW  SSVTRDHTTT  TLVPSPRFVG  DSVFSTQKYG  SLITPQILSD  LNQCVQKRLI  240
FPTDKLDALR  AKVAEESGVK  NPTRAEVVSA  LLFKCATKAS  SSMLPSKLVH  FLNIRTMIKP  300
RLPRNAIGNL  SSIFSIEATN  MQDMELPTLV  RNLRKEVEVA  YKKDQVEQNE  LILEVVESMR  360
EGKLPFENMD  GYKNVYTCSN  LCKYPYYTVD  FGWGRPERVC  LGNGPSKNAF  FLKDYKAGQG  420
VEARVMLHKQ  QMSEFERNEE  LVEFIA                                          446

SEQ ID NO: 41               moltype = DNA   length = 1401
FEATURE                     Location/Qualifiers
misc_feature                1..1401
                            note = Dv3MaT
source                      1..1401
                            mol_type = genomic DNA
                            organism = Fragaria X ananassa
SEQUENCE: 41
atgcatcatc accaccaca cgacaacatc ccaaacttga ctattttgga gcactccaga   60
atctccccac caccatctac tattggtcac agatccttgc ctctgacctt cttcgatatc  120
gcctggttgt tgtttccacc agtccaccac ttgtacttct accacttccc atactccaag  180
tcccacttca ccgagactgt tatccctaac ttgaagcact cctgtccat caccttgcag  240
cactacttca cattcgtcgg taagctgatc gtctacccaa acccacacga ctctactaga  300
aagccagaga tcagacacgg tgagggtgac tctgttgctt tgactttcgc tgagactacc  360
ctggacttca acgactgtc tgctaaccac ccaagaaagt gcgagaactt ctacccattg  420
gttccaccat tgggtaacgc tgtcaaagag tccgactacg ttaccttgcc agttttctcc  480
gttcaggtca cctacttccc aaaactccggt atttccatcg gtttgactaa ccaccactct  540
ttgtccgacg ctaacaccag attcggtttc ttgaaggctt gggcttccgt tgtgaaact  600
```

-continued

```
ggtgaggatc agccattcct gaagaacggt tctccaccag ttttcgacag agttgttgtc   660
aacccacagc tgtacgagaa cagattgaac cagaccagac tgggtacttt ctaccaagct   720
ccttccttgg ttggttcctc atccgataga gttagagcca ctttcgtttt ggccagaact   780
cacatctccg gtttgaagaa gcaggtcttg actcagttgc caatgttgga gtacacctct   840
tccttcaccg ttacctgtgg ttacatctgg tcctgtatcg tcaagtcctt ggtcaacatg   900
ggtgagaaga agggtgagga cgaattggag caattcatcg tttccgttgg ttgcagatcc   960
agattggatc cacctttgcc agagaactac ttcggtaact gttccgcccc atgtatcgtc  1020
actatcaaga acggtgttct gaaggggtgag aacggtttcg ttatggctgc taagttgatc  1080
ggtgagggta tctccaagat ggtcaacaag aagggtggta tcttggagta cgctgacaga  1140
tggtacgacg gtttcaagat cccagctaga aagatggata tctccggtac tccaaagctg  1200
aacttctacg acattgactt cggttggggt aaggccatga agtacgaggt tgtttctatc  1260
gactactccg cctctgtttc cttgtccgct tgtaaagaat ccgctcagga cttcgagatc  1320
ggtgtttgtt tcccatccat gcagatggaa gccttcggta gattttcaa cgacggtttg  1380
gagtccgcta tcgcttctta a                                             1401
```

```
SEQ ID NO: 42           moltype = AA  length = 466
FEATURE                 Location/Qualifiers
REGION                  1..466
                        note = Dv3MaT_AA
source                  1..466
                        mol_type = protein
                        organism = Fragaria X ananassa
SEQUENCE: 42
MHHHHHHDNI PNLTILEHSR ISPPPSTIGH RSLPLTFFDI AWLLFPPVHH LYFYHFPYSK   60
SHFTETVIPN LKHSLSITLQ HYFPPFVGKLI VYPNPHDSTR KPEIRHVEGD SVALTFAETT  120
LDFNDLSANH PRKCENFYPL VPPLGNAVKE SDYVTLPVFS VQVTYFPNSG ISIGLTNHHS  180
LSDANTRFGF LKAWASVCET GEDQPFLKNG SPPVFDRVVV NPQLYENRLN QTRLGTFYQA  240
PSLVGSSSDR VRATFVLART HISGLKKQVL TQLPMLEYTS SFTVTCGYIW SCIVKSLVNM  300
GEKKGEDELE QFIVSVGCRS RLDPPLPENY FGNCSAPCIV TIKNGVLKGE NGFVMAAKLI  360
GEGISKMVNK KGGILEYADR WYDGFKIPAR KMGISGTPKL NFYDIDFGWG KAMKYEVVSI  420
DYSASVSLSA CKESAQDFEI GVCFPSMQME AFGKIFNDGL ESAIAS                 466
```

```
SEQ ID NO: 43           moltype = DNA  length = 1326
FEATURE                 Location/Qualifiers
misc_feature            1..1326
                        note = NtHCT
source                  1..1326
                        mol_type = genomic DNA
                        organism = Fragaria X ananassa
SEQUENCE: 43
atgcatcatc accaccacca caagatcgag gtcaaagaat ccaccatggt taagccagct   60
gctgagactc cacaacagag attgtggaac tccaacgttg acttggtcgt cccaaacttc  120
cacactccat ccgtctactt ctacagacca actggttccc caaacttcttc tgacggtaag  180
gtttttgaaag aggccttgtc caaggctctg gttccatttt atccaatggc cggtagactg  240
tgcagagatg aggatggtag aatcgagatc gactgtaagg gtcagggtgt tttgttcgtt  300
gaagctgaat ccgacggtgt tgatgatgac ttcggtgatt tcgctccaac cttggagttg  360
agacagttga ttccagctgt tgactactcc cagggtactc agtcttacgc cttgttggtc  420
ttgcagatca cccactttaa gtgtggtggt gtttccttgg gtgttggtat gcaacatcat  480
gctgctgatg gtgcttccgg tctgcacttt attaacactt ggtccgacat ggccagaggt  540
ttggacttga ctattccacc attcatcgac agaaccctgc tgagagctag agatccacca  600
caaccacaat tcccacacgt tgaataccaa ccaccaccaa ccttgaaggt tactccagga  660
aacactccaa tctccgaagc tgttccagaa acctccgttt ccatcttcaa gctgaccaga  720
gatcagatca caccttgaa ggccaagtcc aaagaggacg gtaataccgt taactactcc  780
tcctacgaga gtgttggctgg tcacgtttgg agatccactt gtatggctag aggattggct  840
cacgaccaag agactaagtt gtacattgct accgacggta gatccagatt gaggccatct  900
ttgccaccag gttacttcgg taacgttatc ttcactacta ccccaatcgc tgttgctggt  960
gacattcagt ctaagccaat ttggtacgct gcctccaagt gcatgatgc tttggctaga 1020
atggacaacg actacttgag atccgccttg gactacttgg aattgcagcc agatttgaag 1080
gccttggtta gaggtgctca caccttcaag tgtccaaact tgggtattac tccctggtcc 1140
agattgccaa ttcacgatgc tgatttcggt tggggtagac aatttcat gggtccaggt 1200
ggtattgcct acgagggttt gtctttcatt ctgccatctc caactaacga cggttcccag 1260
tctgttgcta tttccttgca agctgagcac atgaagctgt tcgagaagtt cctgtacgac 1320
ttctaa                                                            1326
```

```
SEQ ID NO: 44           moltype = AA  length = 441
FEATURE                 Location/Qualifiers
REGION                  1..441
                        note = NtHCT_AA
source                  1..441
                        mol_type = protein
                        organism = Fragaria X ananassa
SEQUENCE: 44
MHHHHHHKIE VKESTMVKPA AETPQQRLWN SNVDLVVPNF HTPSVYFYRP TGSPNFFDGK   60
VLKEALSKAL VPFYPMAGRL CRDEDGRIEI DCKGQGVLFV EAESDGVVDD FGDFAPTLEL  120
RQLIPAVDYS QGIQSYALLV LQITHFKCGG VSLGVGMQHH AADGASGLHF INTWSDMARG  180
LDLTIPPFID RTLLRARDPP QPQFPHVEYQ PPPTLKVTPE NTPISEAVPE TSVSIFKLTR  240
DQINTLKAKS KEDGNTVNYS SYEMLAGHVW RSTCMARGLA HDQETKLYIA TDGRSRLRPS  300
LPPGYFGNVI FTTTPIAVAG DIQSKPIWYA ASKLHDALAR MDNDYLRSAL DYLELQPDLK  360
ALVRGAHTFK CPNLGITSWS RLPIHDADFG WGRPIFMGPG GIAYEGLSFI LPSPTNDGSQ  420
```

SVAISLQAEH MKLFEKFLYD F                                                         441

SEQ ID NO: 45           moltype = DNA  length = 1341
FEATURE                 Location/Qualifiers
misc_feature            1..1341
                        note = DBATAca
source                  1..1341
                        mol_type = genomic DNA
                        organism = Fragaria X ananassa
SEQUENCE: 45
atgcatcatc accatcacca cgctggttct accgagttcg ttgttagatc cttggagaga   60
gttatggttg ctccatctca accatcccca aaggctttct tgcagttgtc cactttggac  120
aacttgccag gtgtcagaga gaacatcttc aacaccttgt tggtctacaa cgcctccgac  180
agagtttctg ttgatccagc caaggttatc agacaggcct tgtccaaggt tctgttttac  240
tactctccat tcgccggtag actgagaaag aaagaaaacg gtgacttgga ggttgagtgt  300
actggtgaag gtgctttgtt cgttgaagct atggctgaca ctgacctgtc tgttttcggt  360
gatttggacg actactcccc atctttggag cagttgttgt tctgttttgcc accagacact  420
gacatcgagg acattcaccc attggttgtt caggtcacca gattcacttg tggtggtttc  480
gttgttggtg tctccttctg tcacggtatc tgtgatggtt tgggtgctgg tcagttcttg  540
attgctgttg gtgaaatggc cagaggtgag attaagccat cttccgagcc aatctggaag  600
agagagttgt tgaagccaga ggacccactg tacagattgc agtactacca cttccagttg  660
atctgtccac catccacctt cggtaagatc gttcaaggtt ccttggttat cacctccgag  720
actatcaact gcatcaagca gtgcttgaga gaagagtcca agagttctg ttccgccttc  780
gaagttgttt ccgctttggc ttggatcgct agaactagag ccttgcagat tccacacaac  840
gagaacgtca agctgatctt cgctatggac atgaaaagc tgttcaaccc accactgtcc  900
aagggttact acggtaactt cgttggtact gtttgcgcca tggacaacgt caaggattg  960
ttgtctggtt ccttgctgag agtcgtcaga atcatcaaga aggccaaggt tccctgaac  1020
gagcacttca cttccactat cgttactcca agatctggtt ccgacgagtc catcaactac  1080
gagaacatcg ttggtttcgg tgacagacgt agattgggtt tcgacgaagt tgatttcggt  1140
tggggtcacg ctgacaacgt ttctttggtt caacacggtc tgaaggacgt ttcagttgtt  1200
cagtcctacc tgctgttcat cagaccacca aagaacaacc cagacggtat caagatctg  1260
tcctttatgc caccaccaat cgtcaagtcc ttcaagttcg agatggaaac catgaccaac  1320
aagtacgtca ccaagcctta a                                             1341

SEQ ID NO: 46           moltype = AA  length = 446
FEATURE                 Location/Qualifiers
REGION                  1..446
                        note = DBATAca_AA
source                  1..446
                        mol_type = protein
                        organism = Fragaria X ananassa
SEQUENCE: 46
MHHHHHHAGS TEFVVRSLER VMVAPSQPSP KAFLQLSTLD NLPGVRENIF NTLLVYNASD   60
RVSVDPAKVI RQALSKVLVY YSPFAGRLRK KENGDLEVEC TGEGALFVEA MADTDLSVFG  120
DLDDYSPSLE QLLFCLPPDT DIEDIHPLVV QVTRFTCGGF VVGVSFCHGI CDGLGAGQFL  180
IAVGEMARGE IKPSSEPIWK RELLKPEDPL YRLQYYHFQL ICPPSTFGKI VQGSLVITSE  240
TINCIKQCLR EESKEFCSAF EVVSALAWIA RTRALQIPHN ENVKLIFAMD MRKLFNPPLS  300
KGYYGNFVGT VCAMDNVKDL LSGSLLRVVR IIKKAKVSLN EHFTSTIVTP RSGSDESINY  360
ENIVGFGDRR RLGFDEVDFG WGHADNVSLV QHGLKDVSVV QSYLLFIRPP KNNPDGIKIL  420
SFMPPPIVKS FKFEMETMTN KYVTKP                                        446

SEQ ID NO: 47           moltype = DNA  length = 1377
FEATURE                 Location/Qualifiers
misc_feature            1..1377
                        note = TSga
source                  1..1377
                        mol_type = genomic DNA
                        organism = Streptomyces gancidicus
SEQUENCE: 47
atgcatcatc accaccacca caagtctggt tctgctgctg gtgatgctgg tagaaccgtt   60
ttggttagat ctggtgaagc ttccggtgag agagttagat gtccgtttta cgacctggtc  120
aacggtactt tcggttcctc cagaaccttc tactacagac agagattgga caccgaggct  180
ttgagagagt ccttgagaag aactttggtc cactacccct tgctgaccgg tagattggtt  240
agagatgctg acagaggttt gtccgttgtt tgtgatgatg ctggtgctgt tttcgctgaa  300
actgactctg atagaccaat gccagattac ggtccagacc acagagttgg tgatgacttg  360
agaaggtaca tccaccagt taacgccttc agagttgttg gtcatgacac ccctttgttg  420
accgttaagg ttacccatat gagaggtggt ggttccgttt gggtgtttc cactaaccac  480
tctgttgttg acggttccgg ttgcttggat ttccttgttgc actggtccaa aacccacaga  540
ggtttggatc atagagcccc atctcacgac agagctttgt tggatggttt ggctgctggt  600
gttccaccag ctccagatga ttctcagtac gctgttatca ctggtagagc caagttcggt  660
ttcatctggc gtgttaacgc tagagccaga agagttagaa cctttaccgt cagattctcc  720
tcagccgagg ttttggcatt gagagaaact gctagagctg tggtgatca cgttagagct  780
acttccggtg atgctttgtc tgcccacatt ggagagtttg ggtgccgt tagagacaga  840
gaaccagctg ctactgaaag attgggtatc gtcgttggtt tgaaggtcc attgctgaa  900
catctgccac atggttacgg tggtaacgct gtttccaaca tcactgctgc tttgccagct  960
agacccttga gaagaaccc attggctcat actgcttccg ctgttagaga gccttggac 1020
agagttactc cagagagaat cagaagaag gctgctttct tggaggctca aagagggct 1080
ggtagagtca acagagtctt gtccagaatg gctttggact cttcgctga cactgtttcc 1140
ttgaacaacg tttccagatt gcccgtctac gctattgagt ttggtgctgg tagaccattc 1200

```
tggttcgaac atccagctac tccagttcca tggaccgttt tgattactcc aactccagat   1260
gacgaccact ccagagatgt tcacttgtct gttccaagag aagctgctga ggcattgaga   1320
actccagaat ggtccagaag attgcacctg agagaatctt ccccagacag attttaa     1377

SEQ ID NO: 48           moltype = AA   length = 458
FEATURE                 Location/Qualifiers
REGION                  1..458
                        note = Tsga_AA
source                  1..458
                        mol_type = protein
                        organism = Streptomyces gancidicus
SEQUENCE: 48
MHHHHHHKSG SAAGDAGRTV LVRSGEASGE RVRLSVYDLV NGTFGSSRTF YYRQRLDTEA    60
LRESLRRTLV HYPLLTGRLV RDADRGLSVV CDDAGAVFAE TDSDRPMPDY GPDHRVGDDL   120
RRYIHPVNAF RVVGHDTPLL TVKVTHMRGG GSVLGVSTNH SVVDGSGCLD FLLHWSRTHR   180
GLDHRAPSHD RALLDGLAAG VPPAPDDSQY AVITGRAKFG FIWRVNARAR RVRTFTVRFS   240
SAEVLALRET ARAGGDHVRA TSGDALSAHI WRVLGAVRDR EPAATERLGI VVGLRGPLSE   300
HLPHGYGGNA VSNITAALPA RALREEPLAH TASAVREALD RVTPERIREE AAFLEAQRRA   360
GRVNRVLSRM ALDSFADTVS LNNVSRLPVY AIEFGAGRPF WFEHPATPVP WTVLITPTPD   420
DDHSRDVHLS VPREAAEALR TPEWSRRLHL RESSPDRF                            458

SEQ ID NO: 49           moltype = DNA   length = 1428
FEATURE                 Location/Qualifiers
misc_feature            1..1428
                        note = TSvi
source                  1..1428
                        mol_type = genomic DNA
                        organism = Streptomyces violaceusniger
SEQUENCE: 49
atgcatcatc accatcacca cactgcttcc gctactgaat ctggtgctaa gagaaccttc     60
actgttagag ctggtgaagc ttccggtgac agattgagat tgtccgtcta cgacatgctg   120
atcggtccaa tctacactcc aagagctttc ttctaccgtg aaaccttgga cggtgaagct   180
ttgagagctt ccttgaccag aaccctgaga aacttcccaa tcctgtccgg tagaatgaag   240
agggattctg acggtggttt gtccgttttg tgtgatgacg gtggtgttag attcgttgag   300
gcttacgctt ctgagccaat gccagattac ggtccaagac acactgctaa gaagggtttg   360
gaaagacact tgtcccacgc tatgccattc tgggttgttg atcatgacac cccactgttc   420
accgttaagt tgactcatat gaagggtggt ggttccatct tgggtttgac tatgaaccac   480
gctgttgctg acggttcttc ctacatgtct ttccttggagt cctgggtcaa cgagcataga   540
ggtttgggtt acgctaagcc atctcacgac agaggtgtta tcgatacttt gggtgcttg   600
gctactggtg acactagaac tggtggtgct cacttgactg ttactggtag aggtcaaaag   660
gctgccttca tcggtagaac tgttatgggt tccttgggta acgttactac cgtcactact   720
agattcactg ctactgagtt ggccaccatg aaggatactg ctatgctga tttggccggt   780
actgaaagat gggtttccac taacgatgct ttgactgccc acttgtggaa ggttttgggt   840
gagttgagag atagaccaga cgcttccgaa gagagattgg gtttgattgc tgacttcaga   900
tcttccgctg gtgaggctgt tccagatgat tactggggta acgctgttac caacaccaga   960
ccaggtatga ctgctgctga attgagatcc agaccattgg gtgaagttgc tgctgctgtt  1020
agagcggtc atgctatgaa caccgaagag agaatcagaa aggagactgc cttcttgtgt  1080
gctgagagag atgctggtag attcaagagg gttatgacca ctatggcttt ggacgctttc  1140
gacggtacta cgctattaa caactggtcc aagctgccct tctacagaat tgactttggt  1200
cagggtctc cattctggta cgacttcact tctactccaa tcccatccac cgttcacatt  1260
gctccaactc cagctgatca aaacggtgcc agagatgttc atatggcctt gccaagaact  1320
caggtcagga cattgagaga accatcttgg gcttccagat tccacagata cgctgaatcc  1380
ggtgagactt tcccattgac tttcatggac tccaaggcca agagatag                1428

SEQ ID NO: 50           moltype = AA   length = 475
FEATURE                 Location/Qualifiers
REGION                  1..475
                        note = Tsvi_AA
source                  1..475
                        mol_type = protein
                        organism = Streptomyces violaceusniger
SEQUENCE: 50
MHHHHHHTAS ATESGAKRTF TVRAGEASGD RLRLSVYDML IGPIYTPRAF FYRETLDGEA    60
LRASLTRTLR NFPILSGRMK RDSDGGLSVL CDDGGVRFVE AYASEPMPDY GPRHTAKKGL   120
ERHLSHAMPF WVVDHDTPLF TVKLTHMKGG GSILGLTMNH AVADGSSYMS FLESWVNEHR   180
GLGYAKPSHD RGVIDTLGAL ATGDTRTGGA HLTVTGRGQK AAFIGRTVMG SLGNVTTVTT   240
RFTATELATM KDTAMADLAG TERWVSTNDA LTAHLWKVLG ELRDRPDASE ERLGLIADFR   300
SSAGEAVPDD YWGNAVTNTR PGMTAAELRS RPLGEVAAAV RAGHAMNTEE RIREETAFLC   360
AERDAGRFKR VMTTMALDAF DGTIAINNWS KLPFYRIDFG QGAPFWYDFT STPIPSTVHI   420
APTPADQNGA RDVHMALPRT QVRALREPSW ASRFHRYAES GETFPLTFMD SKAKR         475

SEQ ID NO: 51           moltype = DNA   length = 672
FEATURE                 Location/Qualifiers
misc_feature            1..672
                        note = CAT
source                  1..672
                        mol_type = genomic DNA
                        organism = Shigella sonnei
SEQUENCE: 51
```

```
atgcatcatc accatcacca cgagaaaaaa atcactggat ataccaccgt tgatatatcc   60
caatggcatc gtaaagaaca ttttgaggca tttcagtcag ttgctcaatg tacctataac  120
cagaccgttc agctggatat tacggccttt ttaaagaccg taaagaaaaa taagcacaag  180
tttatccgg cctttattca cattcttgcc cgcctgatga atgctcatcc ggaattacgt   240
atggcaatga aagacggtga gctggtgata tgggatatgt ttcacccttg ttacaccgtt  300
ttccatgagc aaactgaaac gttttcatcg ctctgaagtg aataccacga cgatttccgg  360
cagtttctac acatatattc gcaagatgtg gcgtgttacg gtgaaaacct ggcctatttc  420
cctaaagggt ttattgagaa tatgtttttc gtctcagcca atccctgggt gagtttcacc  480
agttttgatt taaacgtggc caatatggac aacttcttcg cccccgtttt caccatgggc  540
aaatattata cgcaaggcga caaggtgctg atgccgctgg cgattcaggt tcatcatgcc  600
gtttgtgatg gcttccatgt cggcagaatg cttaatgaat acaacagta ctgcgatgaa   660
ggggcggcct ga                                                      672

SEQ ID NO: 52          moltype = AA   length = 223
FEATURE                Location/Qualifiers
REGION                 1..223
                       note = CAT_AA
source                 1..223
                       mol_type = protein
                       organism = Shigella sonnei
SEQUENCE: 52
MHHHHHHEKK ITGYTTVDIS QWHRKEHFEA FQSVAQCTYN QTVQLDITAF LKTVKKNKHK   60
FYPAFIHILA RLMNAHPELR MAMKDGELVI WDSVHPCYTV FHEQTETFSS LWSEYHDDFR  120
QFLHIYSQDV ACYGENLAYF PKGFIENMFF VSANPWVSFT SFDLNVANMD NFFAPVFTMG  180
KYYTQGDKVL MPLAIQVHHA VCDGFHVGRM LNELQQYCDE GAA                    223

SEQ ID NO: 53          moltype = DNA   length = 1374
FEATURE                Location/Qualifiers
misc_feature           1..1374
                       note = EHT
source                 1..1374
                       mol_type = genomic DNA
                       organism = Saccharomyces cerevisiae
SEQUENCE: 53
atgcatcatc accatcacca ctcagaagtt tccaaatggc cagcaatcaa cccattccat   60
tggggataca atggtacagt ttcgcatatt gtcggtgaaa atggttccat taaactccat  120
ttaaaagaca acaaggagca agttgatttt gacgagttcg ctaacaaata tgtcccaacg  180
ttgaagaatg gtgcccaatt caaattgagt ccttacttgt tcacaggtat tttgcaaact  240
ttgtacttag gtgctgctga tttctctaag aaatttcctg tattctacgg cagggaaatt  300
gtcaaattct cggatggtgg agtttgcacc gctgactggc tcatagattc atggaaaaag  360
gattatgagt tcgatcaaag tactacgagc tttgataaaa aaaaatttga taagacgag   420
aaggcgacac atccagaagg atggcctcgt ttacaaccac gtacaaggta cctgaaagat  480
aatgagttgg aagaactacg ggaggttgat ctaccccctag tagttattct acatggtctt  540
gctggtggta gtcatgagcc gattataaga tctcttgctg aaaacctgtc tcgcagtggg  600
agatttcaag tggtcgtcct aaataccaga ggttgtgcac gttccaaaat taccaccaga  660
aatttatta cagcttatca cacaatggat attgcgagt ttttgcaaag agaaaagcaa    720
agcatccag atagaaaact atacgctgtg gatgctctt ttggtgctac gatgctggca    780
aactatctgg gagaagaggg cgataaatca cctttatccg cagctgctac tttgtgcaat  840
ccttgggatc ttctcctttc agcaattagg atgagccagg attggtggtc aagaacttta  900
ttttccaaaa atattgcgca attcttaaca gaaccgttc aggttaatat gggtgaatta   960
ggagttccaa atggctctct ccccgatcat cctcccacag tcaagaatcc atctttctat 1020
atgttcacgc ctgaaaatct aataaaggca aagagcttta aatcgacccg ggaatttgat 1080
gaagtgtaca ctgcgcctgc tttaggcttc ccaaatgcta tggagtatta taagcggcc  1140
agctcaataa acagagttga tacaattcgg ttcctaccc ttgttatcaa ttccagggat  1200
gatcctgttg tcggccccaga tcaaccatac tcaatcgtga aaaagaatcc tcgtatttg 1260
tattgtagaa ccgattagg tggtcatttta gcttacctag ataaagacaa caactcgtgg 1320
gctaccaagg caattagaga attttttcact aagtttgatg aattagtcgt atga       1374

SEQ ID NO: 54          moltype = AA   length = 457
FEATURE                Location/Qualifiers
REGION                 1..457
                       note = EHT_AA
source                 1..457
                       mol_type = protein
                       organism = Saccharomyces cerevisiae
SEQUENCE: 54
MHHHHHHSEV SKWPAINPFH WGYNGTVSHI VGENGSIKLH LKDNKEQVDF DEFANKYVPT   60
LKNGAQFKLS PYLFTGILQT LYLGAADFSK KFPVFYGREI VKFSDGGVCT ADWLIDSWKK  120
DYEFDQSTTS FDKKKFDKDE KATHPEGWPR LQPRTRYLKD NELEELREVD LPLVVILHGL  180
AGGSHEPIIR SLAENLSRSG RFQVVVLNTR GCARSKITTR NLFTAYHTMD IREFLQREKQ  240
RHPDRKLYAV GCSFGATMLA NYLGEEGDKS PLSAAATLCN PWDLLLSAIR MSQDWWSRTL  300
FSKNIAQFLT RTVQVNMGEL GVPNGSLPDH PPTVKNPSFY MFTPENLIKA KSFKSTREFD  360
EVYTAPALGF PNAMEYYKAA SSINRVDTIR VPTLVINSRD DPVVGPDQPY SIVEKNPRIL  420
YCRTDLGGHL AYLDKNNSW ATKAIAEFFT KFDELVV                            457

SEQ ID NO: 55          moltype = DNA   length = 1596
FEATURE                Location/Qualifiers
misc_feature           1..1596
                       note = ATF
```

| source | 1..1596 |
| --- | --- |
| | mol_type = genomic DNA |
| | organism = Saccharomyces cerevisiae |

SEQUENCE: 55

```
atgcatcatc accatcacca caatgaaatc gatgagaaaa atcaggcccc cgtgcaacaa    60
gaatgcctga aagagatgat tcagaatggg catgctcggc gtatgggatc tgttgaagat   120
ctgtatgttg ctctcaacag acaaaactta tatcgaaact tctgcacgta tggagaattg   180
agtgattact gtactaggga tcagctcaca ttagctttga gggaaatctg cctgaaaaat   240
ccaactcttt tacatattgt tctaccaaca agatggccaa atcatgaaaa ttattatcga   300
agttccgaat actattcacg gccacatcca gtgcatgatt atatttcagt attacaagaa   360
ttgaaactga gtggtgtggt tctcaatgaa caacctgagt acagtgcagt aatgaagcaa   420
atattagaag agttcaaaaa tagtaagggt tcctatactg caaaaatttt taaacttact   480
accactttga ctattcctta ctttggacca acaggaccga gttggcggct aatttgtctt   540
ccagaagagc acacagaaaa gtggaaaaaa tttatctttg tatctaatca ttgcatgtct   600
gatggtcggt cttcgatcca ctttttcat gatttaagag acgaattaaa taatattaaa   660
actccaccaa aaaaattaga ttacattttc aagtacgagg aggattacca attattgagg   720
aaacttccag aaccgatcga aaaggtgata gactttagac caccgtactt gtttattccg   780
aagtcacttc tttcgggttt catctacaat catttgagat tttcttcaaa aggtgtctgt   840
atgagaatgg atgatgtgga aaaaaccgat gatgttgtca ccgagatcat caatatttca   900
ccaacagaat ttcaagcgat taaagcaaat attaaatcaa atatccaagg taagtgtact   960
atcactccgt ttttacatgt ttgttggttt gtatctcttc ataaatgggg taaatttttc  1020
aaaccattga acttcgaatg gcttacggat attttttacc ccgcagattg ccgctcacaa  1080
ctaccagatg atgatgaaat gagacagatg tacagatatg gcgctaacgt tggatttatt  1140
gacttcaccc cctggataag cgaatttgac atgaatgata caaagaaaa ttttttggcca  1200
cttattgagc actaccatga agtaatttcg gaagctttaa gaaataaaaa gcatctccat  1260
ggcttagggt tcaatataca aggctcgtt caaaaatatg taacattga caaggtaatg  1320
tgcgatcgtg ccatcgggaa aagacgcgga ggtacattgt taagcaatgt aggtctgttt  1380
aatcagttag aggagcccga tgccaaatat tctatatgcg atttggcatt tggccaattt  1440
caaggatcct ggcaccaagc atttttcctt ggtgtttgtt cgactaatgt aaaggggatg  1500
aatattgttg ttgcttcaac aaaagaatgt tgttggtagtc aagaatctct cgaagagctt  1560
tgctccattt acaaagctct cctttttaggc ccttag                            1596
```

| SEQ ID NO: 56 | moltype = AA  length = 531 |
| --- | --- |
| FEATURE | Location/Qualifiers |
| REGION | 1..531 |
| | note = ATF_AA |
| source | 1..531 |
| | mol_type = protein |
| | organism = Saccharomyces cerevisiae |

SEQUENCE: 56

```
MHHHHHHNEI DEKNQAPVQQ ECLKEMIQNG HARRMGSVED LYVALNRQNL YRNFCTYGEL    60
SDYCTRDQLT LALREICLKN PTLLHIVLPT RWPNHENYYR SSEYYSRPHP VHDYISVLQE   120
LKLSGVVLNE QPEYSAVMKQ ILEEFKNSKG SYTAKIFKLT TTLTIPYFGP TGPSWRLICL   180
PEEHTEKWKK FIFVSNHCMS DGRSSIHFFH DLRDELNNIK TPPKKLDYIF KYEEDYQLLR   240
KLPEPIEKVI DFRPPYLFIP KSLLSGFIYN HLRFSSKGVC MRMDDVEKTD DVVTEIINIS   300
PTEFQAIKAN IKSNIQGKCT ITPFLHVCWF VSLHKWGKFF KPLNFEWLTD IFIPADCRSQ   360
LPDDDEMRQM YRYGANVGFI DFTPWISEFD MNDNKEMFQN LIEHYHEVIS EALRNKKHLH   420
GLGFNIQGFV QKYVNIDKVM CDRAIGKRRG GTLLSNVGLF NQLEEPDAKY SICDLAFGQF   480
QGSWHQAFSL GVCSTNVKGM NIVVASTKNV VGSQESLEEL CSIYKALLLG P            531
```

| SEQ ID NO: 57 | moltype = DNA  length = 1344 |
| --- | --- |
| FEATURE | Location/Qualifiers |
| misc_feature | 1..1344 |
| | note = Aco_op |
| source | 1..1344 |
| | mol_type = genomic DNA |
| | organism = Arabidopsis thaliana |

SEQUENCE: 57

```
atgcatcacc atcaccatca cactagtgga tccatggcag tcctatcctc agctgatagg    60
gctagtaacg aaaagaaggt aaagtcatct tacttcgact tgcctccaat ggaaatgtca   120
gttgcattcc cacaagccac accagcttct acgtttcccc cgtgcacttc tgattactat   180
cactttaatg acttgttgac accagaagag caggcaatta gaaagaaggt aagagagtgt   240
atggaaaaag aagttgctcc gattatgact gaatactggg agaaggcaga gtttccattt   300
catataacac ctaagctagg ggctatggga gttgcaggcg gatctatcaa aggttacggt   360
tgtccaggcc taagcatcac agccaatgct atcgcaacag ccgaaattgc aagggttgat   420
gccagtgtt ctacgttcat tttagtccat agttctttag gaatgctgac aattgcttta   480
tgcggtagtg aagcacaaaa agagaaatac cttccatcct ggcacaact taatacagtg   540
gcctgctggg cgcttactga gccagataat ggttctgatg cttcaggatt gggaaccaca   600
gcgactaagg tggaaggcgg ttggaaggatt aacggtcaaa aaaggtgaat aggaaactca   660
acattcgcgg atttattgat tatctttgct agaaacacga ctaccaacca atcaacggc    720
ttcattgtaa agaagatgc tcctggctta aagcaaccaa aatccctaa taaaattggt   780
ttgaggatgt acaaaacgg ggatatcttg ttacagaacg tgtttgtgcc cgacgaagat   840
cgtctacccg gtgttaattc ttttccaagac acttccaagg tattagcagt ctcacgtgtt   900
atggtagtcg ggcagctgat tgtgtatctct atgggtgatac acgatatgtg tcatagatac   960
ctgaaagaaa ggaagcagtt tggagctcct ttagctgctt tcaacttaa ccagcaaaaa  1020
ttggtacaaa tgttaggaaa tgttcaagcg atgttcctta tgggctggag attgtgtaag  1080
ttatacgaaa ctggtcaaat gacacctggt cagggccgtcat taggtaaggc ttggatatcc  1140
tctaaggcaa gagaaacagc aagtttggc agagaacttt aggtggaaa cggtatttta  1200
gccgatttcc tagttgcgaa agcattctgt gacttggagc ctatatacac atacgaaggg  1260
```

```
acttacgata ttaatacatt agtgacgggg agagaagtta caggcattgc tagtttcaaa   1320
ccagctacaa ggtctagatt ataa                                          1344

SEQ ID NO: 58           moltype = AA  length = 447
FEATURE                 Location/Qualifiers
REGION                  1..447
                        note = Aco_AA
source                  1..447
                        mol_type = protein
                        organism = Arabidopsis thaliana
SEQUENCE: 58
MHHHHHHTSG SMAVLSSADR ASNEKKVKSS YFDLPPMEMS VAFPQATPAS TFPPCTSDYY    60
HFNDLLTPEE QAIRKKVREC MEKEVAPIMT EYWEKAEFPF HITPKLGAMG VAGGSIKGYG   120
CPGLSITANA IATAEIARVD ASCSTFILVH SSLGMLTIAL CGSEAQKEKY LPSLAQLNTV   180
ACWALTEPDN GSDASGLGTT ATKVEGGWKI NGQKRWIGNS TFADLLIIFA RNTTTNQING   240
FIVKKDAPGL KATKIPNKIG LRMVQNGDIL LQNVFVPDED RLPGVNSFQD TSKVLAVSRV   300
MVAWQPIGIS MGIYDMCHRY LKERKQFGAP LAAFQLNQQK LVQMLGNVQA MFLMGWRLCK   360
LYETGQMTPG QASLGKAWIS SKARETASLG RELLGGNGIL ADFLVAKAFC DLEPIYTYEG   420
TYDINTLVTG REVTGIASFK PATRSRL                                      447

SEQ ID NO: 59           moltype = DNA  length = 1554
FEATURE                 Location/Qualifiers
misc_feature            1..1554
                        note = Pct_Me
source                  1..1554
                        mol_type = genomic DNA
                        organism = Fragaria X ananassa
SEQUENCE: 59
atgagaaagg ttgaaattat taccgctgaa caagctgctc aattggttaa ggacaacgac    60
accattacct ctattggttt cgtttcttct gctcacccag aagctttgac caaggctttg   120
gaaaagagat tcttggacac caacacccca caaaacttga cctacattta cgctggttct   180
caaggtaaga gagacggtag agctgctgaa cacttggctc acaccggttt gttgaagaga   240
gctattattg gtcactggca aaccgttcca gctattggta agttggctgt tgaaaacaag   300
attgaagctt acaacttctc tcaaggtacc ttggttcact tggaaccgt ggttcagagc tttggctggt   360
cacaagttgg gtgttttcac cgacattggt ttggaaacct tcttggaccc aagacaattg   420
ggtggtaagt tgaacgacgt taccaaggaa gacttggtta gttgattga agttgacggt   480
cacgaacaat tgttctaccc aaccttccca gttaacgttg ctttcttgag aggtacctac   540
gctgacgaat ctggtaacat tactatggac gaagaaattg gtccattcga atctacctct   600
gttgctcaag ctgttcacaa ctgtgtggt aaggttgtta ttcaagttaa ggacgttgt   660
gctcacggtt cttgaccc aagaatggtt aagattccag gtatttacgt tgactacgtt   720
gttgttgctc ctccagaaga ccaccaacaa acctacgact gtgaatacga cccatctttg   780
tctggtaaca cagagctcc agaaggtgct accgacgctg ctttgccaat gtctgctaag   840
aagattattg gtagaagagg tgctttggaa ttgaccgaaa acgctgttgt taacttggtg   900
gttggtgctc cagaatacgt tgcttctgtt gctggtgaag aaggtattgc tgacaccatt   960
accttgaccg ttgaaggtgg tgctattggt ggtgttccac aaggtggtgc tagattcggt  1020
tcttcaagaa acgctgacgc tattattgac cacacctacc aattcgactt ctacgacggt  1080
ggtggtttgg acattgctta cttgggtttg gctcaatgtg acggttctgg taacattaac  1140
gtttctaagt tcggtaccaa cgttgctggt tgtggtggtt tcccaaacat ttctcaacaa  1200
accccaaacg tttacttctg tggtaccttc accgctggtg gtttgaagat tgctgttgaa  1260
gacggtaagg ttaagatttt gcaagaaggt aaggctaaga agttcattaa ggctgttgac  1320
caaattacct tcaacggttc ttacgctgct agaaacggta agcacgtttt gtacattacc  1380
gaaagatgtg ttttcgaatt gaccaaggaa ggtttgaagt tgattgaagt tgctccaggt  1440
attgacattg aaaaggacat tttggctcac atggacttca gccaattat tgacaaccca  1500
aagttgatga cgctagatt gttccaagac ggtccaatgg gtttgaagaa gtaa         1554

SEQ ID NO: 60           moltype = AA  length = 517
FEATURE                 Location/Qualifiers
REGION                  1..517
                        note = Pct_Me_AA
source                  1..517
                        mol_type = protein
                        organism = Fragaria X ananassa
SEQUENCE: 60
MRKVEIITAE QAAQLVKDND TITSIGFVSS AHPEALTKAL EKRFLDTNTP QNLTYIYAGS    60
QGKRDGRAAE HLAHTGLLKR AIIGHWQTVP AIGKLAVENK IEAYNFSQGT LVHWFRALAG   120
HKLGVFTDIG LETFLDPRQL GGKLNDVTKE DLVKLIEVDG HEQLFYPTFP VNAFLRGTY   180
ADESGNITMD EEIGPFESTS VAQAVHNCGG KVVVQVKDVV AHGSLDPRMV KIPGIYVDYV   240
VVAAPEDHQQ TYDCEYDPSL SGEHRAPEGA TDAALPMSAK KIIGRRGALE LTENAVVNLG   300
VGAPEYVASV AGEEGIADTI TLTVEGGAIG GVPQGGARFG SSRNADAIID HTYQFDFYDG   360
GGLDIAYLGL AQCDGSGNIN VSKFGTNVAG CGGFPNISQQ TPNVYFCGTF TAGGLKIAVE   420
DGKVKILQEG KAKKFIKAVD QITFNGSYAA RNGKHVLYIT ERCVFELTKE GLKLIEVAPG   480
IDIEKDILAH MDFKPIIDNP KLMDARLFQD GPMGLKK                            517

SEQ ID NO: 61           moltype = DNA  length = 1629
FEATURE                 Location/Qualifiers
misc_feature            1..1629
                        note = Pct_Cn
source                  1..1629
                        mol_type = genomic DNA
```

```
                        organism = Cupriavidus necator
SEQUENCE: 61
atgaaggtta ttaccgcaag agaagctgct gcattggttc aagacggttg gaccgttgct    60
tctgctggtt tcgttggtgc tggtcacgct gaagctgtta ccgaagcatt ggaacaaaga   120
ttcttgcaat ctggattgcc aagagacttg accttgctgt actctgctgg acaaggtgac   180
agaggtgcta gaggtgttaa tcacttcggt aacgctggta tgaccgcttc tattgttggt   240
ggtcactgga gatctgctac cagattggct accttggcta tggctgaaca atgtgaaggt   300
tacaacttgc cacaaggtgt tttgacccac ctatacagag ctattgctgg tggtaagcca   360
ggtgttatga ccaagattgg tttgcacacc ttcgttgacc caagaaccgc tcaagacgct   420
agataccacg gtggtgctgt taatgaaaga gctagacaag ctatagctga aggtaaggct   480
tgttgggttg acgctgttga cttcagaggt gacgaatact tgttctaccc atcttttccca  540
attcactgtg ctttgattag atgtaccgct gctgacgcta gaggtaactt gtctacccac   600
agaagcat tccaccacga attgttggct atggctaag ctgctcacaa ctctggtggt       660
attgttattg ctcaagttga aatttttggt gaccaccaca aaattttgca agctattcac   720
gttccaggta ttttggttga ctacgttgtt gtttgtgaca acccagctaa ccaccaaatg   780
accttcgctg aatcttacaa cccagcttac gttaccccct tggcaaggtga agctgctgtt   840
gctgaagctg aagctgctcc agttgcagct ggtccattgg acgctagaac cattgttcaa   900
aggagacctg ttatggaatt ggctagaagg gctccaagtg ttgttaattt gggtgttggt   960
atgccagctg ctgttggtat gttggctcac caagcaggat tggacggttt cacccttgacc 1020
gttgaagctg gtccaattgg tggtaccccca gctgacggtt tgtctttcgg agcttctgct  1080
tacccagaag ctgttgttga ccaaccagct caattcgact tctacgaagg tggtggtatt  1140
gacttggcta tttttgggttt ggctgaattg gacggtcacg gtaacgttaa tgtttctaag  1200
ttcggtgaag gtgaaggtgc ttctatagct ggtgttggtg gtttcattaa cattacccaa  1260
tctgctagag ctgttgtttt catgggtacc ttgaccgctg gtggattgga agttagagct  1320
ggtgacggtg gtttgcaaat tgttagagaa ggtagagtta agaagattgt tcctgaagtt  1380
tctcacttgt ctttcaacgg accatacgtt gcttctttg gtattccagt tttgtacatt    1440
accgaaagag ctgttttcga aatgagagca ggtgctgacg gtgaagctag attgaccttg   1500
gttgaaattg ctccaggtgt tgacttgcaa agagacgttt tggaccaatg ttctaccccca  1560
attgctgtag ctcaagactt gagagaaatg gacgctagat tgttccaagc tggaccattg   1620
cacttgtaa                                                           1629

SEQ ID NO: 62          moltype = AA   length = 542
FEATURE                Location/Qualifiers
REGION                 1..542
                       note = Pct_CN_AA
source                 1..542
                       mol_type = protein
                       organism = Cupriavidus necator
SEQUENCE: 62
MKVITAREAA ALVQDGWTVA SAGFVGAGHA EAVTEALEQR FLQSGLPRDL TLVYSAGQGD     60
RGARGVNHFG NAGMTASIVG GHWRSATRLA TLAMAEQCEG YNLPQGVLTH LYRAIAGGKP   120
GVMTKIGLHT FVDPRTAQDA RYHGGAVNER ARQAIAEGKA CWVDAVDFRG DEYLFYPSFP   180
IHCALIRCTA ADARGNLSTH REAFHHELLA MAQAAHNSGG IVIAQVESLV DHHEILQAIH   240
VPGILVDYVV VCDNPANHQM TFAESYNPAY VTPWQGEAAV AEAEAAPVAA GPLDARTIVQ   300
RRAVMELARR APRVVNLGVG MPAAVGMLAH QAGLDGFTLT VEAGPIGGTP ADGLSFGASA   360
YPEAVVDQPA QFDFYEGGGI DLAILGLAEL DGHGNVNVSK FGEGEGASIA GVGGFINITQ   420
SARAVFMGT LTAGGLEVRA GDGGLQIVRE GRVKKIVPEV SHLSFNGPYV ASLGIPVLYI    480
TERAVFEMRA GADGEARLTL VEIAPGVDLQ RDVLDQCSTP IAVAQDLREM DARLFQAGPL   540
HL                                                                  542

SEQ ID NO: 63          moltype = DNA   length = 6360
FEATURE                Location/Qualifiers
misc_feature           1..6360
                       note = pYP004
source                 1..6360
                       mol_type = other DNA
                       organism = synthetic construct
SEQUENCE: 63
gagctcgtag gaacaatttc ggggcccctgc gtgttcttct gaggttcatc ttttacattt    60
gcttctgctg gataatttc agaggcaaca aggaaaaatt agatggcaaa agtcgtctt    120
tcaaggaaaa atcccccacca tcttttcgaga tcccctgtaa cttattggca actgaaagaa   180
tgaaaaggag gaaaatacaa aatatactag aactgaaaaa aaaaaagtat aaatagagac   240
gatatatgcc aatacttcac aatgttcgaa tctattcttc atttgcagct attgtaaaat   300
aataaaacat caagaacaaa caagctcaac ttgtcttttc taagaacaaa gaataaacaa   360
aaaaacaaaa agtttttta attttaatca aaaagttaac atgcatcacc atcaccatca    420
cactagtgga tcccccgggc tgcaggaatt cgatatcaag cttatcgata ccgtcgacct    480
cgagtcatgt aattagttat gtcacgctta cattcacgcc ctccccccac atccgctcta   540
accgaaaagg aaggagttag acaacctgaa gtctaggtcc ctatttattt ttttatgtt    600
atgttagtat taagaacgtt atttatattt caaatttttc ttttttttct gtacagacgc    660
gtgtacgcat gtaacattat actgaaaacc ttgcttgaga aggttttggg acgctcgaag   720
gctttaattt gcgccggta cccaattcgc cctatagtga gtcgtattac gcgcgctcac    780
tggccgtcgt tttacaacgt cgtgactggg aaaaccctgg cgttacccaa cttaatcgcc   840
ttgcagcaca tccccctttc gccagctggc gtaatagcga agaggcccgc accgatcgcc   900
cttcccaaca gttgcgcagc ctgaatggcg aatggcgcct gatgcggtat ttctccttcag  960
gacgactgtg cctcttccag gtcacgaccc tcgcgacctc acttagcgcga attaacgccg 1020
```

```
caacactcaa ccctatctcg gtctattctt ttgatttata agggattttg ccgatttcgg  1320
cctattggtt aaaaaatgag ctgatttaac aaaaatttaa cgcgaatttt aacaaaatat  1380
taacgtttac aatttcctga tgcggtattt tctccttacg catctgtgcg gtatttcaca  1440
ccgcataggg taataactga tataattaaa ttgaagctct aatttgtgag tttagtatac  1500
atgcatttac ttataataca gttttttagt tttgctggcc gcatcttctc aaatatgctt  1560
cccagcctgc ttttctgtaa cgttcaccct ctaccttagc atcccttccc tttgcaaata  1620
gtcctcttcc aacaataata atgtcagatc ctgtagagac cacatcatcc acggttctat  1680
actgttgacc caatgcgtct cccttgtcat ctaaacccac accgggtgtc ataatcaacc  1740
aatcgtaacc ttcatctctt ccacccatgt ctctttgagc aataaagccg ataacaaaat  1800
ctttgtcgct cttcgcaatg tcaacagtac ccttagtata ttctccagta gatagggagc  1860
ccttgcatga caattctgct aacatcaaaa ggcctctagg ttcctttgtt acttcttctg  1920
ccgcctgctt caaaccgcta acaatacctg ggcccaccac accgtgtgca ttcgtaatgt  1980
ctgcccattc tgctattctg tatacacccg cagagtactg caatttgact gtattaccaa  2040
tgtcagcaaa tttttctgtct tcgaagagta aaaaattgta cttggcggat aatgcctta  2100
gcggcttaac tgtgccctcc atggaaaaat cagtcaagat atccacatgt gttttttagta 2160
aacaaatttt gggacctaat gcttcaacta actccagtaa ttccttggtg gtacgaacat  2220
ccaatgaagc acacaagttt gtttgctttt cgtgcatgat attaaatagc ttggcagcaa  2280
caggactagg atgagtagca gcacgttcct tatatgtagc tttcgacatg atttatcttc  2340
gtttcctgca ggttttttgtt ctgtgcagtt gggttaagaa tactgggcaa tttcatgttt  2400
cttcaacact acatatgcgt atatataccaa atctaagtct gtgctccttc cttcgttctt  2460
ccttctgttc ggagattacc gaatcaaaaa aatttcaaag aaaccgaaat caaaaaaaag  2520
aataaaaaaa aaatgatgaa ttgaattgaa aagctgtggt atggtgcact ctcagtacaa  2580
tctgctctga tgccgcatag ttaagccagc cccgacaccc gccaacaccc gctgacgcgc  2640
cctgacgggc ttgtctgctc ccggcatccg cttacagaca agctgtgacc gtctccggga  2700
gctgcatgtg tcagaggttt tcaccgtcat caccgaaacg cgcgagacga aagggcctcg  2760
tgatacgcct atttttatag gttaatgtca tgataataat ggtttcttag tatgatccga  2820
tatcaaagga aatgatagca ttgaaggatg agactaatcc aattgaggag tggcagcata  2880
tagaacagct aaagggtagt gctgaaggaa gcatacgata ccccgcatgg aatgggataa  2940
tatcacagga ggtactagac tacctttcat cctacataaa tagacgcata taagtacgca  3000
tttaagcata aacacgcact cctcgcttct tctcatgtat atatatatac aggcaacacg  3060
cagatatagg tgcgacgtga acagtgagct gtatgtgcgc agctcgcgtt gcattttcgg  3120
aagcgctcgt tttcggaaac gctttgaagt tcctattccg aagttcctat tctctagaaa  3180
gtataggaac ttcagagcgc ttttgaaaac caaaagcgct ctgaagacgc actttcaaaa  3240
aaccaaaaac gcaccggact gtaacgagct actaaaatat tgcgaatacc gcttccacaa  3300
acattgctca aaagtatctc tttgctatat atctctgtgc tatatcccta tataacctac  3360
ccatccacct ttcgctcctt gaacttgcat ctaaactcga cctctacatt ttttatgttt  3420
atctctagta ttactctta gacaaaaaaa ttgtagtaag aactattcat agagtgaatc  3480
gaaacaata cgaaaatgta aacatttcct atacgtagta tatagagaca aaatagaaga  3540
aaccgttcat aattttctga ccaatgaaga atcatcaacg ctatcacttt ctgttcacaa  3600
agtatgcgca atccacatcg gtatagaata taatcgggga tgcctttatc ttgaaaaaat  3660
gcacccgcag cttcgctagt aatcagtaaa cgcgggaagt ggagtcaggc tttttttatg  3720
gaagagaaaa tagacaccaa agtagccttc ttctaacctt aacggaccta cagtgcaaaa  3780
agttatcaag agactgcatt atagagcgca caaaggagaa aaaaagtaat ctaagatgct  3840
ttgttagaaa aatagcgctc tcgggatgca tttttgtaga acaaaaaaga agtatagatt  3900
ctttgttggt aaaatagcgc tctcgcgttg catttctgtt ctgtaaaaat gcagctcaga  3960
ttctttgttt gaaaaattag cgctctcgcg ttgcattttt gttttacaaa aatgaagcac  4020
agattcttcg ttggtaaaat agcgctttgc cgttgcattt ctgttctgta aaaatgcagc  4080
tcagattctt tgtttgaaaa attagcgctc tcgcgttgca tttttgttct acaaaatgaa  4140
gcacagatgc ttcgttcagg tggcactttt cggggaaatg tgcgcggaac ccctatttgt  4200
ttatttttct aaatacattc aaatatgtat ccgctcatga caataaacc ctgataaatg  4260
cttcaataat attgaaaaag gaagagtatg agtattcaac atttccgtgt cgcccttatt  4320
ccctttttg cggcatttttg ccttcctgtt tttgctcacc cagaaacgct ggtgaaagta  4380
aaagatgctg aagatcagtt gggtgcacga gtgggttaca tcgaactgga tctcaacagc  4440
ggtaagatcc ttgagagttt tcgccccgaa gaacgttttc caatgatgag cacttttaaa  4500
gttctgctat gtggcgcggt attatcccgt attgacgccg ggcaagagca actcggtcgc  4560
cgcatacact attctcagaa tgacttggtt gagtactcac cagtcacaga aaagcatctt  4620
acggatggca tgacagtaag agaattatgc agtgctgcca taaccatgag tgataacact  4680
gcggccaact tacttctgac aacgatcgga ggaccgaagg agctaaccgc ttttttgcac  4740
aacatggggg atcatgtaac tcgccttgat cgttgggaac cggagctgaa tgaagccata  4800
ccaaacgacg agcgtgacac cacgatgcct gtagcaatgg caacaacgtt gcgcaaacta  4860
ttaactggcg aactacttac tctagcttcc cggcaacaat taatagactg gatggaggcg  4920
gataaagttg caggaccact tctgcgctcg gcccttccgg ctggctggtt tattgctgat  4980
aaatctggag ccggtgagcg tgggtctcgc ggtatcattg cagcactggg gccagatggt  5040
aagccctccc gtatcgtagt tatctacacg acggggagtc aggcaactat ggatgaacga  5100
aatagacaga tcgctgagat aggtgcctca ctgattaagc attggtaact gtcagaccaa  5160
gtttactcat atatacttta gattgattta aacttcatt tttaatttaa aaggatctag  5220
gtgaagatcc ttttttgataa tctcatgacc aaaatccctt aacgtgagtt ttcgttccac  5280
tgagcgtcag accccgtaga aaagatcaaa ggatcttctt gagatcctt ttttctgcgc  5340
gtaatctgct gcttgcaaac aaaaaaacca ccgctaccag cggtggtttg tttgccggat  5400
caagagctac caactctttt tccgaaggta actggcttca gcagagcgca gataccaaat  5460
actgtccttc tagtgtagcc gtagttaggc caccacttca agaactctgt agcaccgcct  5520
acatacctcg ctctgctaat cctgttacca gtggctgctg ccagtggcga taagtcgtgt  5580
cttaccgggt tggactcaag acgatagtta ccggataagg cgcagcggtc gggctgaacg  5640
gggggttcgt gcacacagcc cagcttggag cgaacgacct acaccgaact gagatacctac 5700
cagcgtgagc tatgagaaag cgccacgctt cccgaaggga gaaaggcgga caggtatccg  5760
gtaagcggca gggtcggaac aggagagcgc acgagggagc ttccaggggg aaacgcctgg  5820
tatctttata gtcctgtcgg gtttcgccac ctctgacttg agcgtcgatt tttgtgatgc  5880
tcgtcagggg gcggagcct atggaaaaac gccagcaacg cggccttttt acggttcctg  5940
gccttttgct ggccttttgc tcacatgttc tttcctgcgt tatcccctga ttctgtggat  6000
```

```
aaccgtatta ccgcctttga gtgagctgat accgctcgcc gcagccgaac gaccgagcgc 6060
agcgagtcag tgagcgagga agcggaagag cgcccaatac gcaaaccgcc tctccccgcg 6120
cgttggccga ttcattaatg cagctggcac gacaggtttc ccgactgaa  agcgggcagt 6180
gagcgcaacg caattaatgt gagttacctc actcattagg caccccaggc tttacacttt 6240
atgcttccgg ctcctatgtt gtgtggaatt gtgagcggat aacaatttca cacaggaaac 6300
agctatgacc atgattacgc caagcgcgca attaaccctc actaaaggga acaaaagctg 6360
```

| SEQ ID NO: 64 | moltype = DNA  length = 6907 |
|---|---|
| FEATURE | Location/Qualifiers |
| misc_feature | 1..6907 |
| | note = pYP083 |
| source | 1..6907 |
| | mol_type = other DNA |
| | organism = synthetic construct |

SEQUENCE: 64

```
cagcgacatg gaggcccaga ataccctcct tgacagtctt gacgtgcgca gctcaggggc   60
atgatgtgac tgtcgcccgt acatttagcc catacatccc catgtataat catttgcatc  120
catacatttt gatggccgca cggcgcgaag caaaaattac ggctcctcgc tgcagacctg  180
cgagcaggga aacgctcccc tcacagacgc gttgaattga ccccacgccg cgcccctgta  240
gagaaaatat aaaaggttag gatttgccac tgaggttcttc tttcatatac ttccttttaa  300
aatcttgcta ggatacagtt ctcacatcac atccgaacat aaacaaccat gggtaaggaa  360
aagactcacg tttcgaggcc gcgattaaat tccaacatgg atgctgattt atatgggtat  420
aaatgggctc gcgataatgt cgggcaatca ggtgcgacaa tctatcgatt gtatgggaag  480
cccgatgcgc cagagttgtt tctgaaacat ggcaaaggta gcgttgccaa tgatgttaca  540
gatgagatgg tcagactaaa ctggctgacg gaatttatgc ctcttccgac catcaagcat  600
tttatccgta ctcctgatga tgcatggtta ctcaccactg cgatcccggg caaaacagca  660
ttccaggtat tagaagaata tcctgattca ggtgaaaata ttgttgatgc gctggcagtg  720
ttcctgcgcc ggttgcattc gattcctgtt tgtaattgtc cttttaacag cgatcgcgta  780
tttcgtctcg ctcaggcgca atcacgaatg aataacggtt tggttgatgc gagtgatttt  840
gatgacgagc gtaatggctg gcctgttgaa caagtctgga agaaatgca  taagctcttt  900
ccattctcac cggattcagt cgtcactcat ggtgatttct cacttgataa ccttattttt  960
gacgagggga aattaatagg ttgtattgat gttggacgag tcggaatcgc agaccgatac 1020
caggatcttg ccatcctatg gaactgcctc ggtgagtttt ctccttcatt acagaaacgg 1080
cttttttcaaa aatatggtat tgataatcct gatatgaata aattgcagtt tcatttgatg 1140
ctcgatgagt ttttctaatc agtactgaca ataaaaagat tcttgttttc aagaacttgt 1200
catttgtata gttttttttat attgtagttg ttcattttta atcaaatgtt agcgtgattt 1260
atattttttt tcgcctcgac atcatctgcc cagatgcgaa gttaagtgcg cagaaagtaa 1320
tatcatgcgt caatcgtatg tgaatgctgg tcgctatact gctgtcgatt cgatactaac 1380
gccgccatcc agtgtcgaaa acgcggtgtg aaataccgca cagatgcgta aggagaaaat 1440
accgcatgag ctcgtaggaa caatttcggg ccctgcgtg  ttcttctgag gttcatcttt 1500
tacatttgct tctgctggat aattttcaga ggcaacaagg aaaaattaga tggcaaaaag 1560
tcgtctttca aggaaaaatc cccaccatct ttcgagatcc cctgtaactt attggcaact 1620
gaaagaatga aaaggaggaa aatacaaaat atactagaac tgaaaaaaaa aaagtataaa 1680
tagagacgat atatgccaat acttcacaat gttcgaatca ttcttcatt  tgcagctatt 1740
gtaaaataat aaaacatcaa gaacaaacaa gctcaacttg tcttttctaa gaacaaagaa 1800
taaacacaaa aacaaaagt  tttttaatt  ttaatcaaaa agaattcaaa acgatgcatc 1860
accatcacca ccacgagact atgcagacta tcgacttctc attccaggtt agaaagtgtc 1920
agccagagtt gatcgctcca gctaacccaa ctccatacga gttcaagcaa ttgtccgacg 1980
ttgacgacca acagtccttg agattccagt tgccattggt taacatctac caccacaacc 2040
catccttgga gggtagagat ccagttaagg ttatcaaaga ggctatcgct aaggctttgg 2100
ttttctacta cccattggct ggtagattga gagagggtcc ttagtagaaag ttgttcgtta 2160
agtgtactgg tgagggtatc ttgttcattg aagctgacgc tgacgtttcc ttggagcagt 2220
tcagagatac tttgccatac tccttgtcct ccatggaaaa caacatcatc cacaactcat 2280
tgaactccga cggtgttttg aactcccctt tgttgttgat ccaggttact agattgaagt 2340
gtggtggttt catcttcggt atccacttcg accacactat ggctgacgt  tttggtatcg 2400
ctcagttcat gaaggctatt gctgagatcc tagaggtgc  tttcgctcca tctattttgc 2460
cagtttggca gagagctttg ttgactgcta gagatcctcc aagaatcact gttagacact 2520
acgagtacga ccaggttgtt gacactaagt ccacttgat  cccagctaac aacatgatcg 2580
acagattgtt cttcttcact cagagacaga tctccacatt gagacagact tgccagctc  2640
acttgcacga ctgttcttca ttcgaggttt tgactgctta cgtttggaga ttgagaacta 2700
tcgctttcca gttgaagcca gaggaagagg ttagattctt gtgtgttgtt aacttgagat 2760
ccaagatcga catcccattg ggtttctacg gtaacgctat cgtttcccca gctgttatca 2820
ctactgttgc taagttgtgt ggtaacccct tgggttacgc tgttgacttg atcagaaagg 2880
ctaaggctaa agctacaaaa gagtacatca agtccatggt tgacttcatg gttatcaagg 2940
gtagaccaag attcactgag atcggtccat tcatgatgtc cgacattact agaatcggtt 3000
tcgagaacgt tgacttcggt tggggtaagg ctatttccgg tggtccaatt atcggtggtt 3060
gtggtatcat cagaggtatg atctcttact ccattgcttt catgaacaga aacggtgaga 3120
agggaatcgt tgttccattg gtgttgccac caccagctat ggaaagattc agagctaacg 3180
ttcacgcttc cttgcaggtt atccaggtt  tggacaaggt tgacagagac atgcaaacaa 3240
tcttgtccgc tttgtaaagg gcggccgct  catgtaatta gttatgtcac gcttacattc 3300
acgccctccc cccacatccg ctctaaccga aaggaagga gttgacaac  ctgaagtcta 3360
ggtcccatt  tatttttta tagttatgtt agtattaaga acgttattta tatttcaaat 3420
ttttctttt  tttctgtaca gacgcgtgta cgcatgtaac attatactga aaaccttgct 3480
tgagaaggtt ttgggacgct cgaaggcttt aatttgcggt ccgtacccaa ttcgccgaac 3540
cgtaaaaagg ccgcgttgct ggcgtttttc cataggctcc gcccccctga cgagcatcac 3600
aaaaatcgac gctcaagtca gaggtggcga aacccgacag gactataaag ataccaggcg 3660
tttccccctg gaagctccct cgtgcgctct cctgttccga cctgccgct  taccggatac 3720
ctgtccgcct ttctcccttc gggaagcgtg gcgctttctc atagctcacg ctgtaggtat 3780
ctcagttcgg tgtaggtcgt tcgctccaag ctgggctgtg tgcacgaacc cccgttcag 3840
```

```
cccgaccgct gcgccttatc cggtaactat cgtcttgagt ccaacccggt aagacacgac 3900
ttatcgccac tggcagcagc cactggtaac aggattagca gagcgaggta tgtaggcggt 3960
gctacagagt tcttgaagtg gtggcctaac tacggctaca ctagaaggac agtatttggt 4020
atctgcgctc tgctgaagcc agttaccttc ggaaaaagag ttggtagctc ttgatccggc 4080
aaacaaacca ccgctggtag cggtggtttt tttgtttgca agcagcagat tacgcgcaga 4140
aaaaaaggat ctcaagaaga tcctttgatc ttttctacgg ggtctgacgc tcagtggaac 4200
gaaaactcac gttaagggat tttggtcatg agattatcaa aaaggatctt cacctagatc 4260
cttttaaatt aaaaatgaag ttttaaatca atctaaagta tatatgagta aacttggtct 4320
gacagttacc aatgcttaat cagtgaggca cctatctcag cgatctgtct atttcgttca 4380
tccatagttg cctgactccc cgtcgtgtag ataactacga tacggagggg cttaccatct 4440
ggccccagtg ctgcaatgat accgcgagac ccacgctcac cggctccaga tttatcagca 4500
ataaccagc cagccggaag ggccgagcgc agaagtggtc ctgcaacttt atccgcctcc 4560
atccagtcta ttaattgttg ccgggaagct agagtaagta gttcgccagt taatagtttg 4620
cgcaacgttg ttgccattgc tacaggcatc gtggtgtcac gctcgtcgtt tggtatggct 4680
tcattcagct ccggttccca acgatcaagg cgagttacat gatcccccat gttgtgcaaa 4740
aaagcggtta gctccttcgg tcctccgatc gttgtcagaa gtaagttggc cgcagtgtta 4800
tcactcatgg ttatggcagc actgcataat tctcttactg tcatgccatc cgtaagatgc 4860
ttttctgtga ctggtgagta ctcaaccaag tcattctgag aatagtgtat gcggcgaccg 4920
agttgctctt gcccgcgtc aatacgggat aataccgcgc cacatagcag aactttaaaa 4980
gtgctcatca ttggaaaacg ttcttcgggg cgaaaactct caaggatctt accgctgttg 5040
agatccagtt cgatgtaacc cactcgtgca cccaactgat cttcagcatc ttttactttc 5100
accagcgttt ctgggtgagc aaaaacagga aggcaaaatg ccgcaaaaaa gggaataagg 5160
gcgacacgga aatgttgaat actcatactc ttcctttttc aatattattg aagcatttat 5220
cagggttatt gtctcatgag cggatacata tttgaatgta tttagaaaaa taaacaaata 5280
ggggttccgc gcacatttcc ccgaaaagtg ccacctgaac gaagcatctg tcttcatttt 5340
tgtagaacaa aaatgcaacg cgagagcgct aattttttca acaaaaatc tgagctgcat 5400
ttttacagaa cagaaatgca acgcgaaagc gctattttac caacgaagaa tctgtgcttc 5460
atttttgtaa aacaaaaatg caacgcgaga gcgctaattt ttcaaacaaa gaatctgagc 5520
tgcatttta cagaacagaa atgcaacgcg agagcgctat tttaccaaca aagaatctat 5580
acttcttttt tgttctacaa aaatgcatcc cgagagcgct attttctaa caaagcatct 5640
tagattactt tttttctcct ttgtgcgctc tataatgcag tctcttgata acttttttgca 5700
ctgtaggtcc gttaaggtta gaagaaggct actttggtgt ctattttctc ttccataaaa 5760
aaagcctgac tccacttccc gcgtttactg attactagcg aagctgcggg tgcatttttt 5820
caagataaag gcatcccga ttatattcta taccgatgtg gattgcgcat actttgtgaa 5880
cagaaagtga tagcgttgat gattcttcat tggtcagaaa attatgaacg gtttcttcta 5940
ttttgtctct atatactacg tataggaaat gtttacattt tcgtattgtt ttcgattcac 6000
tctatgaata gttcttacta caatttttt gtctaaagag taatactaga gataaacata 6060
aaaaatgtag aggtcgagtt tagatgcaag ttcaaggagc gaaaggtgga tgggtaggtt 6120
atatagggat atagcacaga gatatatagc aaagagatac ttttgagcaa tgtttgtgga 6180
agcggtattc gcaatatttt agtagctcgt tacagtccgg tgcgttttttg gttttttgaa 6240
agtgcgtctt cagagcgctt ttggttttca aaagcgctct gaagttccta tactttctag 6300
agaataggaa cttcggaata ggaacttcaa agcgtttccg aaaacgagcg cttccgaaaa 6360
tgcaacgcga gctgcacaca tacagctcac tgttcacgtc gcacctatat ctgcgtgttg 6420
cctgtatata tatatacatg agaagaacgg catagtgcgt gtttatgctt aaatgcgtac 6480
ttatatgcgt ctatttatgt aggatgaaag gtagtctagt acctcctgtg atattatccc 6540
attccatgcg gggtatcgta tgcttccttc agcactaccc tttagctgtt ctatatgctg 6600
ccactcctca attggattag tctcatcctt caatgctatt atttcctttg atattggatc 6660
atactaagaa accattatta tcatgacatt aacctataaa aataggcgta tcacgaggcc 6720
ctttcgtctc gcgcgtttcg gtgatgacgg tgaaaacctc tgacacatgc agctcccgga 6780
gacggtcaca gcttgtctgt aagcggatgc cgggagcaga caagcccgtc agggcgcgtc 6840
agcgggtgtt ggcgggtgtc ggggctggct taactatgcg gcatcagagc agattgtact 6900
gagagtg                                                           6907
SEQ ID NO: 65           moltype = DNA  length = 8270
FEATURE                 Location/Qualifiers
misc_feature            1..8270
                        note = pYP096
source                  1..8270
                        mol_type = other DNA
                        organism = synthetic construct
SEQUENCE: 65
acaggaaaca gctatgacca tgattacgcc aagcgcgcaa ttaaccctca ctaaagggaa 60
caaaagctgg agctcaagtc caatgctagt agagaagggg ggtaacaccc ctccgcgctc 120
ttttccgatt ttttctaaa ccgtggaata tttcggatat cctttttgtg ctttaccatt 180
tacaatatgg acttcctctt ttctggcaac caaacccata catcgggatt cctataaact 240
cttcgttggt ctccctaaca tgtaggtggc ggagggggaga tatacaatag aacagatacc 300
agacaagaca taatgggcta aacaagacta caccaattac actgcctcat tgatggtggt 360
acataacgaa ctaatactgt agccctagac ttgatagcca tcatcatatc gaagtttcac 420
taccctttt ccatttgcca tctattgaag taataatagg gcatgcaac ttcttttctt 480
tttttttctt ttctctctcc cccgttgttg tctcaccata tccgcaatga caaaaaaatg 540
atggaagaca ctaaaggaaa aaattaacga caaagacagc accaacagat gtcgttgttc 600
cagagctgat gagggggtatc tcgaagcaca cgaaactttt tccttccttc attcacgcac 660
actactctct aatgagcaac ggtatacggc cttcttcca gttacttgaa tttgaaataa 720
aaaaaagttt gctgtcttgc tatcaagtat aaatagacct gcaattatta atcttttgtt 780
tcctcgtcat tgttctcgtt ccctttcttc cttgtttctt tttctgcaca atatttcaag 840
ctataccaag catacaatca actatctcat atacagttaa catgcatcac catcaccatc 900
acactagtgg atccatgaga aaggttgaaa ttattaccgc tgaacaagct gctcaattgg 960
ttaaggacaa cgacaccatt acctctattg gtttcgtttc ttctgctcac ccagaagctt 1020
tgaccaaggc tttggaaaag agattcttgg acaccaacac cccacaaaac ttgacctaca 1080
```

```
tttacgctgg ttctcaaggt aagagagacg gtagagctgc tgaacacttg gctcacaccg  1140
gtttgttgaa gagagctatt attggtcact ggcaaaccgt tccagctatt ggtaagttgg  1200
ctgttgaaaa caagattgaa gcttacaact tctctcaagg taccttggtt cactggttca  1260
gagctttggc tggtcacaag ttgggtgttt tcaccgacat tggtttggaa accttcttgg  1320
acccaagaca attgggtggt aagttgaacg acgttaccaa ggaagacttg gttaagttga  1380
ttgaagttga cggtcacgaa caattgttct acccaacctt cccagttaac gttgctttct  1440
tgagaggtac ctacgctgac gaatctggta acattactat ggacgaagaa attggtccat  1500
tcgaatctac ctctgttgct caagctgttc acaactgtgg tggtaaggtt gttgttcaag  1560
ttaaggacgt tgttgctcac ggttcttttgg acccaagaat ggttaagatt ccaggtattt  1620
acgttgacta cgttgttgtt gctgctccag aagaccacca acaaacctac gactgtgaat  1680
acgacccatc tttgtctggt gaacacagag ctccagaagg tgctaccgac gctgctttgc  1740
caatgtctgc taagaagatt attggtagaa gaggtgcttt ggaattgacc gaaaacgctg  1800
ttgttaactt gggtgttggt gctccagaat acgttgcttc tgttgctggt gaagaaggta  1860
ttgctgacac cattaccttg accgttgaag gtggtgctat tggtggtgtt ccacaaggtg  1920
gtgctagatt cggttcttca agaaacgctg acgctattat tgaccacacc taccaattcg  1980
acttctacga cggtggtggt ttggacattg cttacttggg tttggctcaa tgtgacggtt  2040
ctggtaacat taacgtttct aagttcggta ccaacgttgc tggttgtggt ggtttcccaa  2100
acatttctca acaaaccccca aacgtttact tctgtggtac cttcaccgct ggtggtttga  2160
agattgctgt tgaagacggt aaggttaaga ttttgcaaga aggtaaggct aagaagttca  2220
ttaaggctgt tgaccaaatt accttcaacg gttcttacgc tgctagaaac ggtaagcacg  2280
ttttgtacat taccgaaaga tgtgttttcg aattgaccaa ggaaggtttg aagttgattg  2340
aagttgctcc aggtattgac attgaaaagg acatttttgc tcacatggac ttcaagcaca  2400
ttattgacaa cccaaagttg atggacgcta gattgttcca agacggtcca atgggtttga  2460
agaagtaacc cgggctgcag gaattcgata tcaagcttat cgataccgtc gacctcgagt  2520
gaagttttgt tagaaaataa atcatttttt aattgagcat tcttattcct attttattta  2580
aatagttta tgtattgtta gctacataca acagttaa tcaaattttc tttttcccaa  2640
gtccaaaatg gaggtttatt ttgatgaccc gcatgcgatt atgttttgaa agtataagac  2700
tacatacatg tacatatatt taaacatgta aacccgtcca ttatattgct tactttcttc  2760
tttttttgccg ttttgacttg gacctctggt ttgctatttc cttacaatct ttgctacaat  2820
cggccggtac ccaattcgcc ctatagtgag tcgtattacg cggcgctcact ggccgtcgtt  2880
ttacaacgtc gtgactggga aaaccctggc gttacccaac ttaatcgcct tgcagcacat  2940
cccccttttcg ccagctggcg taatagcgaa gaggcccgca ccgatcgccc ttcccaacag  3000
ttgcgcagcc tgaatggcga atggcgcgac gcgccctgta gcggcgcatt aagcgcggcg  3060
ggtgtggtgg ttacgcgcag cgtgaccgct acacttgcca gcgccctagc gcccgctcct  3120
ttcgctttct tcccttcctt tctcgccacg ttcgccggct ttccccgtca agctctaaat  3180
cggggggctcc ctttagggtt ccgatttagt gctttacggc acctcgaccc caaaaaactt  3240
gattaggtg atggttcacg tagtgggcca tcgccctgat agacggtttt tcgccctttg  3300
acgttggagt ccacgttctt taatagtgga ctcttgttcc aaactggaac aacactcaac  3360
cctatctcgg tctattcttt tgatttataa gggattttgc cgatttcggc ctattggtta  3420
aaaaatgagc tgatttaaca aaaatttaac gcgaattta acaaaatatt aacgtttaca  3480
atttcctgat gcggtatttt ctccttacgc atctgtgcgg tatttcacac cgcataggca  3540
agtgcacaaa caatacttaa ataaatacta ctcagtaata acctatttct tagcattttt  3600
gacgaaattt gctattttgt tagagtcttt tacaccattt gtctccacac ttccgcttac  3660
atcaacacca ataacgccat ttaatctaag cgcatcacca acatttttctg gcgtcagtcc  3720
accagctaac ataaaatgta agctttcggg gctctcttgc cttccaaccc agtcagaaat  3780
cgagttccaa tccaaaagtt cacctgtccc acctgcttcc gaatcaaaca agggaataaa  3840
cgaatgaggt ttctgtgaag ctgcactgag tagtatgttg cagtcttttg gaaatacgag  3900
tcttttaata actggcaaac cgaggaactc ttggtattct tgccacgact catctccatg  3960
cagttggacg atatcaatgc cgtaatcatt gaccagagcc aaaacatcct ccttaggttg  4020
attacgaaac acgccaacca agtatttcgg agtgcctgaa ctatttttat atgcttttac  4080
aagacttgaa atttttcctt g caataaccgg gtcaattgtt ctcttttcta tgggcacaca  4140
tataataccc agcaagtcag catcggaatc tagagcacat tctgcggcct ctgtgctctg  4200
caagccgcaa actttcacca atggaccaga actacctgtg aaattaataa cagacatact  4260
ccaagctgcc tttgtgtgct taatcacgta tactcacgtg ctcaatagtc accaatgccc  4320
tccctcttgg ccctctcctt ttcttttttc gaccgaatta attcttaatc ggcaaaaaaa  4380
gaaaagctcc ggatcaagat tgtacgtaag gtgacaagct attttttcaat aaagaatatc  4440
ttccactact gccatctggc gtcataactg caaagtacac atatattacg atgctgtcta  4500
ttaaatgctt cctatattat atatatagta atgtcgttta tggtgcactc tcagtacaat  4560
ctgctctgat gccgcatagt taagccagcc ccgacacccg ccaacacccg ctgacgcgcc  4620
ctgacgggct tgtctgctcc cggcatccgc ttacagacaa gctgtgaccg tctccgggag  4680
ctgcatgtgt cagaggtttt caccgtcatc accgaaacgc gcgagacgaa agggcctcgt  4740
gatacgccta ttttttatagg ttaatgtcat gataataatg gtttcttaat atgatccaat  4800
atcaaaggaa atgatagcat tgaaggatga gactaatcca ttgaggagt ggcagcatat  4860
agaacgcta aagggtagtg ctgaaggaag catacgatac cccgcatgga atgggataat  4920
atcacaggag gtactagact accttcatc ctacataaat agacgcatat aagtacgcat  4980
ttaagcataa acacgcacta tgccgttctt ctcatgtata tatatataca ggcaacacgc  5040
agatataggt gcgacgtgaa cagtgagctg tatgtgcgca gctcgcgttg catttttcgga  5100
agcgctcgtt ttcggaaacg cttttgaagtt cctattccga agttcctatt ctctagaaag  5160
tataggaact tcagagcgct tttgaaaacc aaaagcgctc tgaagacgca ctttcaaaaa  5220
accaaaacg caccggactg taacgagcta ctaaaatatt gcgaataccg cttccacaaa  5280
cattgctcaa aagtatctct ttgctatata tctctgtgct atatccctat ataacctacc  5340
catccacctt tcgctccttg aacttgcatc taaactcgac ctctacattt tttatgttta  5400
tctctagtat tactctttag acaaaaaaat tgtagtaaga actattcata gagtgaatcg  5460
aaaacaatac gaaaatgtaa acatttccta tacgtagtat atagagacaa aatagaagaa  5520
accgttcata attttctgac caatgaagaa tcatcaacgc tatcactttc tgttcacaaa  5580
gtatgcgcaa tccacatcgg tatagaatat aatcggggat gcctttatct tgaaaaatg  5640
cacccgcagc ttcgctagta atcagtaaac gcgggaagtg gagtcaggct ttttttatgg  5700
aagagaaaat agacaccaaa gtagccttct tctaacctta acggacctac agtgcaaaaa  5760
gttatcaaga gactgcatta tagagcgcac aaaggagaaa aaaagtaatc taagatgctt  5820
```

```
tgttagaaaa atagcgctct cgggatgcat ttttgtagaa caaaaaagaa gtatagattc    5880
tttgttggta aaatagcgct ctcgcgttgc atttctgttc tgtaaaaatg cagctcagat    5940
tctttgtttg aaaaattagc gctctcgcgt tgcattttg ttttacaaaa atgaagcaca     6000
gattcttcgt tggtaaaata gcgctttcgc gttgcatttc tgttctgtaa aaatgcagct    6060
cagattcttt gtttgaaaaa ttagcgctct cgcgttgcat ttttgttcta caaaatgaag    6120
cacagatgct tcgttcaggt ggcacttttc ggggaaatgt gcgcggaacc cctatttgtt    6180
tattttcta aatacattca aatatgtatc cgctcatgag acaataaccc tgataaatgc     6240
ttcaataata ttgaaaaagg aagagtatga gtattcaaca tttccgtgtc gcccttattc    6300
ccttttttgc ggcattttgc cttcctgttt tgctcaccca gaaacgctg gtgaaagtaa     6360
aagatgctga agatcagttg ggtgcacgag tgggttacat cgaactggat ctcaacagcg    6420
gtaagatcct tgagagtttt cgccccgaag aacgttttcc aatgatgagc acttttaaag    6480
ttctgctatg tggcgcggta ttatcccgta ttgacgccgg gcaagagcaa ctcggtcgcc    6540
gcatacacta ttctcagaat gacttggttg agtactcacc agtcacagaa aagcatctta    6600
cggatggcat gacagtaaga gaattatgca gtgctgccat aaccatggat gataacactg    6660
cggccaactt acttctgaca acgatcggag gaccgaagga gctaaccgct tttttgcaca    6720
acatggggga tcatgtaact cgccttgatc gttgggaacc ggagctgaat gaagccatac    6780
caaacgacga gcgtgacacc acgatgcctg tagcaatggc aacaacgttg cgcaaactat    6840
taactggcga actacttact ctagcttccc ggcaacaatt aatagactgg atggaggcgg    6900
ataaagttgc aggaccactt ctgcgctcgg cccttccggc tggctggttt attgctgata    6960
aatctggagc cggtgagcgt gggtctcgcg gtatcattgc agcactgggg ccagatggta    7020
agccctcccg tatcgtagtt atctacacga cggggagtca ggcaactatg gatgaacgaa    7080
atagacagat cgctgagata ggtgcctcac tgattaagca ttggtaactg tcagaccaag    7140
tttactcata tatactttag attgatttaa aacttcattt taatttaaa aggatctagg     7200
tgaagatcct ttttgataat ctcatgacca aaatccctta acgtgagttt cgttccact    7260
gagcgtcaga ccccgtagaa aagatcaaag gatcttcttg atccttttt tttctgcgcg    7320
taatctgctg cttgcaaaca aaaaaaccac cgctaccagc ggtggtttgt ttgccggatc    7380
aagagctacc aactcttttt ccgaaggtaa ctggcttcag cagagcgcag ataccaaata    7440
ctgtccttct agtgtagccg tagttaggcc accacttcaa gaactctgta gcaccgccta    7500
catacctcgc tctgctaatc ctgttaccag tggctgctgc cagtggcgat aagtcgtgtc    7560
ttaccgggtt ggactcaaga cgatagttac cggataagc gcagcggtcg ggctgaacgg    7620
ggggttcgtg cacacagccc agcttggagc gaacgaccta caccgaactg agatacctac    7680
agcgtgagct atgagaaagc gccacgcttc ccgaagggag aaaggcggac aggtatccgg    7740
taagcggcag ggtcggaaca ggagagcgca cgagggagct tccagggga aacgcctggt     7800
atctttatag tcctgtcggg tttcgccacc tctgacttga gcgtcgattt ttgtgatgct    7860
cgtcaggggg gcggagccta tggaaaaacg ccagcaacgc ggcctttta cggttcctgg    7920
ccttttgctg gccttttgct cacatgttct ttcctgcgtt atccctgat tctgtggata    7980
accgtattac cgcctttgag tgagctgata ccgctcgccg cagccgaacg accgagcgca    8040
gcgagtcagt gagcgaggaa gcggaagagc gcccaatacg caaaccgcct ctccccgcgc    8100
gttggccgat tcattaatgc agctggcacg acaggtttcc cgactggaaa gcgggcagtg    8160
agcgcaacgc aattaatgtg agttacctca ctcattaggc accccaggct ttacacttta   8220
tgcttccggc tcctatgttg tgtggaattg tgagcggata caatttcac                8270

SEQ ID NO: 66        moltype = DNA   length = 8347
FEATURE              Location/Qualifiers
misc_feature         1..8347
                     note = pYP106
source               1..8347
                     mol_type = other DNA
                     organism = synthetic construct
SEQUENCE: 66
ctcaagtcca atgctagtag agaagggggg taacacccct ccgcgctctt ttccgatttt     60
tttctaaacc gtggaatatt tcggatatcc ttttgttgtt tccgggtgta caatatggac    120
ttcctctttt ctgcaaacca aacccataca tcgggattcc tataatacct tcgttggtct    180
ccctaacatg taggtggcgg aggggagata tacaatagaa cagataccag acaagacata    240
atgggctaaa caagactaca ccaattacac tgcctcattg atggtggtac ataacgaact    300
aatactgtag ccctagactt gatagccatc atcatatcga agtttcacta ccctttttcc    360
atttgccatc tattgaagta ataataggcg catgcaactt cttttctttt ttttctttt     420
ctctctcccc cgttgttgtc tcaccatatc cgcaatgaca aaaaaatgat ggaagacact    480
aaaggaaaaa attaacgaca aagacagcac caacagatgt cgttgttcca gagctgatga    540
ggggtatctc gaagcacacg aaactttttc cttccttcat tcacgcacac tactcctaa     600
tgagcaacgg tatacggcct tccttccagt tacttgaatt tgaaataaaa aaagtttgc     660
tgtcttgcta tcaagtataa atagacctgc aattattaat cttttgtttc ctcgtcattg    720
ttctcgttcc ctttcttcct tgtttctttt tctgcacaat atttcaagct ataccaagca    780
tacaatcaac tatctcatat acagttaaca tgcatcacca tcaccatcac actagtcggt    840
ccatgaaggt tattaccgca agagaagctg ctgcattgt tcaagacggt tggaccgttg    900
cttctgctgg tttcgttggt gctggtcacg ctgaagctgt taccgaagca ttggaacaaa    960
gattcttgca atctggattg ccaagagact tgaccttggt ttactctgct ggacaaggtg   1020
acagaggtgc tagaggtgtt aatcacttcg gtaacgctgg tatgaccgct tctattgttg   1080
gtggtcactg gagatctgct accagattgg ctacccttgc tatgcgtgaa caatgtgaag   1140
gttacaactt gccacaaggt gttttgaccc cctatacag agctattgct ggtggtaagc    1200
caggtgttat gaccaagatt ggtttgcaca ccttcgttga cccaagaacc gctcaagacg   1260
ctagatacca cggtggtgct gttaatgaaa gagctagaca agctatagct gaaggtaagg   1320
cttgttgggt tgacgctgtt gacttcagag gtgacgaata cttgttctac ccatcttttcc   1380
caattcactc tgctttgatt agatgtaccg tagaggtaac ttgtcttaga               1440
acagagaagc attccaccac gaattgttgg ctatgggtca agctgctcac aactctggtg   1500
gtattgttat tgctcaagtt gaatctttgg ttgaccacca cgaaattttg caagctattc   1560
acgttccagg tattttggtt gactacgttg tgtttgtga caaccagct aaccaccaaa    1620
tgaccttcgc tgaatcttac aacccagctt acgttacccc ttgcaaggt gaagctgctg    1680
ttgctgaagc tgaagctgct ccagttgcag ctggtccatt ggacgctaga accattgttc   1740
```

```
aaaggagagc tgttatggaa ttggctagaa gggctccaag agttgttaat ttgggtgttg   1800
gtatgccagc tgctgttggt atgttggctc accaagcagg attggacggt ttcaccttga   1860
ccgttgaagc tggtccaatt ggtggtaccc cagctgacgg tttgtctttc ggagcttctg   1920
cttacccaga agctgttgtt gaccaaccag ctcaattcga cttctacgaa ggtggtggta   1980
ttgacttggc tatttttggt ttggctgaat tggacggtca cggtaacgtt aatgtttcta   2040
agttcggtga aggtgaaggt gcttctatag ctggtgttgg tggtttcatt aacattaccc   2100
aatctgctag agctgttgtt ttcatgggta ccttgaccgc tggtggattg gaagttagag   2160
ctggtgacgg tggtttgcaa attgttagag aaggtagagt taagaagatt gttcctgaag   2220
tttctcactt gtcttttcaac ggaccatacg ttgcttcttt gggtattcca gttttgtaca   2280
ttaccgaaag agctgttttc gaaatgagag caggtgctga cggtgaagct agattgacct   2340
tggttgaaat tgctccaggt gttgacttgc aaagagacgt tttggaccaa tgttctaccc   2400
caattgctgt agctcaagac ttgagagaaa tggacgctag attgttccaa gctgaccat    2460
tgcacttgta ataacccggg ctgcaggaat tcgatatcaa gcttatcgat accgtcgacc   2520
tcgaggaagt tttgttagaa aataaatcat ttttaattg agcattctta ttcctattt     2580
atttaaatag ttttatgtat tgttagctac atacaacagt ttaaatcaaa tttctttt     2640
cccaagtcca aaatggaggt ttattttgat gacccgcatg cgattatgtt ttgaaagtat   2700
aagactacat acatgtacat atatttaaac atgtaaaccc gtccattata ttgcttactt   2760
tctctttttt tgccgttttg acttggacct ctggtttgct atttccttac aatctttgct   2820
acaatcggcc ggtacccaat tcgccctata gtgagtcgta ttacgcgcgc tcactgccg    2880
tcgtttttaca acgtcgtgac tgggaaaacc ctggcgttac ccaacttaat cgccttgcag   2940
cacatccccc tttcgccagc tggcgtaata gcgaagaggc ccgcaccgat cgcccttccc   3000
aacagttgcg cagcctgaat ggcgaatggc gcgacgcgcc ctgtagcgcc gcattaagcg   3060
cggcgggtgt ggtggttacg cgcagcgtga ccgctacact tgccagcgcc ctagcgccc   3120
ctcctttcgc tttcttccct tcctttctcg ccacgttcgc cggctttccc cgtcaagctc   3180
taaatcgggg gctcccttta gggttccgat ttagtgcttt acggcacctc gaccccaaaa   3240
aacttgatta gggtgatgt tcacgtagtg ggccatcgcc ctgatagacg gttttcgcc    3300
ctttgacgtt ggagtccacg ttctttaata gtggactctt gttccaaact ggaacaacac   3360
tcaaccctat ctcggtctat tcttttgatt tataagggat tttgccgatt tcggcctatt   3420
ggttaaaaaa tgagctgatt taacaaaaat ttaacgcgaa ttttaacaaa atattaacgt   3480
ttacaattc ctgatgcggt atttttctcct tacgcatctg tgcggtattt cacaccgcat   3540
aggcaagtgc acaaacaata cttaaataaa tactactcag taataaccta tttcttagca   3600
ttttttgacga aatttgctat tttgttagag tcttttacac catttgtctc cacacctccg   3660
cttacatcaa caccaataac gccatttaat ctaagcgcat caccaacatt ttctggcgtc   3720
agtccaccag ctaacataaa atgtaagctt tcggggctct cttgccttcc aacccagtca   3780
gaaatcgagt tccaatccaa aagttcacct gtcccacctg cttctgaatc aaacaaggga   3840
ataaacgaat gaggtttctg tgaagctgca ctgagtagta tgttgcagtc ttttggaaat   3900
acgagtcttt taataactgg caaaccgagg aactcttggt attcttgcca cgactcatct   3960
ccatgcagtt ggacgatatc aatgccgtaa tcattgacca gagccaaaac atcctcctta   4020
ggttgattac gaaacacgcc aaccaagtat tcgagtgc ctgaactatt tttatatgt     4080
tttacaagac ttgaaatttt ccttgcaata accgggtcaa ttgttctctt tctattgggc   4140
acacatataa tacccagcaa gtcagcatcg gaatctagag cacattctgc ggcctctgtg   4200
ctctgcaagc cgcaaacttt caccaatgga ccagaactac ctgtgaaatt aataacagac   4260
atactccaag ctgcctttgt gtgcttaatc acgtatactc acgtgctcaa tagtcaccaa   4320
tgccctccct cttggccctc tccttttctt ttttcgaccg aattaattct taatcggcaa   4380
aaaaagaaaa gctccggatc aagattgtac gtaaggtgac aagctatttt tcaataaaga   4440
atatcttcca ctactgccat ctggcgtcat aactgcaaag tacacatata ttacgatgct   4500
gtctattaaa tgcttcctat attatatata tagtaatgtc gtttatggtg cactctcagt   4560
acaatctgct ctgatgccgc atagttaagc cagccccgac acccgccaac acccgctgac   4620
gcgccctgac gggcttgtct gctcccggca tccgcttaca gacaagctgt gaccgtctcc   4680
gggagctgca tgtgtcagag gttttcaccg tcatcaccga aacgcgcgag acgaaagggc   4740
ctcgtgatac gcctattttt ataggttaat gtcatgataa taatggttc ttaatatgat    4800
ccaatatcaa aggaaatgat agcattgaag gatgagacta atccaattga ggagtggcag   4860
catatagaac agctaaaggg tagtgctgaa ggaagcatac gatacccgc atggaatggg   4920
ataatatcac aggaggtact agactacctt tcatcctaca taaatagacg catataagta   4980
cgcatttaag cataaacacg cactatgccg ttcttctcat gtatatatat atacaggcaa   5040
cacgcagata taggtgcgac gtgaacagtg agctgtatgt gcgcagctcg cgttgcattt   5100
tcggaagcgc tcgttttcgg aaacgctttg aagttcctat tccgaagttc ctattctcta   5160
gaaagtatag gaacttcaga gcgcttttga aaaccaaaag cgctctgaag acgcactttc   5220
aaaaaaccaa aaacgcaccg gactgtaacg agctactaaa atattgcgaa taccgcttcc   5280
acaaacattg ctcaaaagta tctctttgct atatatctct gtgctatatc cctatataac   5340
ctacccatcc acctttcgct ccttgaactt gcatctaaac tcgacctcta catttttttat  5400
gtttatctct agtattactc tttagacaaa aaaattgtag taagaactat tcatagagtg   5460
aatcgaaaac aatacgaaaa tgtaaacatt tcctatacgt agtatataga gacaaaatag   5520
aagaaaccgt tcataatttt ctgaccaatg aagaatcatc aagatccgtc ctttctgtct   5580
acaaagtatg cgcaatccac atcggtatag aatataatcg gggatgcctt tatcttgaaa   5640
aaatgcaccc gcagcttcgc tagtaatcag taaacgcggg aagtggagtc aggctttttt   5700
tatggaagag aaaatagaca ccaaagtagc cttcttctaa ccttaacgga cctacagtgc   5760
aaaaagttat caagagactg cattatagag cgcacaaagg agaaaaaaag taatctaaga   5820
tgctttgtta gaaaaatagc gctctcggga tgcattttt tagaacaaaa aagaagtata   5880
gattcttttgt tggtaaaata gcgctctcgc gttgcatttc tgttctgtaa aaatgcagct   5940
cagattcttt gtttgaaaaa ttagcgctct cgcgttgcat ttttgtttta caaaatgaa   6000
gcacagattc ttcgttggta aaatagcgct ttcgcgttgc atttctgttc tgtaaaaatg   6060
cagctcagat tctttgtttg aaaaattagc gctctcgcgt tgcattttg ttctacaaa    6120
tgaagcacag atgcttcgtt caggtgcac ttcggaga aatgtgcgcg gaacccctat      6180
ttgtttattt ttctaaatac attcaaatat gtatccgctc atgagacaat aaccctgata   6240
aatgcttcaa taatattgaa aaaggaagag tatgagtatt caacatttcc gtgtcgccct   6300
tattcccttt tttgcggcat tttgccttcc tgttttgct cacccagaaa cgctggtgaa    6360
agtaaaagat gctgaagatc agttgggtgc acgagtgggt tacatcgaac tggatctcaa   6420
cagcggtaag atccttgaga gttttcgccc cgaagaacgt tttccaatga tgagcacttt   6480
```

```
taaagttctg ctatgtggcg cggtattatc ccgtattgac gccgggcaag agcaactcgg   6540
tcgccgcata cactattctc agaatgactt ggttgagtac tcaccagtca cagaaaagca   6600
tcttacggat ggcatgacag taagagaatt atgcagtgct gccataacca tgagtgataa   6660
cactgcggcc aacttacttc tgacaacgat cggaggaccg aaggagctaa ccgctttttt   6720
gcacaacatg ggggatcatg taactcgcct tgatcgttgg gaaccgggag tgaatgaagc   6780
cataccaaac gacgagcgtg acaccacgat gcctgtagca atggcaacaa cgttgcgcaa   6840
actattaact ggcgaactac ttactctagc ttcccggcaa caattaatag actggatgga   6900
ggcggataaa gttgcaggac cacttctgcg ctcggccctt ccggctggct ggtttattgc   6960
tgataaatct ggagccggtg agcgtgggtc tcgcggtatc attgcagcac tggggccaga   7020
tggtaagccc tcccgtatcg tagttatcta cacgacgggg agtcaggcaa ctatggatga   7080
acgaaataga cagatcgctg agataggtgc ctcactgatt aagcattggt aactgtcaga   7140
ccaagtttac tcatatatac tttagattga tttaaaactt catttttaat ttaaaaggat   7200
ctaggtgaag atcctttttg ataatctcat gaccaaaatc ccttaacgtg agttttcgtt   7260
ccactgagcg tcagaccccg tagaaaagat caaaggatct tcttgagatc ctttttttct   7320
gcgcgtaatc tgctgcttgc aaacaaaaaa accaccgcta ccagcggtgg tttgtttgcc   7380
ggatcaagag ctaccaactc tttttccgaa ggtaactggc ttcagcagag cgcagatacc   7440
aaatactgtc cttctagtgt agccgtagtt aggccaccac ttcaagaact ctgtagcacc   7500
gcctacatac ctcgctctgc taatcctgtt accagtggct gctgccagtg gcgataagtc   7560
gtgtcttacc gggttggact caagacgata gttaccggat aaggcgcagc ggtcgggctg   7620
aacggggggt tcgtgcacac agcccagctt ggagcgaacg acctacaccg aactgagata   7680
cctacagcgt gagctatgag aaagcgccac gcttcccgaa gggagaaagg cggacaggta   7740
tccggtaagc ggcagggtcg gaacaggaga gcgcacgagg gagcttccag ggggaaacgc   7800
ctggtatctt tatagtcctg tcgggtttcg ccacctctga cttgagcgtc gatttttgtg   7860
atgctcgtca gggggggcgga gcctatgaaa aaacgccagc aacgcggcct ttttacggtt   7920
cctggccttt tgctggcctt ttgctcacat gttctttcct gcgttatccc ctgattctgt   7980
ggataaccgt attaccgcct ttgagtgagc tgataccgct cgccgcagcc gaacgaccga   8040
gcgcagcgag tcagtgagcg aggaagcgga gagcgcccaa tacgcaaacc gcctctcccc   8100
cgcgcgttgg ccgattcatt aatgcagctg gcacgacagg tttcccgact ggaaagcggg   8160
cagtgagcgc aacgcaatta atgtgagtta cctcactcat taggcacccc aggctttaca   8220
ctttatgctt ccggctccta tgttgtgtgg aattgtgagc ggataacaat ttcacacagg   8280
aaacagctat gaccatgatt acgccaagcg cgcaattaac cctcactaaa gggaacaaaa   8340
gctggag                                                              8347
```

SEQ ID NO: 67  moltype = DNA  length = 7645  
FEATURE     Location/Qualifiers  
misc_feature   1..7645  
         note = pYP137  
source      1..7645  
         mol_type = other DNA  
         organism = synthetic construct SEQUENCE: 67
```
gagctcgtag gaacaatttc gggcccctgc gtgttcttct gaggttcatc ttttacattt   60
gcttctgctg gataatttc agaggcaaca aggaaaaatt agatggcaaa aagtcgtctt    120
tcaaggaaaa atccccacca tctttcgaga tccctgtaa cttattggca actgaaagaa    180
tgaaaaggag gaaaatacaa aatatactag aactgaaaaa aaaaaagtat aaatagagac    240
gatatatgcc aatacttcac aatgttcgaa tctattcttc atttgcagct attgtaaaat    300
aataaaacat caagaacaaa caagctcaac ttgtcttttc taagaacaaa gaataaacac    360
aaaaacaaaa agtttttta attttaatca aaaagttaac atgcatcacc atcaccatca    420
cactagtgga tccatggcag tcctatcctc agctgatagg gctagtaacg aaaagaaggt    480
aaagtcatct tacttcgact tgcctccaat ggaaatgtca gttgcattcc cacaagccac    540
accagcttct acgtttcccc cgtgcacttc tgattactat cactttaatg acttgttgac    600
accagaagag caggcaatta gaaagaaggt aagagagtgt atggaaaaag aagttgctcc    660
gattatgact gaatactggg agaaggcaga gtttccattt catataacac ctaagctagg    720
ggctatggga gttgcaggcg gatctatcaa aggttacggt tgtccaggcc taagcatcac    780
agccaatgct atcgcaacag ccgaaattgc aagggttgat gccagttgtt ctacgttcat    840
tttagtccat agttctttag gaatgctgac aattgcttta tgcggtagtg aagcacaaaa    900
agagaaatac cttccatcct tggcacaact taatacagtg gcctgctggg cgcttactga    960
gccagataat ggttctgatg cttcaggatt gggaaccaca gcgactaagg tggaaggcgg    1020
ttggaagatt aacggtcaaa aaaggtggat aggaaactca acattcgcgg atttattgat    1080
tatctttgct agaaacacga ctaccaacca aatcaacggc ttcattgtaa agaaagatgc    1140
tcctggctta aaagcaacca aaatccctaa taaaattggt ttgaggatgg tacaaaacgg    1200
ggatatcttg ttacagaacg tgtttgtgcc cgacgaagat cgtctacccg tgttaattc    1260
tttccaagac acttccaagg tattagcagt ctcacgtgtt atggtagctt ggcagccatt   1320
tggtatctct atgggtatct acgatatgtg tcatagatac ctgaaagaaa ggaagcagtt   1380
tggagctcct ttagctgctt ttcaacttaa ccagcaaaaa ttggtacaaa tgttaggaaa   1440
tgttcaagcg atgttcctta tgggctgag attgtgtaag ttatacgaaa ctggtcaaat   1500
gacacctggt caggcgtcat taggtaaggc ttggatatcc tctaaggcaa gagaaacagc   1560
aagtttggc agagaacttt taggtggaaa cggtattttg gccgatttcc tagttgcgaa   1620
agcattctgt gacttggagc ctatatacac atacgaaggg acttacgata ttaatacatt   1680
agtgacgggg agagaagtta caggcattgc tagtttcaaa ccagctacaa ggtctagatt   1740
ataagcttat cgataccgtc gacctcgagt catgtaatta gttatgtcac gcttacattc   1800
acgccctccc cccacatccg ctctaaccga aaggaagga gttagacaac ctgaagtcta   1860
ggtccctatt tatttttta tagttatgtt agtattaaga acgttattta tatttcaaat   1920
ttttcttttt tttctgtaca gacgcgtgta cgcatgtaac attatactga aaaccttgct   1980
tgagaaggtt ttgggacgct cgaaggcttt aatttgcggc cggtacccaa ttcgccctat   2040
agtgagtcgt attacgcgcg ctcactggcc gtcgttttac aacgtcgtga ctgggaaaac   2100
cctggcgtta cccaacttaa tcgccttgca gcacatcccc ctttcgccag ctggcgtaat   2160
agcgaagagg cccgcaccga tcgcccttcc caacagttgc gcagcctgaa tggcgaatgg   2220
cgcgacgcgc cctgtagcgg cgcattaagc gcggcgggtg tggtggttac gcgcagcgtg   2280
```

```
accgctacac ttgccagcgc cctagcgccc gctcctttcg ctttcttccc ttcctttctc 2340
gccacgttcg ccggctttcc ccgtcaagct ctaaatcggg ggctcccttt agggttccga 2400
tttagtgctt tacggcacct cgaccccaaa aaacttgatt agggtgatgg ttcacgtagt 2460
gggccatcgc cctgatagac ggttttcgc cctttgacgt tggagtccac gttctttaat 2520
agtggactct tgttccaaac tggaacaaca ctcaaccta tctcggtcta ttcttttgat 2580
ttataaggga tttttgccgat ttcggcctat tggttaaaaa atgagctgat ttaacaaaaa 2640
tttaacgcga attttaacaa aatattaacg tttacaattt cctgatgcgg tatttttctcc 2700
ttacgcatct gtgcggtatt tcacaccgca tagggtaata actgatataa ttaaattgaa 2760
gctctaatt gtgagtttag tatacatgca tttacttata atacagtttt ttagttttgc 2820
tggccgcatc ttctcaaata tgcttcccag cctgcttttc tgtaacgttc accctctacc 2880
ttagcatccc ttcccttgc aaatagtcct cttccaacaa taataatgtc agatcctgta 2940
gagaccacat catccacggt tctatactgt tgacccaatg cgtctccctt gtcatctaaa 3000
cccacaccgg gtgtcataat caaccaatcg taaccttcat ctcttccacc catgtcttct 3060
tgagcaataa agccgataac aaaatctttg tcgctcttcg caatgtcaac agtaccctta 3120
gtatattctc cagtagatag ggagcccttg catgacaatt ctgctaacat caaaaggcct 3180
ctaggttcct ttgttacttc ttctgccgcc tgcttcaaac cgctaacaat acctgggccc 3240
accacaccgt gtgcattcgt aatgtctgcc cattctgcta ttctgtatac acccgcagag 3300
tactgcaatt tgactgtatt accaatgtca gcaaatttttc tgtcttcgaa gagtaaaaaa 3360
ttgtacttgg cggataatgc ctttagcggc ttaactgtgc cctccatgga aaaatcagtc 3420
aagatatcca catgtgtttt tagtaaacaa attttgggac ctaatgcttc aactaactcc 3480
agtaattcct tggtggtacg aacatccaat gaagcacaca agtttgtttg cttttcgtgc 3540
atgatattaa atagcttggc agcaacagga ctaggatgag tagcagcagta ttcctttatat 3600
gtagctttcg acatgattta tcttcgtttc ctgcaggttt ttgttctgtg cagttgggtt 3660
aagaatactg ggcaattca tgttttctca acactacata tgcgtatata taccaatcta 3720
agtctgtgct ccttccttcg ttcttcctttc tgttcggaga ttaccgaatc aaaaaaattt 3780
caaagaaacc gaaatcaaaa aaagaataa aaaaaaaatg atgaattgaa ttgaaaagct 3840
gtggtatggt gcactctcag tacaatctgc tctgatgccg catagttaag ccagcccga 3900
cacccgccaa cacccgctga cgcgcccga cgggcttgtc tgctcccggc atccgcttac 3960
agacaagctg tgaccgtctc cgggagctgc atgtgtcaga ggttttcacc gtcatcaccg 4020
aaacgcgcga gacgaaaggg cctcgtgata cgcctatttt tataggttaa tgtcatgata 4080
ataatggttt cttagtatga tccaatatca aaggaaatga tagcattgaa ggatggagact 4140
aatccaattg aggagtggca gcatatagaa cagctaaagg gtagtgctga aggaagcata 4200
cgatacccg catggaatgg gataaatca caggaggtac tagactacct ttcatcctac 4260
ataaatagac gcatataagt acgcatttaa gcataaacac gcatatgcc gttcttctca 4320
tgtatatata tatacaggca acacgcagat ataggtgcga cgtgaacagt gagctgtatg 4380
tgcgcagctc gcgttgcatt ttcggaagcg ctcgttttcg gaaacgcttt gaagttccta 4440
ttccgaagtt cctattctct agaaagtata ggaacttcag agcgcttttg aaaaccaaaa 4500
gcgctctgaa gacgcacttt caaaaaacca aaaacgcacc ggactgtaac gagctactaa 4560
aatattgcga ataccgcttc cacaaacatt gctcaaaagt atctctttgc tatatatctc 4620
tgtgctatat ccctatataa cctacccatc caccttcgc tccttgaact tgcatctaaa 4680
ctcgacctct acattttta tgtttatctc tagtattact cttttagacaa aaaaattgta 4740
gtaagaacta ttcatagagt gaatcgaaaa caatacgaaa atgtaaacat ttcctatacg 4800
tagtatatag agacaaaata gaagaaaccg ttcataattt tctgaccaat gaagaatcat 4860
caacgctatc actttctgtt cacaaagtat gcgcaatcca catcggtata gaatataatc 4920
ggggatgcct ttatcttgaa aaaatgcacc cgcagcttcg ctagtaatca gtaaacgcgg 4980
gaagtggagt caggcttttt ttatggaaga gaaaatagac accaaagtag ccttcttcta 5040
accttaacgg acctacagtg caaaagtta tcaagagact gcattataga gcgcacaaag 5100
gagaaaaaaa gtaatctaag atgctttgtt agaaaaatag cgctctcggg atgcattttt 5160
gtagaacaaa aaagaagtat agattcttg ttggtaaaat agcgctctcg cgttgcattt 5220
ctgttctgta aaaatgcagc tcagattctt tgtttgaaaa attagcgctc tcgcgttgca 5280
ttttttttt acaaaaatga agcacagatt cttcgttggt aaaatagcgc tttcgcgttg 5340
catttctgtt ctgtaaaaat gcagctcaga ttctttgttt gaaaaattag cgctctcgcg 5400
ttgcattttt gttctacaaa atgaagcaca atgcttcgt tcaggtggca cttttcgggg 5460
aaatgtgcgc ggaacccta tttgtttatt tttctaaata cattcaaata tgtatccgct 5520
catgagacaa taaccctgat aaatgcttca ataattatga aaaaggaaga gtatgagtat 5580
tcaacatttc cgtgtcgccc ttattccctt ttttgcggca ttttgccttc ctgttttgc 5640
tcacccagaa acgctggtga agtaaaaga tgctgaagat cagttgggtg cacgagtggg 5700
ttacatcgaa ctggatctca acagcggtaa gatccttgag agttttcgcc ccgaagaacg 5760
ttttccaatg atgagcactt ttaaagttct gctatgtggc gcggtattat cccgtattga 5820
cgccgggcaa gagcaactcg gtcgccgcat acactattct cagaatgact tggttgagta 5880
ctcaccagtc acagaaaagc atcttacgga tggcatgaca gtaagagaat tatgcagtgc 5940
tgccataacc atgagtgata acactgcggc caacttactt ctgacaacga tcggaggacc 6000
gaaggagcta accgcttttt tgcacaacat ggggatcat gtaactcgcc ttgatcgttg 6060
ggaaccggag ctgaatgaag ccataccaaa tcgacgagcg gacaccacga tgcctgtaga 6120
aatggcaaca acgttgcgca aactattaac tggcgaactta cttactctag cttcccggca 6180
acaattaata gactggatgg aggcggataa agttgcagga ccacttctgc gctcggccct 6240
tccggctggc tggtttattg ctgataaatc tggagccggt gagcgtgggt ctcgcggtat 6300
cattgcagca ctgggcccag atggtaagcc ctcccgtatc gtagttatct acacgacggg 6360
gagtcaggca actatggatg aacgaaatag acagatcaggtg cctcactgat 6420
taagcattgg taactgtcag accaagttta ctcatatata ctttagattg atttaaaact 6480
tcattttta tttaaaagga tctaggtgaa gatcctttt gataatctca tgaccaaaat 6540
cccttaacgt gagttttcgt tccactgagc gtcagacccc gtagaaaaga tcaaaggatc 6600
ttcttgagat ccttttttc tgcgcgtaat ctgctgcttg caaacaaaaa aaccaccgct 6660
accagcggtg gtttgtttgc cggatcaaga gctaccaact ctttttccga aggtaactgg 6720
cttcagcaga gcgcagatac caaatactgt ccttctagtg tagccgtagt taggccacca 6780
cttcaagaac tctgtagcac cgcctacata cctcgctctg ctaatcctgt taccagtggc 6840
tgctgccagt ggcgataagt cgtgtcttac cgggttggac tcaagacgat agttaccgga 6900
taaggcgcag cggtcgggct gaacggggg ttcgtgcaca cagcccagct tggagcgaac 6960
gacctacacc gaactgagat acctacagcg tgagctatga gaaagcgcca cgcttcccga 7020
```

```
agggagaaag gcggacaggt atccggtaag cggcagggtc ggaacaggag agcgcacgag    7080
ggagcttcca gggggaaacg cctggtatct ttatagtcct gtcgggtttc gccacctctg    7140
acttgagcgt cgattttgt gatgctcgtc aggggggcgg agcctatgga aaaacgccag     7200
caacgcggcc ttttacggt tcctggcctt ttgctggcct tttgctcaca tgttctttcc     7260
tgcgttatcc cctgattctg tggataaccg tattaccgcc tttgagtgag ctgataccgc    7320
tcgccgcagc cgaacgaccg agcgcagcga gtcagtgagc gaggaagcgg aagagcgccc    7380
aatacgcaaa ccgcctctcc ccgcgcgttg gccgattcat taatgcagct ggcacgacag    7440
gtttcccgac tggaaagcgg gcagtgagcg caacgcaatt aatgtgagtt acctcactca    7500
ttaggcaccc caggctttac actttatgct tccggctcct atgttgtgtg gaattgtgag    7560
cggataacaa tttcacacag gaaacagcta tgaccatgat tacgccaagc gcgcaattaa    7620
ccctcactaa agggaacaaa agctg                                           7645

SEQ ID NO: 68           moltype = DNA    length = 3755
FEATURE                 Location/Qualifiers
misc_feature            1..3755
                        note = pD902e
source                  1..3755
                        mol_type = other DNA
                        organism = synthetic construct
SEQUENCE: 68
cttcagtaat gtcttgtttc ttttgttgca gtggtgagcc attttgactt cgtgaaagtt    60
tctttagaat agttgtttcc agaggccaaa cattccaatc ctgattaaagt gcaagcgtag   120
gaagaccaag actggcataa atcaggtata agtgtcgagc actggcaggt gatcttctga   180
aagtttctac tagcagataa gatccagtag tcatgcatat ggcaacaatg taccgtgtgg   240
atctaagaac gcgtcctact aaccttcgca ttcgttggtc cagtttgttg ttatcgatca   300
acgtagcaag gttgtcgatt ccgcgtaagc atgcatccaa aaggacgcct gttgcaattc   360
caagtgagcc agttccaaca atctttgtaa tattagagca cttcattgtg ttgcgcttga   420
aagtaaaatg cgaacaaatt aagagataat ctcgaaaccg cgacttcaaa cgccaatatg   480
atgtgcggca cacaataagc gttcatatcc gctgggtgac tttctcgctt taaaaaatta   540
tccgaaaaaa ttttctagag tgttgttact ttatacttcc ggctcgtata atacgacaag   600
gtgtaaggag gactaaacca tggctaaact cacctctgct gttccagtcc tgactgctcg   660
tgatgttgct ggtgctgttg agtctggac tgatagactc ggtttctccc gtgacttcgt    720
agaggacgac tttgccggtg ttgtacgtga cgacgttacc ctgttcatct ccgcagttca   780
ggaccaggtt gtgccagaca acactctggc atgggtatgg gttcgtggtc tggacgaact   840
gtacgctgag tggtctgaag tcgtgtctac caacttcgt gatgcatctg tccagctat    900
gaccgagatc ggtgaacagc cctggggtcg tgagtttgca ctgcgtgatc cagctggtaa   960
ctgcgtgcat ttcgtcgcag aagaacagga ctaacaattg acaccttacg attatttaga  1020
gagtatttat tagttttatt gtatgtatac ggatgttta ttatctattt atgcccttat    1080
attctgtaac tatccaaaag tcctatctta tcaagccagc aatctatgtc cgcgaacgtc   1140
aactaaaaat aagcttttta tgctgttctc tcttttttc ccttcggtat aattatacct    1200
tgcatccaca gattctcctg ccaaattttg cataatcctt tacaacatgg ctatatggga   1260
gcacttagcg ccctccaaaa cccatattgc ctacgcatgt ataggtgttt tttccacaat   1320
attttctctg tgctctcttt ttattaaaga gaagctctat atcggagaag cttctgtggc   1380
cgttatattc ggccttatcg tgggaccaca ttgcctgaat tggtttgccc ggaagattg    1440
gggaaacttg gatctgatta ccttagctgc aggtaccact gagcgtcaga ccccgtagaa   1500
aagatcaaag gatcttcttg agatcctttt tttctgcgcg taatctgctg cttgcaaaca   1560
aaaaaaccac cgctaccagc ggtggttttgt ttgccggatc agagctacc aactctttt    1620
ccgaaggtaa ctggcttcag cagagcgcag ataccaaata ctgttcttct agtgtagccg   1680
tagttaggcc accacttcaa gaactctgta gcaccgccta catacctcgc tctgctaatc   1740
ctgttaccag tggctgctgc cagtggcgat aagtcgtgtc ttaccgggtt ggactcaaga   1800
cgatagttac cggataaggc gcagcggtcg ggctgaacgg ggggttcgtg cacacagccc   1860
agcttggagc gaacgaccta caccgaactg agatacctac agcgtgagct atgagaaagc    1920
gccacgcttc ccgaagggag aaaggcggac aggtatccgg taagcggcag gtcggaaca    1980
ggagagcgca cgagggagct tccaggggga acgcctggta tctttatag tcctgtcggg    2040
tttcgccacc tctgacttga gcgtcgattt ttgtgatgct cgtcaggggg gcggagccta    2100
tggaaaaacg ccagcaacgc ggcctttta cggttcctgg ccttttgctg gccttttgct    2160
cacatgttct ttcctgcggt acccagatcc aattcccgct ttgactgcct gaaatctcca   2220
tcgcctacaa tgatgacatt tggatttggt tgactcatgt tggtattgtg aaatagacgc    2280
agatcgggaa cactgaaaaa tacacagtta ttattcattt aaataacatc caaagacgaa   2340
aggttgaatg aaaccttttt gccatccgac atccacaggt ccattctcac acataagtgc   2400
caaacgcaac aggaggggat acactagcag cagaccgttg caaacgcagg acctccactc    2460
ctcttctcct caacacccac ttttgccatc gaaaaaccag cccagttatt gggcttgatt    2520
ggagctcgct cattccaatt cctcctatta ggctactaac accatgactt tattagcctg    2580
tctatcctgg ccccccttgg gaggttcatg tttgtttatt tccgaatgca acaagctcga   2640
cattacaccc gaacatcact ccagatgagg gctttctgag tgtggggtca aatagtttca   2700
tgttccccaa atgcccaaa actgacagtt taaacgctgt cttggaacct aatatgacaa    2760
aagcgtgatc tcatccaaga tgaactaagt ttggttcgtt gaaatgctaa cggcagttg    2820
gtcaaaaga aacttccaaa agtcggcaca ccgtttgtct tgtttggtat tgattgacga    2880
atgctcaaaa ataatctcat taatgcttag cgcagtcctt ctatcgcttc tgaacccgca    2940
tgcacctgtg ccgaaacgca aatggggaaa caccgcttt ttgatgatt atgcattgtc      3000
tccacattgt atgcttccaa gattctgtg ggaatactgc tgatagccta acgttcatga    3060
tcaaaattta actgttctaa cccctacttg acagcaatat ataaacagaa ggaagctgcc    3120
ctgtcttaaa ccctttttt tatcatcatt attagcttac tttcataatt gcgactggtt    3180
ccaattgaca agcttttgat tttaacgact tttaacgaca acttagaag atcaaaaac     3240
aactaattat tgaaagaatt caaaacgatg tttgcaaag aaggtgaaaa tgaaggttga    3300
aggggcggcc gctcaagagg atgtcagaat gccatttgcc tgagagatgc aggcttcatt    3360
tttgatactt ttttatttgt aacctatata gtataggatt tttttgtca ttttgttct     3420
tctcgtacga gcttgctcct gatcagccta tctcgcagca gatgaatatc ttgtggtagg    3480
ggtttgggaa aatcattcga gtttgatgtt tttcttggta tttcccactc ctcttcagag    3540
```

```
tacagaagat taagtgaaac cttcgtttgt gcggatccca ccggcgcaat taatatttac    3600
ttattttggt caaccccaaa taggttgatt tcatacttgg ttcattcaaa aataagtagt    3660
cttttgagat ctttcaatat tataataaat atactataac agccgacttg tttcattttc    3720
gcgaatgttc ccccagctta tccaccggcg ggatc                               3755

SEQ ID NO: 69           moltype = DNA   length = 990
FEATURE                 Location/Qualifiers
misc_feature            1..990
                        note = ldhA-sc
source                  1..990
                        mol_type = genomic DNA
                        organism = Escherichia coli
SEQUENCE: 69
atgaagttgg ctgtttactc taccaagcaa tacgacaaga agtacttgca acaagttaac    60
gaatctttcg gtttcgaatt ggaattcttc gacttcttgt tgaccgaaaa gaccgctaag   120
accgctaacg gttgtgaagc tgtttgtatt tcgttaacg acgacggttc tagaccagtt   180
ttggaagaat gaagaagca cggtgttaag tacattgctt tgagatgtgc tggtttcaac   240
aacgttgact tggacgctgc taaggaattg gtttgaagtt gttagagt tccagcttac   300
gacccagaag ctgttgctga acacgctatt ggtatgatga tgaccttgaa cagaagaatt   360
cacagagctt accaaagaac cagagacgct aacttctctt tggaaggttt gaccggtttc   420
accatgtacg gtaagaccgc tggtgttatt ggtaccggta agattggtgt tgctatgttg   480
agaattttga aggtttcgg tatgaattg ttggcttttg acccatacc atctgctgct   540
gctttggaat tgggtgttga atacgttgac ttgccaacct tgttctctga atctgacgtt   600
atttctttgc actgtccatt gaccccagaa aactaccact tgttaacga agctgctttc   660
gaacaaatga agaacggtgt tatgattgtt aacacctcta gaggtgcttt gattgactct   720
caagctgcta ttgaagcttt gaaaaaccaa aagattgctc ttggggtat ggacgtttac   780
gaaaacgaaa gagacttgtt cttcgaagac aagtctaacg acgttattca agacgacgtt   840
ttcagaagat tgtctgcttg tcacaacgtt ttgttcaccg gtcaccaagc tttcttgacc   900
gctgaagctt tgacctctat ttctcaaacc accttgcaaa acttgtctaa cttggaaaag   960
ggtgaaacct gtccaaacga attggtttaa                                    990

SEQ ID NO: 70           moltype = AA    length = 329
FEATURE                 Location/Qualifiers
REGION                  1..329
                        note = ldhA-sc_AA
source                  1..329
                        mol_type = protein
                        organism = Escherichia coli
SEQUENCE: 70
MKLAVYSTKQ YDKKYLQQVN ESFGFELEFF DFLLTEKTAK TANGCEAVCI FVNDDGSRPV    60
LEELKKHGVK YIALRCAGFN NVDLDAAKEL GLKVVRVPAY DPEAVAEHAI GMMMTLNRRI   120
HRAYQRTRDA NFSLEGLTGF TMYGKTAGVI GTGKIGVAML RILKGFGMRL LAFDPYPSAA   180
ALELGVEYVD LPTLFSESDV ISLHCPLTPE NYHLLNEAAF EQMKNGVMIV NTSRGALIDS   240
QAAIEALKNQ KIGSLGMDVY ENERDLFFED KSNDVIQDDV FRRLSACHNV LFTGHQAFLT   300
AEALTSISQT TLQNLSNLEK GETCPNELV                                     329

SEQ ID NO: 71           moltype = DNA   length = 7337
FEATURE                 Location/Qualifiers
misc_feature            1..7337
                        note = pYP024
source                  1..7337
                        mol_type = other DNA
                        organism = synthetic construct
SEQUENCE: 71
ctcgtaggaa caatttcggg cccctgcgtg ttcttctgag gttcatcttt tacatttgct    60
tctgctggat aattttcaga ggcaacaagg aaaaattaga tggcaaaaag tcgtctttca   120
aggaaaaatc cccaccatct ttcgagatcc cctgtaactt attggcaact gaaagaatga   180
aaggaggaa atacaaaat atactagaac tgaaaaaaa aagtataaa tagagacgat   240
atatgccaat acttcacaat gttcgaatct attcttcatt tgcagctatt gtaaaataat   300
aaaacatcaa gaacaaacaa gctcaacttg tcttttctaa gaacaaagaa taaacacaaa   360
aacaaaaagt ttttttaatt ttaatcaaaa aatgaagttg gctgtttact ctaccaagca   420
atacgacaag aagtacttgc aacaagttaa cgaatctttc ggtttcgaat tggaattctt   480
cgacttcttg ttgaccgaaa agaccgctaa gaccgctaac ggttgtgaag ctgtttgtat   540
tttcgttaac gacgacggtt ctagaccagt tttggaagaa ttgaagaagc acggtgttaa   600
gtacattgct ttgagatgtg ctggtttcaa caacgttgac ttggacgctg ctaaggaatt   660
gggtttgaag gttgttagag ttccagctta cgacccagaa gctgttgctg aacacgctat   720
tggtatgatg atgaccttga acagaagaat tcacagagct taccaaagaa ccagagacgc   780
taacttctct ttggaaggtt tgaccggttt caccatgtac ggtaagaccg ctggtgttat   840
tggtaccggt aagattggtg ttgctatgtt gagaattttg aaggtttcg tatgagattt   900
gttggctttc gacccatacc catctgctgc tgctttggaa ttgggtgttg aatacgttga   960
cttgccaacc ttgttctctg aatctgacgt tatttctttg cactgtccat tgaccccaga  1020
aaactaccac ttgttaacg aagctgcttt cgaacaaatg aagaacggtg ttatgattgt  1080
taacacctct agaggtgctt tgattgactc tcaagctgct attgaagctt tgaagaacca  1140
aaagattggt tcttttgggta tggacgttta cgaaaacgaa agagacttgt tcttcgaaga  1200
caagtctaac gacgttattc aagacgacgt tttcagaaga ttgtctgctt gtcacaacgt  1260
tttgttcacc ggtcaccaag ctttcttgac cgctgaagct ttgacctcta tttctcaaac  1320
caccttgcaa aacttgtcta acttggaaaa gggtgaaacc tgtccaaacg aattggttta  1380
actcgagtca tgtaattagt tatgtcacgc ttacattcac gccctccccc cacatccgct  1440
ctaaccgaaa aggaaggagt tagacaacct gaagtctagg tccctattta ttttttata  1500
```

```
gttatgttag tattaagaac gttatttata tttcaaattt ttcttttttt tctgtacaga   1560
cgcgtgtacg catgtaacat tatactgaaa accttgcttg agaaggtttt gggacgctcg   1620
aaggctttaa tttgcggccg gtacccaatt cgccctatag tgagtcgtat tacgcgcgct   1680
cactggccgt cgttttacaa cgtcgtgact gggaaaaccc tggcgttacc caacttaatc   1740
gccttgcagc acatccccct ttcgccagct ggcgtaatag cgaagaggcc cgcaccgatc   1800
gcccttccca acagttgcgc agcctgaatg gcgaatggcg cgacgcgccc tgtagcggcg   1860
cattaagcgc ggcgggtgtg gtggttacgc gcagcgtgac cgctacactt gccagcgccc   1920
tagcgcccgc tcctttcgct ttcttccctt cctttctcgc cacgttcgcc ggctttcccc   1980
gtcaagctct aaatcggggg ctcccttag ggttccgatt tagtgcttta cggcacctcg   2040
accccaaaaa acttgattag ggtgatggtt cacgtagtgg gccatcgccc tgatagacgg   2100
tttttcgccc tttgacgttg gagtccacgt tctttaatag tggactcttg ttccaaactg   2160
gaacaacact caaccctatc tcggtctatt cttttgattt ataagggatt ttgccgattt   2220
cggcctattg gttaaaaaat gagctgattt aacaaaaatt taacgcgaat tttaacaaaa   2280
tattaacgtt tacaatttcc tgatgcggta ttttctcctt acgcatctgt gcggtatttc   2340
acaccgcata gatccgtcga gttcaagaga aaaaaaaga aaaagcaaaa agaaaaaagg   2400
aaagcgcgcc tcgttcagaa tgacacgtat agaatgatgc attaccttgt catcttcagt   2460
atcatactgt tcgtatacat acttactgac attcataggt atacatatat acacatgtat   2520
atatatcgta tgctgcagct ttaaataatc ggtgtcacta cataagaaca cctttggtgg   2580
agggaacatc gttggtacca ttgggcgagg tggcttctct tatggcaacc gcaagagcct   2640
tgaacgcact ctcactacgg tgatgatcat tcttgcctcg cagacaatca acgtggaggg   2700
taattctgct agcctctgca aagctttcaa gaaaatgcgg gatcatctcg caagagagat   2760
ctcctacttt ctcccctttgc aaaccaagtt cgacaactgc gtacggcctg ttcgaaagat   2820
ctaccaccgc tctggaaagt gcctcatcca aaggcgcaaa tcctgatcca aacctttta   2880
ctccacgcgc cagtagggcc tctttaaaag cttgaccgag agcaatcccg cagtcttcag   2940
tggtgtgatg gtcgtctatg tgtaagtcac caatgcactc aacgattagc gaccagccgg   3000
aatgcttggc cagagcatgt atcatatggt ccagaaaccc tatacctgtg tggacgttaa   3060
tcacttgcga ttgtgtggcc tgttctgcta ctgcttctgc ctcttttct gggaagatcg   3120
agtgctctat cgctagggga ccacccttta aagagatcgc aatctgaatc ttggtttcat   3180
ttgtaatacg ctttactagg gctttctgct ctgtcatctt tgccttcgtt tatcttgcct   3240
gctcatttt tagtatattc ttcgaagaaa tcacattact ttatataatg tataattcat   3300
tatgtgataa tgccaatcgc taagaaaaaa aaagagtcat ccgctagggg aaaaaaaaaa   3360
atgaaaatca ttaccgaggc ataaaaaaat atagagtgta ctagaggagg ccaagagtaa   3420
tagaaaaaga aaattgcggg aaaggactgt gttatgactt ccctgactaa tgccgtgttc   3480
aaacgatacc tggcagtgac tcctagcgct caccaagctc ttaaaacggg aatttatggt   3540
gcactctcag tacaatctgc tctgatgccg catagttaag ccagccccga caccgccaa   3600
cacccgctga cgcgccctga cgggcttgtc tgctcccggc atccgcttac agacaagctg   3660
tgaccgtctc cgggagctgc atgtgtcaga ggttttcacc gtcatccg aaacgcgcga   3720
gacgaaaggg cctcgtgata cgcctatttt tataggttaa tgtcatgata ataatggttt   3780
cttagatgat ccaatatcaa aggaaatgat agcattgaa gatgagacta atccaattga   3840
ggagtggcag catatagaac agctaaaggg tagtgctgaa ggaagcatac gatacccgc   3900
atggaatggg ataatatcac aggaggtact agactacctt tcatcctaca taatagacg   3960
catataagta cgcatttaag cataaacacg cactatgccg ttcttctcat gtatatatat   4020
atacaggcaa cacgcagata taggtgcgac gtgaacagtg agctgtatgt gcgcagctcg   4080
cgttgcattt tcggaagcgc tcgttttcgg aaacgctttg aagttcctat tccgaagttc   4140
ctattctcta gaaagtatag gaacttcaga gcgcttttga aaaccaaaag cgctctgaag   4200
acgcactttt aaaaaaccaa aaacgcaccg gactgtaacg agctactaaa atattgcgaa   4260
taccgcttcc acaaacattg ctcaaaagta tctcttgct atatatctct gtgctatatc   4320
cctatataac ctaccatcc accttttcgct ccttgaactt gcatctaaac tcgacctcta   4380
cattttttat gtttatctct agtattactc tttagacaaa aaaattgtag taagaactat   4440
tcatagagtg aatcgaaaac aatacgaaaa tgtaaacatt tcctatacgt agtatataga   4500
gacaaaatag aagaaaccgt tcataatttt ctgaccaatg aagaatcatc aacgctatca   4560
ctttctgttc acaaagtatg cgcaatccac atcggtatag aatataatcg gggatgcctt   4620
tatcttgaaa aaatgcaccc gcagcttcgc tagtaatcag taaacgcggg aagtggagtc   4680
aggctttttt tatggaagag aaaatagaca ccaaagtagc cttcttctaa ccttaacgga   4740
cctacagtgc aaaaagttat caagagactg cattatagag cgcacaaagg agaaaaaaag   4800
taatctaaga tgctttgtta gaaaaatagc gctctcggga tgcattttg tagaacaaaa   4860
aagaagtata gattctttgt tggtaaaata gcgctctcgc gttgcatttc tgttctgtaa   4920
aaatgcagct cagattcttt gtttgaaaaa ttagcgctct cgcgttgcat ttttgtttta   4980
caaaaatgaa gcacagattc ttcgttggta aaatagcgct ttgcgttgc atttctgttc   5040
tgtaaaaatg cagctcagat tctttgtttg aaaaattagc gctctcgcgt tgcattttg   5100
ttctacaaaa tgaagcacag atgcttcgtt caggtggcac ttttcgggga atgtgcgcg   5160
gaaccccctat ttgtttattt ttctaaatac attcaaatat gtatccgctc atgagacaat   5220
aaccctgata aatgcttcaa taatattgaa aaaggaagag tatgagtatt caacatttcc   5280
gtgtcgccct tattcccttt tttgcggcat tttgccttcc tgttttttgc cacccagaaa   5340
cgctggtgaa agtaaaagat gctgaagatc agttgggtgc acgagtgggt tacatcgaac   5400
tggatctcaa cagcggtaag atccttgaga gttttcgccc cgaagaacgt tttccaatga   5460
tgagcacttt taaagttctg ctatgtggcg cggtattatc ccgtattgac gccgggcaag   5520
agcaactcgg tcgccgcata cactattctc agaatgactt ggttgagtac tcaccagtca   5580
cagaaaagca tcttacggat ggcatgacag taagagaatt atgcagtgct gccataacca   5640
tgagtgataa cactgcggcc aacttacttc tgacaacgat cggaggaccg aaggagctaa   5700
ccgcttttttt gcacaacatg gggatcatg taactcgcct tgatcgttgg aaccggagc   5760
tgaatgaagc cataccaaac gacgagcgtg acaccacgat gcctgtagca atggcaacaa   5820
cgttgcgcaa actattaact ggcgaactac ttactctagc ttcccggcaa caattaatag   5880
actggatgga ggcggataaa gttgcaggac cacttctgcg ctcggccctt ccggctggct   5940
ggtttattgc tgataaatct ggagccggtg agcgtgggtc tcgcggtatc attgcagcac   6000
tggggccaga tggtaagccc tcccgtatcg tagttatcta cacgacgggg agtcaggcaa   6060
ctatggatga acgaaataga cagatcgctg agataggtgc ctcactgatt aagcattggt   6120
aactgtcaga ccaagtttac tcatatatac tttagattga tttaaaactt catttttaat   6180
ttaaaaggat ctaggtgaag atcctttttg ataatctcat gaccaaaatc ccttaacgtg   6240
```

-continued

```
agttttcgtt ccactgagcg tcagaccccg tagaaaagat caaaggatct tcttgagatc 6300
cttttttct  gcgcgtaatc tgctgcttgc aaacaaaaaa accaccgcta ccagcggtgg 6360
tttgtttgcc ggatcaagag ctaccaactc tttttccgaa ggtaactggc ttcagcagag 6420
cgcagatacc aaatactgtc cttctagtgt agccgtagtt aggccaccac ttcaagaact 6480
ctgtagcacc gcctacatac ctcgctctgc taatcctgct accagtggct gctgccagtg 6540
gcgataagtc gtgtcttacc gggttggact caagacgata gttaccggat aaggcgcagc 6600
ggtcgggctg aacggggggt tcgtgcacac agcccagctt ggagcgaacg acctacaccg 6660
aactgagata cctacagcgt gagctatgag aaagcgccac gcttcccgaa gggagaaagg 6720
cggacaggta tccggtaagc ggcagggtcg gaacaggaga gcgcacgagg gagcttccag 6780
ggggaaacgc ctggtatctt tatagtcctg tcgggtttcg ccacctctga cttgagcgtc 6840
gattttgtg atgctcgtca gggggcgga gcctatggaa aaacgccagc aacgcggcct 6900
ttttacggtt cctggccttt tgctggccttt ttgctcacat gttctttcct gcgttatccc 6960
ctgattctgt ggataaccgt attaccgcct ttgagtgagc tgataccgct cgccgcagcc 7020
gaacgaccga gcgcagcgag tcagtgagcg aggaagcgga agagcgccca atacgcaaac 7080
cgcctctccc cgcgcgttgg ccgattcatt aatgcagctg gcacgacagg tttcccgact 7140
ggaaagcggg cagtgagcgc aacgcaatta atgtgagtta cctcactcat taggcacccc 7200
aggctttaca ctttatgctt ccggctccta tgttgtgtgg aattgtgagc ggataacaat 7260
ttcacacagg aaacagctat gaccatgatt acgccaagcg cgcaattaac cctcactaaa 7320
gggaacaaaa gctggag                                                7337
```